United States Patent
Dodd et al.

(10) Patent No.: US 8,829,195 B2
(45) Date of Patent: Sep. 9, 2014

(54) COMPOUNDS AND COMPOSITIONS FOR INHIBITING THE ACTIVITY OF ABL1, ABL2 AND BCR-ABL1

(71) Applicants: Stephanie Kay Dodd, Ayer, MA (US); Pascal Furet, Thann (FR); Robert Martin Grotzfeld, Ettingen (CH); Wolfgang Jahnke, Lorrach (DE); Darryl Brynley Jones, Basel (CH); Paul William Manley, Arlesheim (CH); Andreas Marzinzik, Weil (DE); Xavier Francois Andre Pelle, Kembs (FR); Bahaa Salem, Basel (CH); Joseph Schoepfer, Riehen (CH)

(72) Inventors: Stephanie Kay Dodd, Ayer, MA (US); Pascal Furet, Thann (FR); Robert Martin Grotzfeld, Ettingen (CH); Wolfgang Jahnke, Lorrach (DE); Darryl Brynley Jones, Basel (CH); Paul William Manley, Arlesheim (CH); Andreas Marzinzik, Weil (DE); Xavier Francois Andre Pelle, Kembs (FR); Bahaa Salem, Basel (CH); Joseph Schoepfer, Riehen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/892,769

(22) Filed: May 13, 2013

(65) Prior Publication Data

US 2013/0310395 A1 Nov. 21, 2013

Related U.S. Application Data

(60) Provisional application No. 61/790,967, filed on Mar. 15, 2013, provisional application No. 61/647,174, filed on May 15, 2012.

(51) Int. Cl.
| | |
|---|---|
| *C07D 401/00* | (2006.01) |
| *C07D 211/72* | (2006.01) |
| *C07D 211/84* | (2006.01) |
| *C07D 211/56* | (2006.01) |
| *A01N 43/40* | (2006.01) |
| *A61K 31/44* | (2006.01) |
| *C07D 405/14* | (2006.01) |
| *C07D 401/10* | (2006.01) |
| *C07D 401/04* | (2006.01) |
| *C07D 213/82* | (2006.01) |
| *A61K 45/06* | (2006.01) |
| *C07D 403/10* | (2006.01) |
| *C07F 9/58* | (2006.01) |
| *A61K 31/4439* | (2006.01) |
| *A61K 31/506* | (2006.01) |
| *C07D 401/14* | (2006.01) |

(52) U.S. Cl.
CPC ............ *C07D 401/10* (2013.01); *C07D 405/14* (2013.01); *C07D 401/04* (2013.01); *C07D 213/82* (2013.01); *A61K 45/06* (2013.01); *C07D 403/10* (2013.01); *C07F 9/58* (2013.01); *A61K 31/4439* (2013.01); *A61K 31/506* (2013.01); *C07D 401/14* (2013.01)
USPC .................. 546/275.4; 546/275.7; 546/276.4; 546/316; 514/341; 514/343; 514/355

(58) Field of Classification Search
USPC ........................................ 514/341; 546/275.7
See application file for complete search history.

(56) References Cited

U.S. PATENT DOCUMENTS

| | | |
|---|---|---|
| 5,017,211 A | 5/1991 | Wenger et al. |
| 7,642,272 B2 | 1/2010 | Shankar et al. |
| 8,030,336 B2 | 10/2011 | Burns et al. |
| 2003/0105143 A1 | 6/2003 | Ammendola et al. |
| 2008/0167347 A1 | 7/2008 | Seno et al. |
| 2010/0041657 A1 | 2/2010 | Olesen et al. |
| 2011/0312939 A1 | 12/2011 | Steurer et al. |
| 2012/0149910 A1 | 6/2012 | Mihara et al. |
| 2013/0053370 A1 | 2/2013 | Son et al. |

FOREIGN PATENT DOCUMENTS

| | | |
|---|---|---|
| EP | 1746097 A1 | 1/2007 |
| WO | 8902891 A1 | 4/1989 |
| WO | 01/55115 A1 | 8/2001 |
| WO | 03055477 A1 | 7/2003 |
| WO | 2004/005281 A1 | 1/2004 |
| WO | 2004005281 A1 | 1/2004 |
| WO | 2006/039718 A2 | 4/2006 |
| WO | 2008/021725 A2 | 2/2008 |
| WO | 2008/051757 A1 | 5/2008 |
| WO | 2008/112695 A2 | 9/2008 |
| WO | 2008/124393 A1 | 10/2008 |
| WO | 2008/144253 A1 | 11/2008 |
| WO | 2009/016088 A1 | 2/2009 |
| WO | 2009/039127 A1 | 3/2009 |
| WO | 2009/152356 A2 | 12/2009 |
| WO | 2009152356 A2 | 12/2009 |
| WO | 2011008788 A1 | 1/2011 |
| WO | 2011060295 A1 | 5/2011 |
| WO | 2011/082400 A2 | 7/2011 |
| WO | 2012/129562 A2 | 9/2012 |
| WO | 2012/166951 A2 | 12/2012 |
| WO | 2013/171639 A1 | 11/2013 |
| WO | 2013/171640 A1 | 11/2013 |
| WO | 2013/171641 A1 | 11/2013 |
| WO | 2013/171642 A1 | 11/2013 |

OTHER PUBLICATIONS

Li, et al., "Design, Synthesis, and Biologicl Evaluation of 3-(1H-1,2,3-Triazol-1-yl)benzamide Derivatives as Potent Pan Bcr-Abl Inhibitors Including the Threonin 315->Isoleucine315 Mutant", Journal of Medicinal Chemistry, Nov. 26, 2012, pp. 10033-10046, vol. 55, No. 22, American Chemical Society, US.

Eck, et al., "The interplay of structural information and functional studies in kinase drug design: insights from BCR-Abl", Current Opinion in Cell Biology, Apr. 1, 2009, pp. 288-295, vol. 21, No. 2.

*Primary Examiner* — John Mabry
*Assistant Examiner* — Daniel Carcanague
(74) *Attorney, Agent, or Firm* — Scott W. Reid

(57) ABSTRACT

The present invention relates to compounds of formula (I):

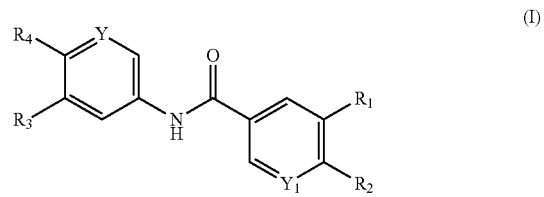

in which Y, $Y_1$, $R_1$, $R_2$, $R_3$ and $R_4$ are defined in the Summary of the Invention; capable of inhibiting the activity of BCR-ABL1 and mutants thereof. The invention further provides a process for the preparation of compounds of the invention, pharmaceutical preparations comprising such compounds and methods of using such compounds in the treatment of cancers.

16 Claims, 4 Drawing Sheets

COMPOUNDS AND COMPOSITIONS FOR INHIBITING THE ACTIVITY OF ABL1, ABL2 AND BCR-ABL1

FIELD OF THE INVENTION

The present invention relates to compounds capable of inhibiting the tyrosine kinase enzymatic activity of the Abelson protein (ABL1), the Abelson-related protein (ABL2) and related chimeric proteins, in particular BCR-ABL1. The invention further provides a process for the preparation of compounds of the invention, pharmaceutical preparations comprising such compounds and methods of using such compounds in the treatment of cancers.

BACKGROUND OF THE INVENTION

The tyrosine kinase activity of the ABL1 protein is normally tightly regulated, with the N-terminal cap region of the SH3 domain playing an important role. One regulatory mechanism involves the N-terminal cap glycine-2 residue being myristoylated and then interacting with a myristate binding site within the SH1 catalytic domain. A hallmark of chronic myeloid leukemia (CML) is the Philadelphia chromosome (Ph), formed by the t(9,22) reciprocal chromosome translocation in a haematopoietic stem cell. This chromosome carries the BCR-ABL1 oncogene which encodes the chimeric BCR-ABL1 protein, that lacks the N-terminal cap and has a constitutively active tyrosine kinase domain.

Although drugs that inhibit the tyrosine kinase activity of BCR-ABL1 via an ATP-competitive mechanism, such as Gleevec®/Glivec® (imatinib), Tasigna® (nilotinib) and Sprycel® (dasatinib), are effective in the treatment of CML, some patients relapse due to the emergence of drug-resistant clones, in which mutations in the SH1 domain compromise inhibitor binding. Although Tasigna® and Sprycel® maintain efficacy towards many Gleevec-resistant mutant forms of BCR-ABL1, the mutation in which the threonine-315 residue is replaced by an isoleucine (T315I) remains insensitive to all three drugs and can result in CML patients developing resistance to therapy. Therefore, inhibiting BCR-ABL1 mutations, such as T315I, remains an unmet medical need. In addition to CML, BCR-ABL1 fusion proteins are causative in a percentage of acute lymphocytic leukemias, and drugs targeting ABL kinase activity also have utility in this indication.

Agents targeting the myristoyl binding site (so-called allosteric inhibitors) have potential for the treatment of BCR-ABL1 disorders (J. Zhang, F. J. Adrian, W. Jahnke, S. W. Cowan-Jacob, A. G. Li, R. E. Iacob4, T. Sim, J. Powers, C. Dierks, F. Sun, G.-R. Guo, Q. Ding, B. Okram, Y. Choi, A. Wojciechowski, X. Deng, G. Liu, G. Fendrich, A. Strauss, N. Vajpai, S. Grzesiek, T. Tuntland, Y. Liu, B. Bursulaya, M. Azam, P. W. Manley, J. R. Engen, G. Q. Daley, M. Warmuth., N. S. Gray. Targeting BCR-ABL by combining allosteric with ATP-binding-site inhibitors. Nature 2010; 463:501-6). To prevent the emergence of drug resistance from ATP inhibitor and/or allosteric inhibitor use, a combination treatment using both types of inhibitor can be developed for the treatment of BCR-ABL1 related disorders. In particular, the need exists for small molecules, or combinations thereof, that inhibit the activity of BCR-ABL1 and BCR-ABL1 mutations via the ATP binding site, the myristoyl binding site or a combination of both sites.

Further, inhibitors of ABL1 kinase activity have the potential to be used as therapies for the treatment of metastatic invasive carcinomas and viral infections such as pox and Ebola viruses.

The compounds from the present invention also have the potential to treat or prevent diseases or disorders associated with abnormally activated kinase activity of wild-type ABL1, including non-malignant diseases or disorders, such as CNS diseases in particular neurodegenerative diseases (for example Alzheimer's, Parkinson's diseases), motoneuroneuron diseases (amyotophic lateral sclerosis), muscular dystrophies, autoimmune and inflammatory diseases (diabetes and pulmonary fibrosis), viral infections, prion diseases.

SUMMARY OF THE INVENTION

In one aspect, the present invention provides compounds of formula (I):

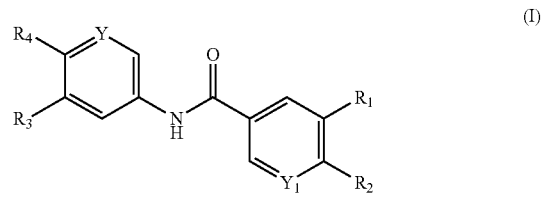

in which:

$R_1$ is pyrazolyl; wherein said pyrazolyl is unsubstituted or substituted with 1 to 2 $R_6$ groups;

$R_2$ is pyrrolidinyl; wherein said pyrrolidinyl is substituted with one $R_7$ group;

$R_3$ is selected from hydrogen and halo;

$R_4$ is selected from —$SF_5$ and —$Y_2$—$CF_2$—$Y_3$;

$R_6$ at each occurrence is independently selected from hydrogen, hydroxy, methyl, methoxy, cyano, trifluoromethyl, hydroxy-methyl, halo, amino, fluoro-ethyl, ethyl and cyclopropyl;

$R_7$ is selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyl)oxy, carboxy, methoxy-carbonyl, phosphonooxy, cyano and amino-carbonyl;

Y is selected from CH and N;

$Y_1$ is selected from CH and N;

$Y_2$ is selected from $CF_2$, O and $S(O)_{0-2}$; and $Y_3$ is selected from hydrogen, chloro, fluoro, methyl, difluoromethyl and trifluoromethyl.

In a second aspect, the present invention provides a pharmaceutical composition which contains a compound of formula (I) or a N-oxide derivative, individual isomers and mixture of isomers thereof, or a pharmaceutically acceptable salt thereof, in admixture with one or more suitable excipients.

In a third aspect, the present invention provides a method of treating a disease in an animal in which modulation of BCR-ABL1 activity can prevent, inhibit or ameliorate the pathology and/or symptomology of the disease, which method comprises administering to the animal a therapeutically effective amount of a compound of formula (I) or a N-oxide derivative, individual isomers and mixture of isomers thereof, or a pharmaceutically acceptable salt thereof.

In a fourth aspect, the present invention provides the use of a compound of formula (I) in the manufacture of a medicament for treating a disease in an animal in which BCR-ABL1 activity contributes to the pathology and/or symptomology of the disease.

In a fifth aspect, the present invention provides a compound of formula I for use in therapy in an animal in which BCR-ABL1 activity contributes to the pathology and/or symptomology of the disease.

In a sixth aspect, the present invention provides a process for preparing compounds of formula (I) and the N-oxide derivatives, prodrug derivatives, protected derivatives, individual isomers and mixture of isomers thereof, and the pharmaceutically acceptable salts thereof.

DEFINITIONS

Figure 1:
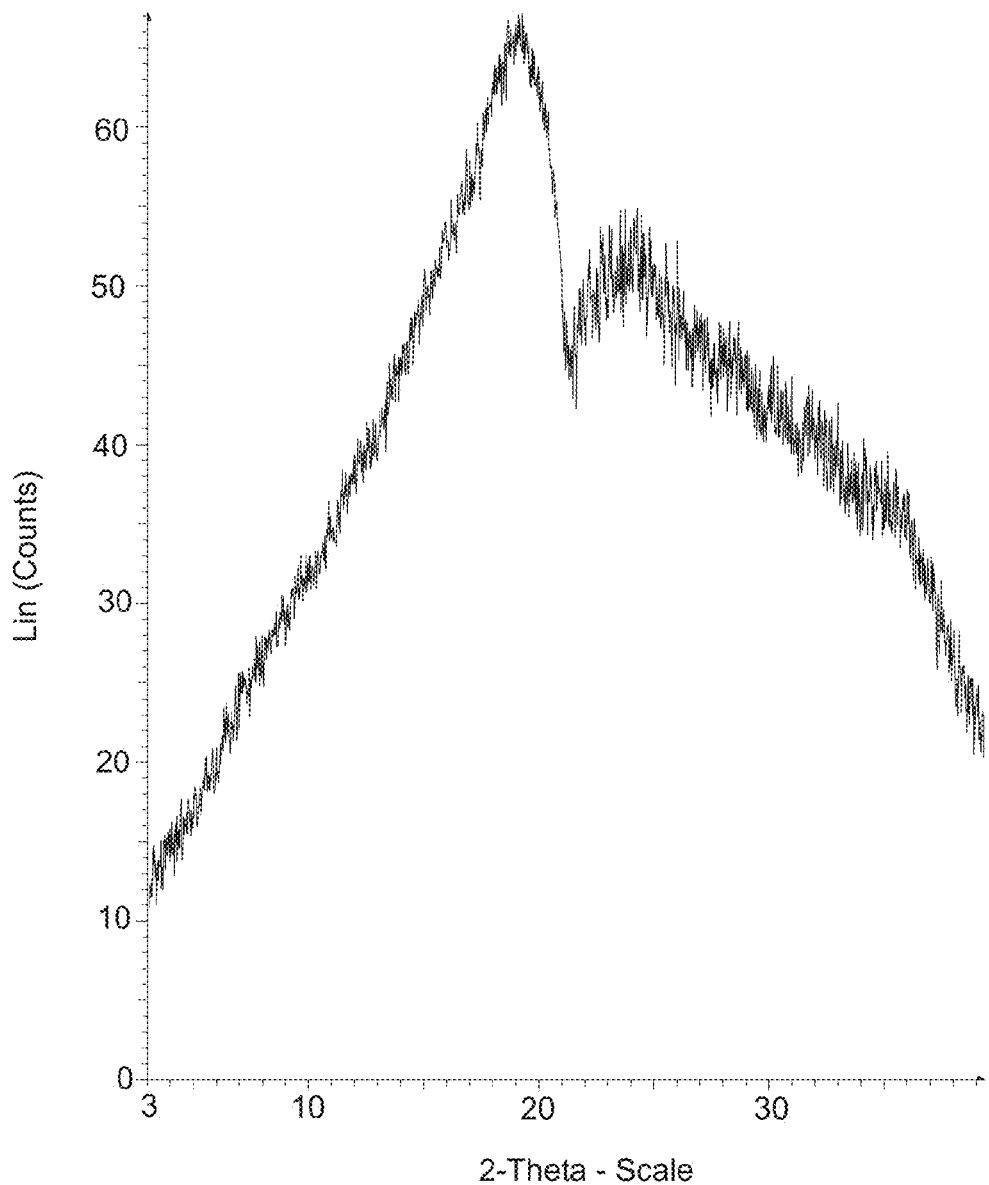
FIG. 1: X-ray powder diffraction pattern (using a copper source (lambda=1.54 A) for the measurement) for an amorphous solid dispersion formulation of Example 9 (see Example 41) having a 25% loading of Example 9 with PVP VA64 (37.5%) and Pharmacoat 603 (37.5%).

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Alkyl" refers to branched or unbranched hydrocarbon moieties having 1 to 7 carbon atoms ($C_{1-7}$alkyl), or 1 to 4 carbon atoms ($C_{1-4}$alkyl). Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups. Halo-substituted-alkyl and halo-substituted-alkoxy, can be either straight-chained or branched and includes, methoxy, ethoxy, difluoromethyl, trifluoromethyl, pentafluoroethyl, difluoromethoxy, trifluoromethoxy, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"BCR-ABL1" refers to a fusion protein created from the N-terminal exons of the breakpoint cluster region (BCR) gene and the major C-terminal part (exons 2-11) of the Abelson (ABL1) gene. The most common fusion transcripts encode for a 210-kDa protein (p210 BCR-ABL1), although rarer transcripts encode a 190-kDa protein (p190 BCR-ABL1) and a 230-kDa protein (p230 BCR-ABL1). The ABL1 sequences of these proteins contains an ABL1 tyrosine kinase domain which is tightly regulated in the wild-type protein, but constitutively activated in the BCR-ABL1 fusion proteins. This deregulated tyrosine kinase interacts with multiple cellular signalling pathways leading to transformation and deregulated proliferation of the cells.

"BCR-ABL1 mutants" refers to the numerous single site mutations in BCR-ABL1 including: Glu255→Lysine, Glu255→Valine, Thr315→Isoleucine, Met244→Val, Phe317→Leu, Leu248→Val, Met343→Thr, Gly250→Ala, Met351→Thr, Gly250→Glu, Glu355→Gly, Gln252→His, Phe358→Ala, Gln252→Arg, Phe359→Val, Tyr253→His, Val379→Ile, Tyr253→Phe, Phe382→Leu, Glu255→Lys, Leu387→Met, Glu255→Val, His396→Pro, Phe311→Ile, His396→Arg, Phe311→Leu, Ser417→Tyr, Thr315→Ile, Glu459→Lys and Phe486→Ser.

Compounds of the invention are sensitive to substitution on the $R_3/R_4$ substituted ring at the position that is ortho to the point of attachment of the NHC(O) group. Compare, for example, the following compounds of formula (I). The $IC_{50}$ of Example 2 is 1 nM compared to a chloro or methyl substitution with an $IC_{50}$ of 1.6 and 1.8 µM, respectively:

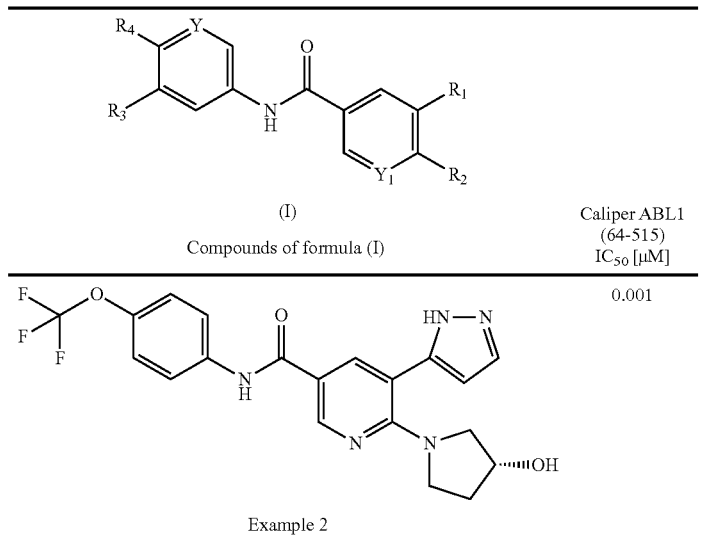

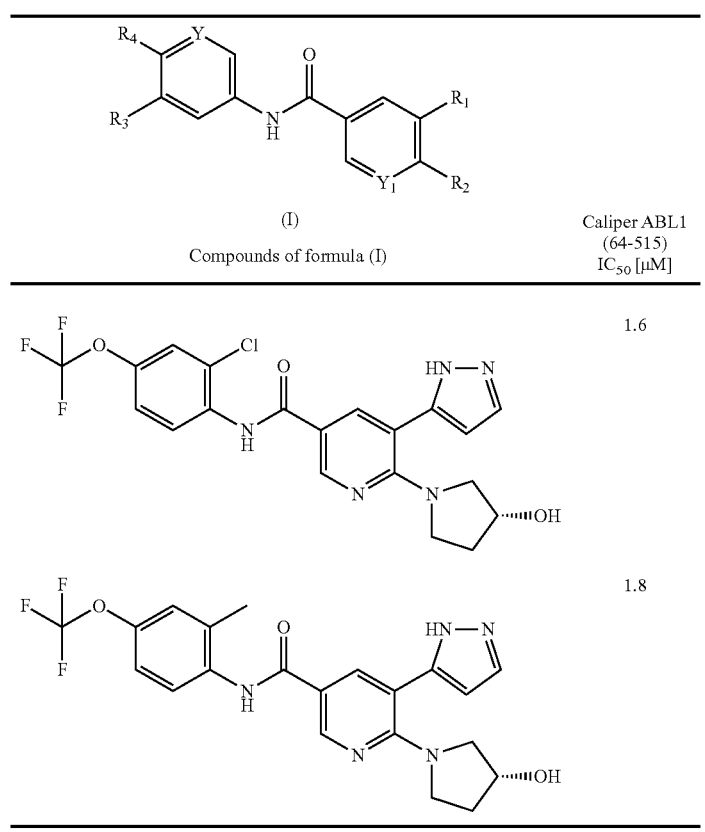

"Heteroaryl" is as defined for aryl above where one or more of the ring members is a heteroatom. For example a 5 to 8 member heteroaryl has a minimum of 5 ring members selected from carbon, nitrogen, oxygen and sulfur. Consequently, a 5 to 8 member heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. Partially unsaturated cycloalkyl means cycloalkyl as defined above with at least one bond being a double bond.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group (for example, carbobenzyloxy, p-methoxybenzyl carbonyl, t-butyyoxycarbonyl, acetyl, benzoyl, benzyl, p-methoxy-benzyl, p-methoxy-phenyl, 3,4-dimethoxybenzyl, and the like). For example, a 3 to 8 member heterocycloalkyl includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

GLEEVEC® (imatinib mesylates) is indicated for the treatment of patients with KIT (CD117)-positive unresectable and/or metastatic malignant gastrointestinal stromal tumors (GIST). It is also indicated to treat adult patients following complete gross resection of KIT (CD117)-positive GIST. It is also indicated for the treatment of newly diagnosed adult and pediatric patients with Philadelphia chromosome-positive chronic myeloid leukemia (Ph+ CML) in the chronic phase and patients with Ph+ CML in blast crisis (BC), accelerated phase (AP), or in the chronic phase (CP) after failure of interferon-alpha therapy. It can also be used as a targeted medicine for the treatment of the following rare disorders with limited treatment options: relapsed or refractory Philadelphia chromosome-positive acute lymphoblastic leukemia (Ph+ ALL); myelodysplastic/myeloproliferative diseases (MDS/MPD) associated with platelet-derived growth factor receptor (PDGFR) gene rearrangements; aggressive systemic mastocytosis (ASM) without the D816V c-KIT mutation or with c-KIT mutational status unknown; hypereosinophilic syndrome/chronic eosinophilic leukemia (HES/CEL) with the FIP1L1-PDGFRα fusion kinase (mutational analysis or FISH demonstration of CHIC2 allele deletion) and for patients with HES and/or CEL who are FIP1L1-PDGFRα fusion kinase negative or unknown; and unresectable, recurrent, and/or metastatic dermatofibrosarcoma protuberans (DFSP).

TASIGNA® (nilotinib) is indicated for the treatment of adult patients with newly diagnosed Philadelphia chromosome-positive chronic myeloid leukemia (Ph+ CML) in chronic phase It can be used to treat adults who are no longer benefiting from, or are intolerant to other treatments, including imatinib (GLEEVEC®), or have taken other treatments, including imatinib (GLEEVEC) but cannot tolerate them.

SPRYCEL® (dasatinib) is a prescription medicine used to treat adults who have newly diagnosed Philadelphia chromosome-positive (Ph+) chronic myeloid leukemia (CML) in chronic phase and to treat adults who are no longer benefiting or are intolerant to other treatments, as well as for patients with ALL.

BOSULIF® (Bosutinib) is a prescription medicine used to treat adults who have newly diagnosed Philadelphia chromosome-positive (Ph+) chronic myeloid leukemia (CML) in chronic phase and to treat adults who are no longer benefiting or are intolerant to other treatments, as well as for patients with ALL.

Compounds of formula (I) may have different isomeric forms. For example, any asymmetric carbon atom may be present in the (R)—, (S)— or (R,S)-configuration, preferably in the (R)— or (S)-configuration. Substituents at a double bond or especially a ring may be present in cis-(=Z—) or trans (=E—) form. The compounds may thus be present as mixtures of isomers or preferably pure isomers, preferably as pure diastereomers or pure enantiomers. The following compounds of formula (I) would exist in tautomeric form:

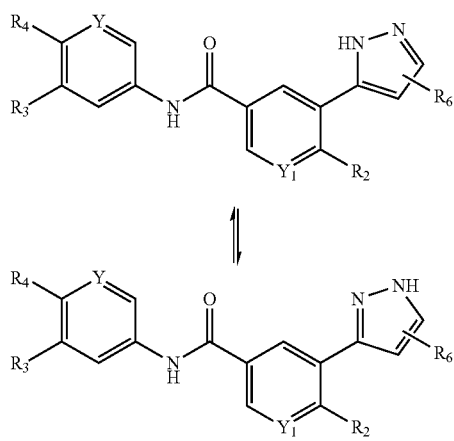

To illustrate tautomerism with the following specific examples, (R)—N-(4-(chlorodifluoromethoxy)phenyl)-6-(3-hydroxypyrrolidin-1-yl)-5-(1H-pyrazol-5-yl)nicotinamide (right structure, below) is a tautomer of (R)—N-(4-(chlorodifluoromethoxy)phenyl)-6-(3-hydroxypyrrolidin-1-yl)-5-(1H-pyrazol-3-yl)nicotinamide (left structure, below) and vice versa:

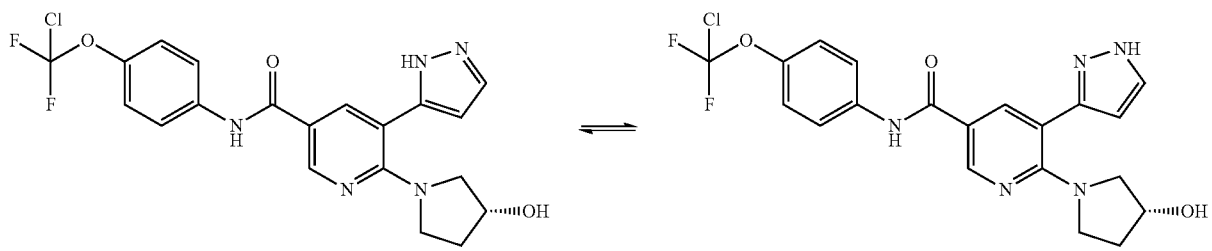 [SMILES: O=C(Nc1ccc(OC(F)(F)Cl)cc1)c1cnc(N2CC[C@@H](O)C2)c(-c2ccn[nH]2)c1 ; O=C(Nc1ccc(OC(F)(F)Cl)cc1)c1cnc(N2CC[C@@H](O)C2)c(-c2cc[nH]n2)c1]

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present, the "a" merely representing the indefinite article. "A" can thus preferably be read as "one or more", less preferably alternatively as "one".

The term "and/or an N-oxide thereof, a tautomer thereof and/or a (preferably pharmaceutically acceptable) salt thereof" especially means that a compound of the formula (I) may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula (I) and/or any of these forms or mixtures of two or more of such forms.

Any formulae given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of the invention can generally be prepared by conventional techniques known to those skilled in the art or by processes analogous to those described in the accompanying Examples using appropriate isotopically-labeled reagents.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

For example, a compound of formula Ib, shown here where $R_3$ is hydrogen and Y is CH, can incorporate deuterium on the pyrrolidinyl ring as shown:

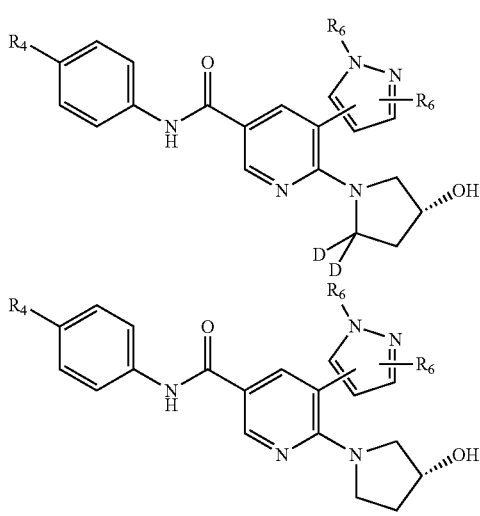

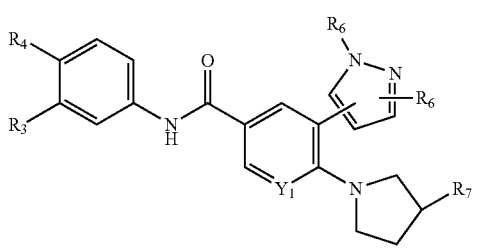

This deuterated form is less prone to metabolic transformation (left, above) compared with the none deutorated form (right, above).

DESCRIPTION OF PREFERRED EMBODIMENTS

The present invention relates to compounds capable of inhibiting the activity of BCR-ABL1 or mutants of BCR-ABL1 through the allosteric, myristoyl binding site.

In one embodiment, with respect to compounds of the invention, are compounds of formula (Ib):

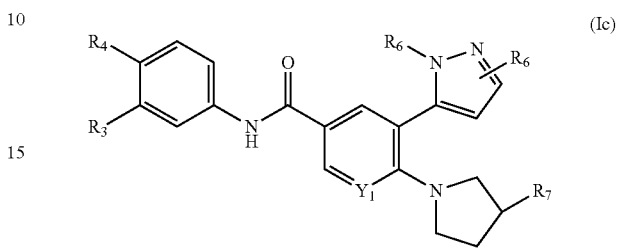

in which: $R_3$ is selected from hydrogen and halo; $R_4$ is selected from —$SF_5$ and —$Y_2$—$CF_2$—$Y_3$; $R_6$ when linked to a nitrogen of the pyrazolyl ring is selected from hydrogen, methyl, hydroxy-ethyl, fluoro-ethyl, ethyl and cyclopropyl; and $R_6$ when linked to a carbon atom of the pyrazolyl ring is selected from hydrogen, hydroxy, methyl, methoxy, cyano, trifluoromethyl, hydroxy-methyl, halo, amino, fluoro-ethyl, ethyl and cyclopropyl; $R_7$ is selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyl)oxy, carboxy, methoxy-carbonyl, phosphonooxy, cyano and amino-carbonyl; $Y_1$ is selected from CH and N; $Y_2$ is selected from $CF_2$, O and $S(O)_{0-2}$, $Y_3$ is selected from hydrogen, fluoro, chloro, methyl, difluoromethyl and trifluoromethyl; or the pharmaceutically acceptable salts thereof.

In a further embodiment are compounds of formula (Ic):

(Ic)

in which: $R_3$ is selected from hydrogen and halo; $R_4$ is selected from —$SF_5$ and —$Y_2$—$CF_2$—$Y_3$; $R_6$ when linked to a nitrogen of the pyrazolyl ring is selected from hydrogen, methyl, hydroxy-ethyl, fluoro-ethyl, ethyl and cyclopropyl; and $R_6$ when linked to a carbon atom of the pyrazolyl ring is selected from hydrogen, hydroxy, methyl, methoxy, cyano, trifluoromethyl, hydroxy-methyl, halo, amino, fluoro-ethyl, ethyl and cyclopropyl; $R_7$ is selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyl)oxy, carboxy, methoxy-carbonyl, phosphonooxy, cyano and amino-carbonyl; $Y_1$ is selected from CH and N; $Y_2$ is selected from $CF_2$, O and $S(O)_{0-2}$; $Y_3$ is selected from hydrogen, fluoro, chloro, methyl, difluoromethyl and trifluoromethyl; or the pharmaceutically acceptable salts thereof.

In another embodiment are compounds of formula (I), or the pharmaceutically acceptable salts thereof, in which $R_1$ is pyrazolyl; wherein said pyrazolyl is unsubstituted or substituted with 1 to 2 $R_6$ groups.

In a further embodiment, $R_1$ is an unsubstituted pyrazolyl.

In a further embodiment, $R_1$ is pyrazolyl substituted with one $R_6$ group.

In a further embodiment, $R_1$ is pyrazolyl substituted with two $R_6$ groups.

In another embodiment, $R_2$ is pyrrolidin-1-yl substituted with one $R_7$ group.

In another embodiment, Y is selected from CH and N.

In a further embodiment, Y is N.

In a further embodiment, Y is CH.

In another embodiment, $Y_1$ is selected from CH and N.

In a further embodiment, $Y_1$ is N.

In a further embodiment, $Y_1$ is CH.

The following further embodiments apply to compounds of any one of formulae (I), (Ib) or (Ic), or the pharmaceutically acceptable salts thereof.

In another embodiment, $R_3$ is selected from hydrogen and halo.

In another embodiment, $R_4$ is selected from —$SF_5$ and —$Y_2$—$CF_2$—$Y_3$.

In a further embodiment, $R_4$ is chlorodifluoromethoxy.

In a further embodiment, $R_4$ is trifluoromethoxy.

In another embodiment, $R_6$ at each occurrence is independently selected from hydrogen, hydroxy, methyl, methoxy, cyano, trifluoromethyl, hydroxy-methyl, halo, amino, fluoro-ethyl, ethyl and cyclopropyl.

In a further embodiment, $R_6$, when linked to a nitrogen of the pyrazolyl ring, is selected from hydrogen, methyl, hydroxy-ethyl, fluoro-ethyl, ethyl and cyclopropyl.

In a further embodiment, $R_6$, when linked to a carbon atom of the pyrazolyl ring, is selected from hydrogen, hydroxy, methyl, methoxy, cyano, trifluoromethyl, hydroxy-methyl, halo, amino, fluoro-ethyl, ethyl and cyclopropyl.

In another embodiment, $R_7$ is selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyl)oxy, carboxy, methoxy-carbonyl, phosphonooxy, cyano and amino-carbonyl.

In another embodiment, $Y_2$ is selected from $CF_2$, O and $S(O)_{0-2}$.

In a further embodiment, $Y_2$ is O.

In a further embodiment, $Y_2$ is $CF_2$.

In a further embodiment, $Y_2$ is $S(O)_{0-2}$.

In another embodiment, $Y_3$ is selected from hydrogen, chloro, fluoro, methyl, difluoromethyl and trifluoromethyl.

In a further embodiment, $Y_3$ is chloro.

In a further embodiment, $Y_3$ is fluoro.

In a further embodiment are compounds, or the pharmaceutically acceptable salts thereof, selected from:

In another embodiment are compounds, or the pharmaceutically acceptable salts thereof, selected from:

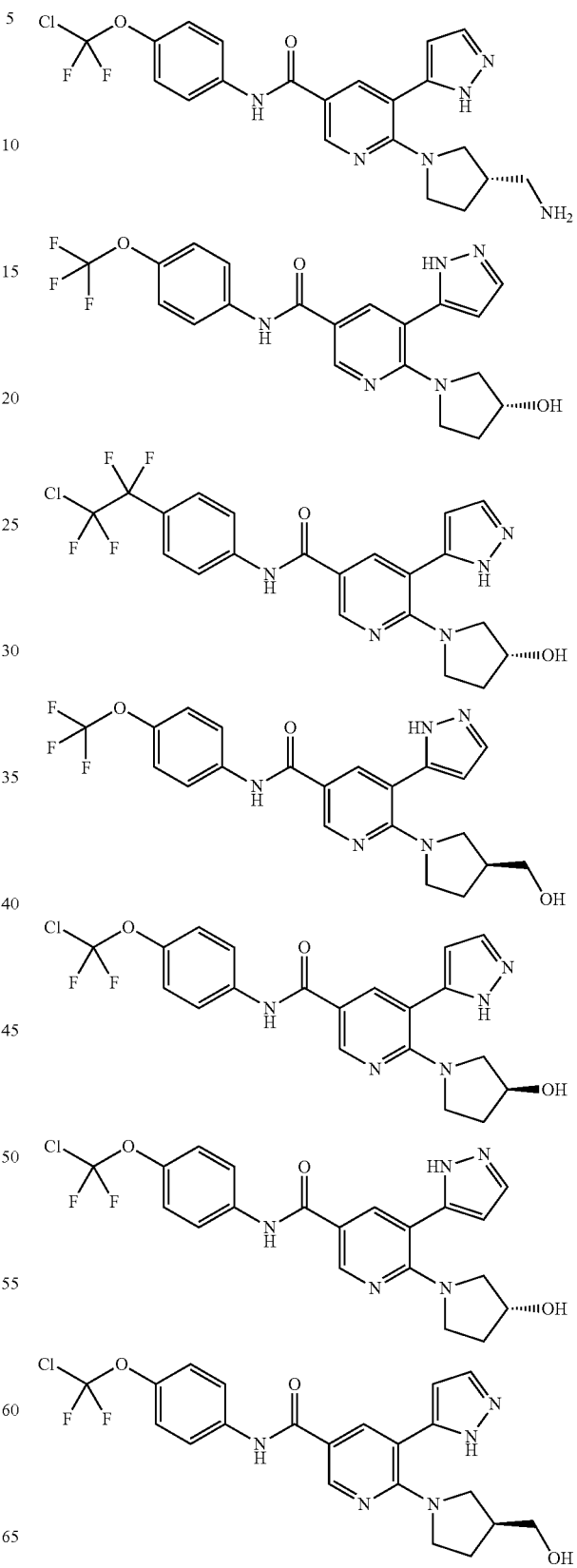

-continued
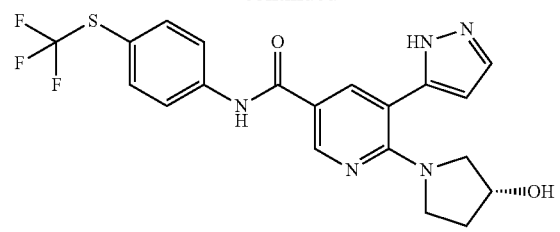
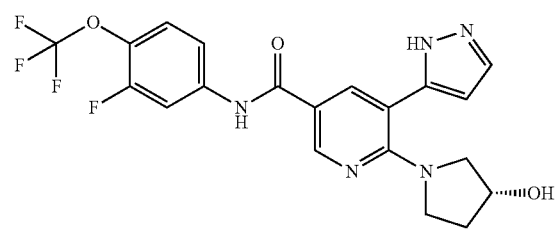
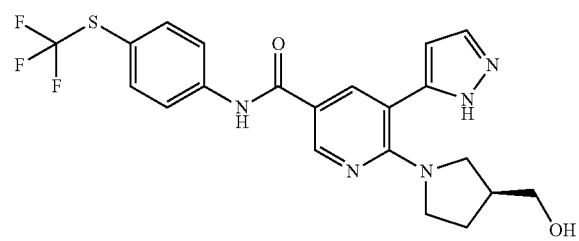
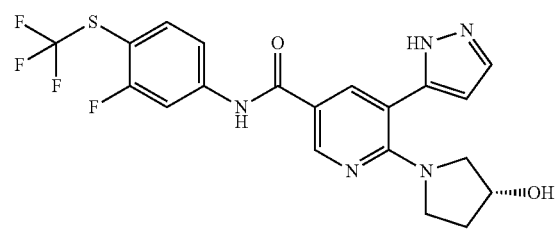
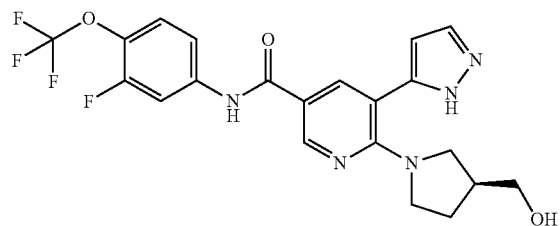
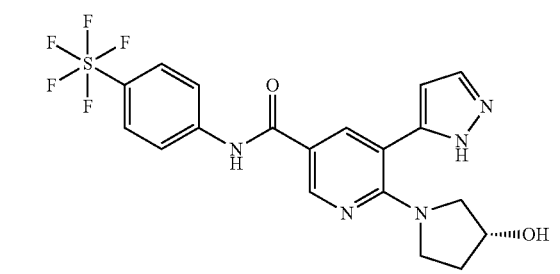
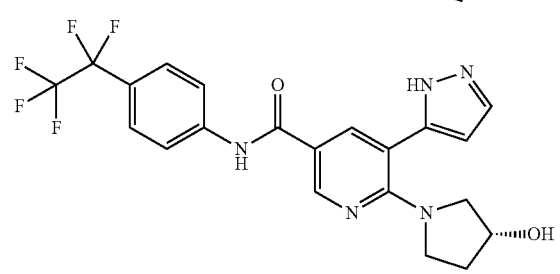
-continued
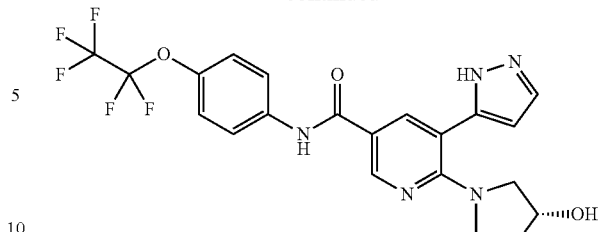
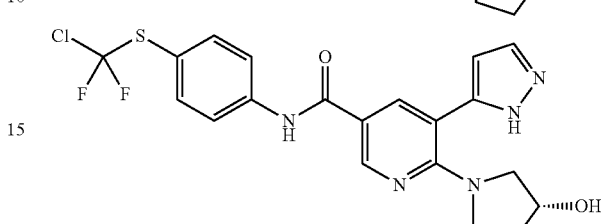
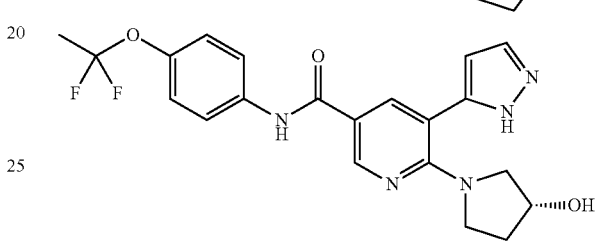
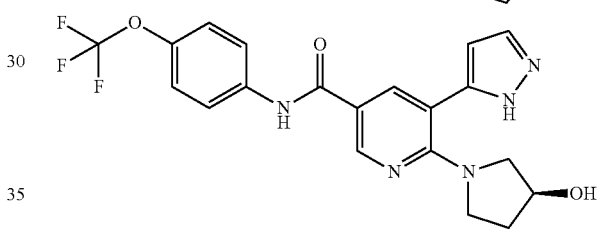
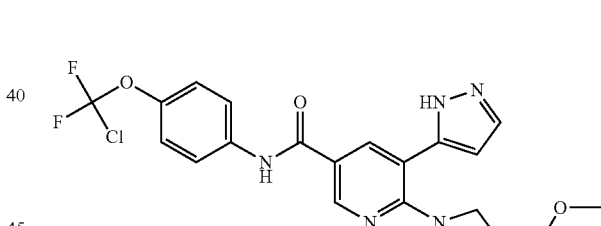
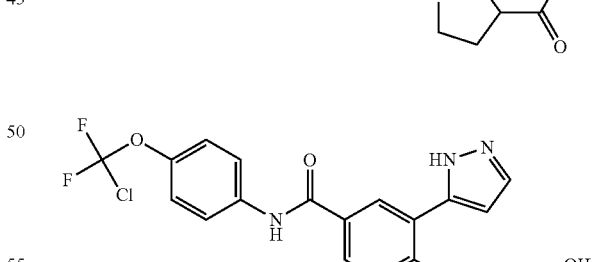
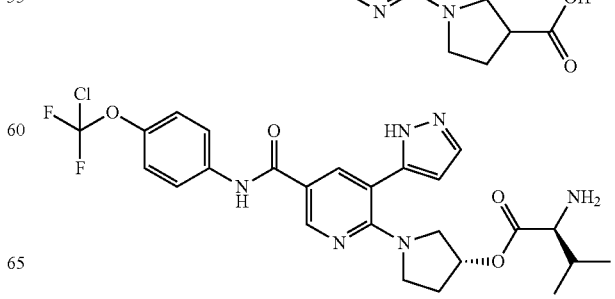

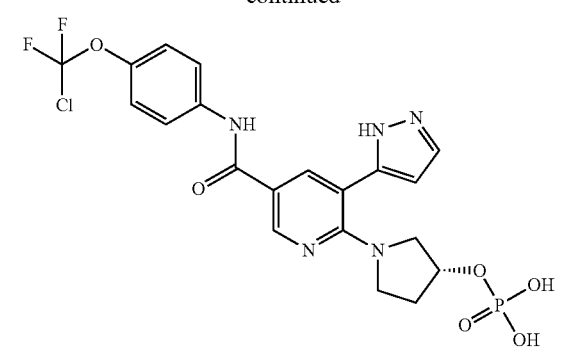
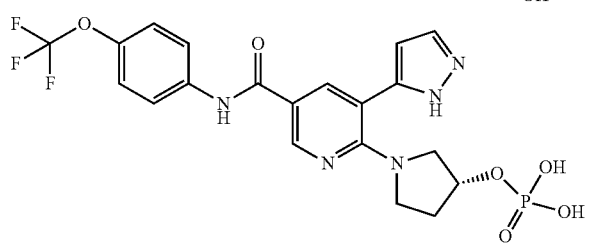
In another embodiment are compounds, or the pharmaceutically acceptable salts thereof, selected from:
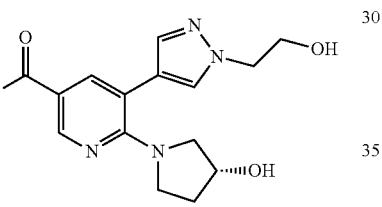
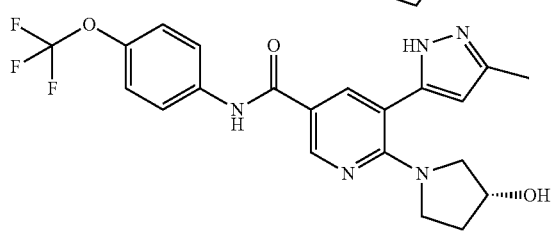
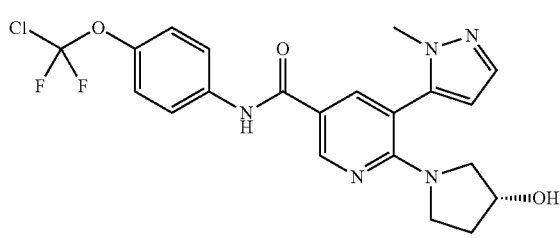
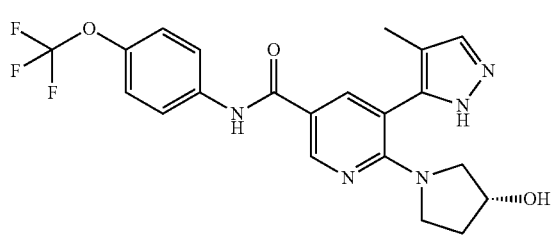
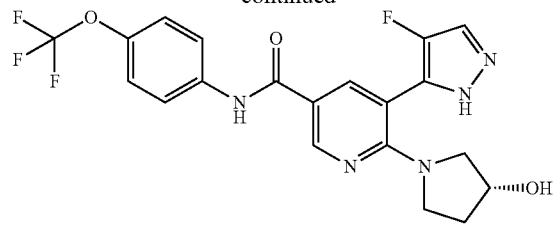
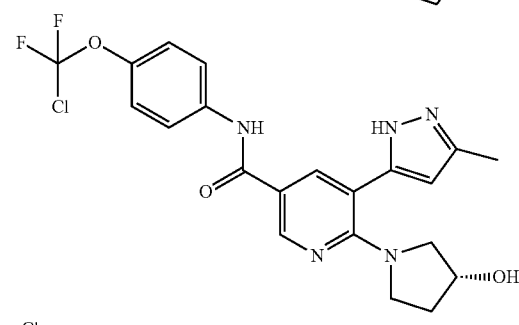
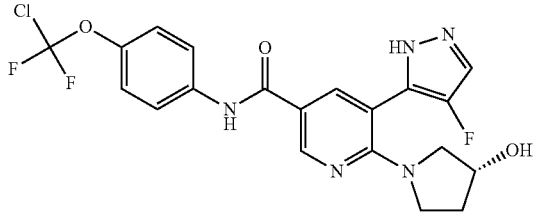
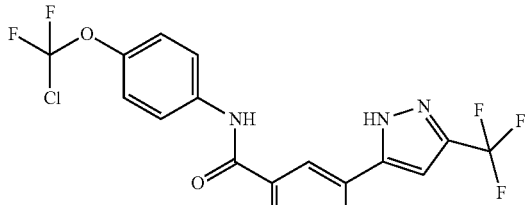
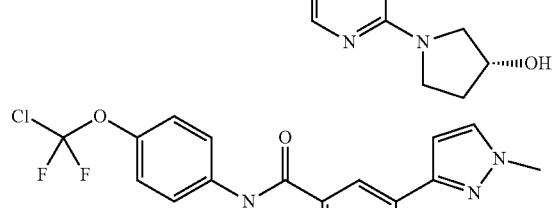
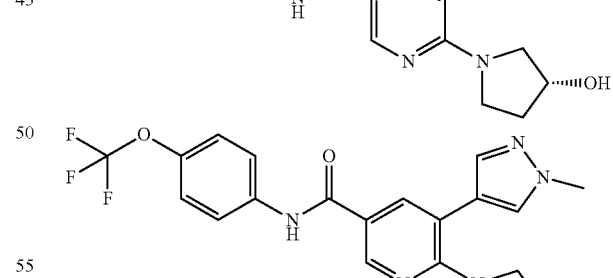
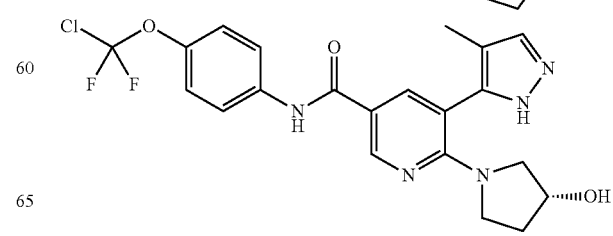

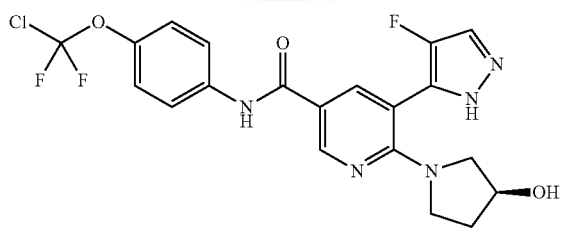

In another embodiment is a compound, or a pharmaceutically acceptable salt thereof, that is:

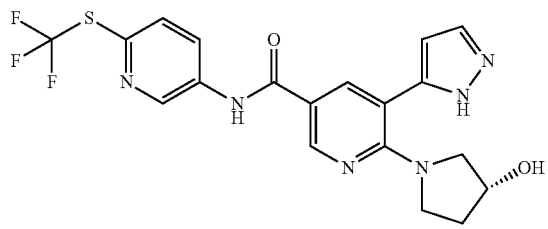 [SMILES: O=C(Nc1ccc(SC(F)(F)F)nc1)c1cnc(N2CC[C@@H](O)C2)c(-c2ccn[nH]2)c1]

In another embodiment are compounds selected from:

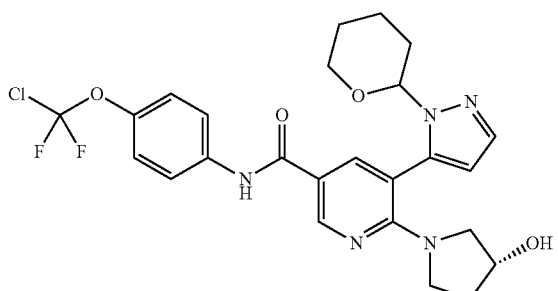

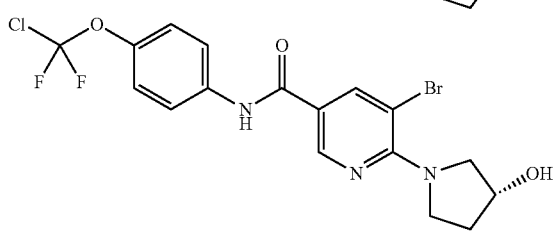

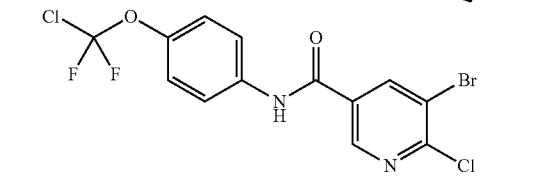

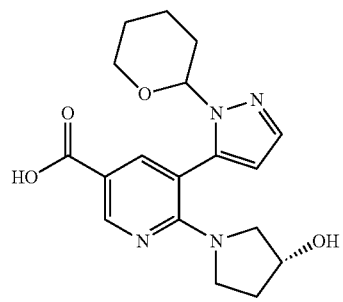

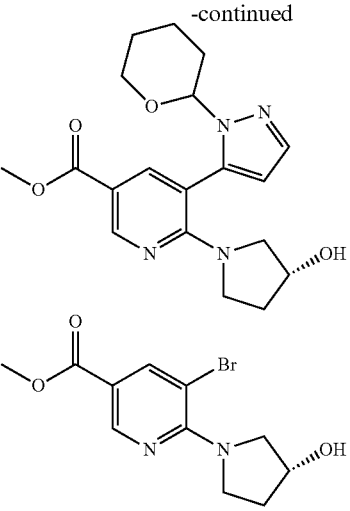

Pharmacology and Utility

On the basis of the inhibitory studies described in the "Assay" section below, a compound of formula (I) according to the invention shows therapeutic efficacy especially against disorders dependent on BCR-ABL1 activity. In particular, compounds of the present invention inhibit the allosteric or myristoyl binding site of BCR-ABL1 (including wild-type BCR-ABL1 and/or mutations thereof).

Combining an ATP-competitive inhibitor of BCR-ABL1 with an allosteric inhibitor of BCR-ABL1 delays acquired resistance in BCR-ABL1+KCL-22 cells, in vitro. Surprisingly, BCR-ABL1+KCL-22 cells treated every 3-4 days with a compound of the invention showed an acquired resistance after approximately 28 days whereas these same cells treated every 3-4 days with nilotinib or dasatinib showed an acquired resistance after only 18-21 days. Even more surprisingly, when BCR-ABL1+KCL-22 cells were treated every 3-4 days with a combination of a compound of the invention and either nilotinib or dasatinib, no acquired resistance was observed in at least the first 60 days. Therefore, myristoyl-binding site compounds of the present invention, in combination with BCR-ABL1 inhibitors that bind to the ATP binding site are especially important for the treatment of proliferative diseases involving upregulation of ABL1 kinase activity, as in the case of BCR-ABL1 fusion proteins in CML and subsets of other haematological malignancies such as ALL and AML.

Carcinoma cells utilize invapodia to degrade the extra cellular matrix during tumor invasion and metastasis. ABL kinase activity is required for SRC-induced invapodia formation, regulating distinct stages of invapodia assembly and function. The compounds of the invention, therefore, as inhibitors of ABL1, have the potential to be used as therapies for the treatment of metastatic invasive carcinomas.

An allosteric inhibitor of ABL1 kinase can be used to treat brain cancers: including Glioblastoma which is the most common & most aggressive malignant primary brain tumor in which the expression of ABL1 is immunohistochemically detectable in a subset of patients (Haberler C, Gelpi E, Marosi C, Rössler K, Birner P, Budka H, Hainfellner J A. Immunohistochemical analysis of platelet-derived growth factor receptor-alpha, -beta, c-KIT, ABL1, and ABL2 proteins in glioblastoma: possible implications for patient selection for imatinib mesylate therapy. J. Neurooncol. 2006 January; 76(2):105-9). However, clinical trials with Gleevec® failed in patients with glioblastoma (Reardon D A, Dresemann G, Taillibert S, Campone M, van den Bent M, Clement P, Blomquist E, Gordower L, Schultz H, Raizer J, Hau P, Easaw J, Gil M, Tonn J, Gijtenbeek A, Schlegel U, Bergstrom P, Green S, Weir A, Nikolova Z. Multicentre phase II studies evaluating imatinib plus hydroxyurea in patients with progressive glioblastoma. Br J. Cancer. 2009 Dec. 15; 101(12):1995-2004; Razis E, Selviaridis P, Labropoulos S, Norris J L, Zhu M J, Song D D, Kalebic T, Torrens M, Kalogera-Fountzila A, Karkavelas G, Karanastasi S, Fletcher J A, Fountzilas G. Phase II study of neoadjuvant imatinib in glioblastoma: evaluation of clinical and molecular effects of the treatment. Clin Cancer Res. 2009 Oct. 1; 15(19):6258-66; Dresemann G. Imatinib and hydroxyurea in pretreated progressive glioblastoma multiforme: a patient series. Ann Oncol. 2005 October; 16(10):1702-8), possibly because of the poor brain intratumoral exposure of the drug and in the absence of disturbed blood-brain barrier (Holdhoff et al, J. Neurooncol. 2010; 97(2):241-5). The transport of Gleevec® across the blood-brain barrier is in fact shown in preclinical studies to be limited by active efflux transporters such as P-glycoprotein. This is also the case for dasatinib (Chen Y, Agarwal S, Shaik N M, Chen C, Yang Z, Elmquist W F. P-glycoprotein and breast cancer resistance protein influence brain distribution of dasatinib. J Pharmacol Exp Ther. 2009 September; 330(3): 956-63). Irradiation is known to enhance the blood-brain barrier opening. In mouse models, glioblastoma multiforme response to Gleevec® correlated with an increase in tumor growth delay and survival when Gleevec® was administered in conjunction with daily irradiation (Geng L, Shinohara E T, Kim D, Tan J, Osusky K, Shyr Y, Hallahan D E. STI571 (Gleevec) improves tumor growth delay and survival in irradiated mouse models of glioblastoma. Int J Radiat Oncol Biol Phys. 2006 Jan. 1; 64(1):263-71). Therefore a new ABL1 inhibitor with high brain exposure represents a solid therapeutic approach for glioblastoma and other brain cancers.

CNS-CML: In some CML patients treated with Gleevec®, CNS Blast crisis and failure have been reported and can be explained by the poor brain exposure of Gleevec®. (Kim H J, Jung C W, Kim K, Ahn J S, Kim W S, Park K, Ko Y H, Kang W K, Park K. Isolated blast crisis in CNS in a patient with chronic myelogenous leukemia maintaining major cytogenetic response after imatinib. J Clin Oncol. 2006 Aug. 20; 24(24):4028-9; Radhika N, Minakshi M, Raj esh M, Manas B R, Deepak Kumar M. Central nervous system blast crisis in chronic myeloid leukemia on imatinib mesylate therapy: report of two cases. Indian J Hematol Blood Transfus. 2011 March; 27(1):51-4). In fact, in CML patients, Gleevec®'s concentration is in fact much lower (~100 fold) in the CNS than in plasma (Leis J F, Stepan D E, Curtin P T, Ford J M, Peng B, Schubach S, Druker B J, Maziarz R T. Central nervous system failure in patients with chronic myelogenous leukemia lymphoid blast crisis and Philadelphia chromosome positive acute lymphoblastic leukemia treated with imatinib (STI-571). Leuk Lymphoma. 2004 April; 45(4):695-8). Therefore, ABL1 inhibitors from the present invention which show a high brain exposure represent a valid approach for development of therapies against CML including CNS-CML.

Compounds of the invention can be useful in the treatment of viruses. For example, viral infections can be mediated by ABL1 kinase activity, as in the case of pox-viruses and the Ebola virus. Gleevec® and Tasigna® have been shown to stop the release of Ebola viral particles from infected cells, in vitro (Kalman, Daniel; Bornmann, William Gerard, Methods of use of non-ATP competitive tyrosine kinase inhibitors to treat pathogenic infection, PCT Int. Appl. 2007, WO 2007002441; Garcia Mayra; Cooper Arik; Shi Wei; Bornmann William; Carrion Ricardo; Kalman Daniel; Nabel Gary J. Productive Replication of Ebola Virus Is Regulated by the ABL1 Tyrosine Kinase. Science translational medicine 2012; 4:123ra24). Compounds of the present invention that inhibit ABL1 kinase, therefore, can be expected to reduce the pathogen's ability to replicate.

Compounds of the invention can also be useful in the treatment of neural degeneration. While native ABL1 tyrosine kinase remains relatively quiescent in healthy adult brain, it can be activated in the brain of patients with CNS diseases, including neurodegenerative diseases such as, Alzheimer's disease (AD), Parkinson's disease (AD), frontotemporal dementia (FTD), Picks disease, Niemann-Pick type C disease (NPC) and other degenerative, inflammatory and autoimmune diseases and ageing.

Parkinson's disease is the second most prevalent chronic neurodegenerative disease with the most common familial autosomal-recessive form being caused by mutations in the E3 ubiquitin ligase, parkin. Recent studies showed that activated ABL1/ABL2 was found in the striatum of patients with sporadic Parkinson's disease. Concomitantly, parkin was tyrosine-phosphorylated, causing loss of its ubiquitin ligase and cytoprotective activities as indicated by the accumulation of parkin substrates (Ko H S, Lee Y, Shin J H, Karuppagounder S S, Gadad B S, Koleske A J, Pletnikova O, Troncoso J C, Dawson V L, Dawson T M. Phosphorylation by the c-Abl protein tyrosine kinase inhibits parkin'subiquitination and protective function. Proc Natl Acad Sci USA. 2010 Sep. 21; 107(38):16691-6; Imam S Z, Zhou Q, Yamamoto A, Valente A J, Ali S F, Bains M, Roberts J L, Kahle P J, Clark R A, Li S, Novel regulation of parkin function through c-Abl-mediated tyrosine phosphorylation: implications for Parkinson's disease. J. Neurosci. 2011 Jan. 5; 31(1):157-63). These two studies also showed that in cell or animal models of Parkinson's disease, pharmacological inhibition of ABL1 kinase or genetic ABL1 knockdown prevented tyrosine phosphorylation of parkin and restored its E3 ligase activity and cytoprotective function both in vitro and in vivo. These results indicate that ABL1-dependent tyrosine phosphorylation of parkin is a major post-translational modification that leads to loss of parkin function and disease progression in sporadic PD. Therefore, the ability of compounds of the invention to inhibit the myristate-binding site of ABL1, can be expected to offer new therapeutic opportunities for blocking the progression of Parkinson's disease.

Alzheimer's disease is characterized by two main hallmarks: extracellular deposits of the neurotoxic amyloid-β which leads to amyloid plaque development, and intracellular accumulation of hyperphosphorylated tau which contributes to the development of neurofibrillary tangles (NFTs).

Amyloid-β level is reduced following intrathecal treatment with Gleevec® in the brain of wild-type guinea-pigs and in cell models (Netzer W J, Dou F, Cai D, Veach D, Jean S, Li Y, Bornmann W G, Clarkson B, Xu H, Greengard P. Gleevec inhibits beta-amyloid production but not Notch cleavage. Proc Natl Acad Sci USA. 2003 Oct. 14; 100(21):12444-9). The same group proposed that Gleevec® achieves its amyloid-β-lowering effect via a new mechanism preventing GSAP interaction with the gamma-secretase substrate, APP-CTF (He G, Luo W, Li P, Remmers C, Netzer W J, Hendrick J, Bettayeb K, Flajolet M, Gorelick F, Wennogle L P, Greengard P. Gamma-secretase activating protein is a therapeutic target for Alzheimer's disease. Nature. 2010 Sep. 2; 467 (7311):95-8). In this study, GleevecO's effect to inhibit GSAP/APP-CTF was only seen at micromolar concentrations. Another group showed that tyrosine phosphorylation of the intracellular domain of APP (i.e. Tyr682) regulates the amyloidogenic APP processing accelerating amyloid-β formation in vivo (Barbagallo A P, Weldon R, Tamayev R, Zhou D, Giliberto L, Foreman O, D'Adamio L. Tyr(682) in the intracellular domain of APP regulates amyloidogenic APP processing in vivo. PLoS One. 2010 Nov. 16; 5(11):e15503). Other studies showed that APP is tyrosine-phosphorylated in cells expressing a constitutively active form of the ABL1 oncogene (Zambrano N, Bruni P, Minopoli G, Mosca R, Molino D, Russo C, Schettini G, Sudol M, Russo T. The beta-amyloid precursor protein APP is tyrosine-phosphorylated in cells expressing a constitutively active form of the Abl protoncogene. J Biol. Chem. 2001 Jun. 8; 276(23):19787-92). These data together suggest an ABL1-dependent amyloidogenic APP processing for the formation of the toxic amyloid-β peptide and subsequent amyloid plaques. Therefore an-ABL1 inhibitor would be expected to lower amyloid plaque formation in Alzheimmer's patients.

Tau has been shown to be phosphorylated by ABL1 kinase at tyrosines 18, 197, 310, and 394 in cell models, and tau pY394 has been shown to be present in the lesions NFTs in the brain of AD patients.

ABL1 is activated in the brain of patients with sporadic Alzheimer's disease as shown by its phosphorylation either at Y412, an indicator of activation, which co-localizes ganulovacuolar degeneration, or at T735 which co-localized with the typical lesions, amyloid plaques, neurofibrillary tangles (NFTs) in addition to GVD. Amyloid-3 and oxidative stress activate ABL1 kinase in neuronal cultures and intracerebral injection of fibrillar amyloid peptide leads to increased expression of ABL1 and a downstream effector p73. Transgenic mice (APP/Swe mouse model of AD), showed higher levels of ABL1 in their brain and, when these mice were treated with the ABL1 inhibitor Gleevec®, tau phosphorylation was decreased in their brains. A transgenic mouse model expressing constitutively active ABL1 in forebrain neurons exhibited neuronal loss, severe neuroinflammation, and tyrosine phosphorylation of tau in the brain (For review, see Schlatterer S D, Acker C M, Davies P. c-Abl in neurodegenerative disease. J Mol. Neurosci. 2011 November; 45(3):445-52).

Based on all these results, evidence exists for a role for ABL1 kinase in Alzheimer's pathogenesis for development of both lesions, amyloid plaques and neurofibrillary tangles.

Further, activated ABL1 is also present in other tauopathies besides sporadic Alzheimer's including in the brain of patients with frontotemporal dementia with N279K and P301L mutations, Pick's disease, and Guam Parkinson-dementia (Schlatterer S D, Acker C M, Davies P. c-Abl in neurodegenerative disease. J Mol. Neurosci. 2011 November; 45(3):445-52).

Therefore, compounds of the present invention, by inhibiting ABL1 in the CNS, represent a valid approach for development of therapies against Alzheimer's disease, as well as other β-amyloidoses, such as vascular dementia and other tauopathies, such as frontotemporal dementia and picks disease.

Niemann-Pick type C (NPC) disease is a fatal autosomal recessive disorder characterized by the accumulation of free cholesterol and glycosphingolipids in the endosomal-lysosomal system, and by a progressive neuronal death in particular of cerebellar Purkinje neurons. In a mouse model of NPC, the proapoptotic ABL1, the downstream target as well as p73 target genes are expressed in the cerebellums. Inhibition of ABL1 with Gleevec® prevented from loss of Purkinje neurons, improved neurological symptoms, and increased the survival. This prosurvival effect of Gleevec® correlated with reduced mRNA levels of p73 proapoptotic target genes (Alvarez A R, Klein A, Castro J, Cancino G I, Amigo J, Mosqueira M, Vargas L M, Yévenes L F, Bronfman F C, Zanlungo S. Imatinib therapy blocks cerebellar apoptosis and improves neurological symptoms in a mouse model of Niemann-Pick type C disease. FASEB J. 2008 October; 22(10):3617-27). Therefore, compounds of the present invention, by inhibiting ABL1 kinase, represent a valid approach for the development of therapies against diseases caused by the proapoptotic ABL1/p73 pathway, such as NPC.

In prion disease models, Gleevec® showed beneficial effects: It delayed prion neuroinvasion by inhibiting prion propagation from the periphery to the CNS (Yun S W, Ertmer A, Flechsig E, Gilch S, Riederer P, Gerlach M, Schätzl H M, Klein M A. The tyrosine kinase inhibitor imatinib mesylate delays prion neuroinvasion by inhibiting prion propagation in the periphery. J. Neurovirol. 2007 August; 13(4):328-37). Gleevec® and ABL1 deficiency induced cellular clearance of PrPSc in prion-infected cells (Ertmer A, Gilch S, Yun S W, Flechsig E, Klebl B, Stein-Gerlach M, Klein M A, Schätzl H M. The tyrosine kinase inhibitor STI571 induces cellular clearance of PrPSc in prion-infected cells. J Biol. Chem. 2004 Oct. 1; 279(40):41918-27). Therefore, novel ABL1 inhibitors from the present invention also represent a valid therapeutic approach for the treatment of prion diseases such as Creutzfeldt-Jacob disease.

X-linked recessive Emery-Dreifuss muscular dystrophy is caused by mutations of emerin, a nuclear-membrane protein with roles in nuclear architecture, gene regulation and signaling. A recent study has shown that emerin is tyrosine-phosphorylated directly by ABL1 in cell models, and that the phosphorylation status of emerin changes emerin binding to other proteins such as BAF. This, in turn, may explain the mislocalization of mutant emerin from nuclear to cytosolic compartments and consequently changes in downstream effector and signal integrator for signaling pathway(s) at the nuclear envelope (Tifft K E, Bradbury K A, Wilson K L. Tyrosine phosphorylation of nuclear-membrane protein emerin by SRC, ABL1 and other kinases. J Cell Sci. 2009 Oct. 15; 122(Pt 20):3780-90). Changes in emerin-lamin interactions during both mitosis and interphase are of relevance for the pathology of muscular dystrophies. In addition, results from another study demonstrate that Gleevec® attenuates skeletal muscle dystrophy in mdx mice (Huang P, Zhao X S, Fields M, Ransohoff R M, Zhou L. Imatinib attenuates skeletal muscle dystrophy in mdx mice. FASEB J. 2009 August; 23(8):2539-48).

Therefore, novel ABL1 inhibitors from the present invention also represent therapeutic approaches for treatment of skeletal and muscular dystrophies.

Furthermore, ABL1 kinase plays a role in inflammation and oxidative stress, two mechanisms that are implicated in a variety of human diseases ranging from acute CNS diseases, such as stroke and traumatic brain or spinal cord injuries, chronic CNS diseases, such as Alzheimer's, Parkinson's, Huntington's and motoneuron diseases, to non-CNS inflammatory and autoimmune diseases, such as diabetes, pulmonary fibrosis.

For example, Gleevec® prevents fibrosis in different preclinical models of systemic sclerosis and induces regression of established fibrosis (Akhmetshina A, Venalis P, Dees C, Busch N, Zwerina J, Schett G, Distler O, Distler J H. Treatment with imatinib prevents fibrosis in different preclinical models of systemic sclerosis and induces regression of established fibrosis. Arthritis Rheum. 2009 January; 60(1):219-24) and it shows antifibrotic effects in bleomycin-induced pulmonary fibrosis in mice (Aono Y, Nishioka Y, Inayama M, Ugai M, Kishi J, Uehara H, Izumi K, Sone S. Imatinib as a novel antifibrotic agent in bleomycin-induced pulmonary fibrosis in mice. Am J Respir Crit. Care Med. 2005 Jun. 1;

171(11):1279-85). Another study showed that both imatinib and nilotinib attenuated bleomycin-induced acute lung injury and pulmonary fibrosis in mice (Rhee C K, Lee S H, Yoon H K, Kim S C, Lee S Y, Kwon S S, Kim Y K, Kim K H, Kim T J, Kim J W. Effect of nilotinib on bleomycin-induced acute lung injury and pulmonary fibrosis in mice. Respiration. 2011; 82(3):273-87). Although in these studies the authors were focusing on the implication the mechanism related to PDGFRs, of interest, in the study by Rhee et al. (Respiration. 2011; 82(3):273-87), nilotinib which is a more potent c-ABL inhibitor than imatinib showed superior therapeutic antifibrotic effects, thus supporting the therapeutic applicability of c-ABL inhibitors for treatment of human diseases with pulmonary inflammation. In another study, exposure of mice to hyperoxia increased ABL1 activation which is required for dynamin 2 phosphorylation and reactive oxygen species production and pulmonary leak (Singleton P A, Pendyala S, Gorshkova I A, Mambetsariev N, Moitra J, Garcia J G, Natarajan V. Dynamin 2 and c-Abl are novel regulators of hyperoxia-mediated NADPH oxidase activation and reactive oxygen species production in caveolin-enriched microdomains of the endothelium. J Biol. Chem. 2009 Dec. 11; 284(50): 34964-75).

Therefore, these data indicate that new c-ABL inhibitors from the present invention have therapeutic applicability for treatment of human diseases with pulmonary inflammation.

ABL1 activation by insulin, via a modification of FAK response, may play an important role in directing mitogenic versus metabolic insulin receptor signaling (Genua M, Pandini G, Cassarino M F, Messina R L, Frasca F. c-Abl and insulin receptor signalling. Vitam Horm. 2009; 80:77-105). c-Abl inhibitors such as Gleevec® have been shown to reverse type 1 diabetes in nonobese diabetic mice (Louvet C, Szot G L, Lang J, Lee M R, Martinier N, Bollag G, Zhu S, Weiss A, Bluestone J A. Tyrosine kinase inhibitors reverse type 1 diabetes in nonobese diabetic mice. Proc Natl Acad Sci USA. 2008 Dec. 2; 105(48):18895-900). Amelioration of diabetes by Gleevec® was mimicked by siRNA-mediated knockdown of ABL1 mRNA (Hagerkvist R, Sandler S, Mokhtari D, Welsh N. Amelioration of diabetes by imatinib mesylate (Gleevec): role of beta-cell NF-kappaB activation and anti-apoptotic preconditioning. FASEB J. 2007 February; 21(2):618-28).

Therefore, the new ABL1 inhibitors from the present invention have therapeutic applicability for treatment of human diabetes.

An ABL1 inhibitor from the present invention can be used in combination with one or more of the existing treatment for the above diseases: for example an ABL1 inhibitor from the present invention can be used in combination with Levodopa or other L-DOPA-containing medicaments or a dopamine agonist for the treatment of Parkinson's disease or in combination with a cholinesterase inhibitor such as Exelon capsule or transdermal patch for the treatment of Alzheimer's disease.

In chronic myelogeous leukemia (CML), a reciprocal balanced chromosomal translocation in hematopoietic stem cells (HSCs) produces the BCR-ABL1 hybrid gene. The latter encodes the oncogenic BCR-ABL1 fusion protein. Whereas ABL1 encodes a tightly regulated protein tyrosine kinase, which plays a fundamental role in regulating cell proliferation, adherence and apoptosis, the BCR-ABL1 fusion gene encodes as constitutively activated kinase. This activated kinase transforms HSCs to produce a phenotype exhibiting deregulated clonal proliferation, reduced capacity to adhere to the bone marrow stroma and a reduced apoptotic response to mutagenic stimuli, resulting in progressively more malignant transformations. The resulting granulocytes fail to develop into mature lymphocytes and are released into the circulation, leading to a deficiency in the mature cells and increased susceptibility to infection. ATP-competitive inhibitors of BCR-ABL1 have been demonstrated to prevent the kinase from activating mitogenic and anti-apoptotic pathways (for example, PI-3 kinase and STATS), leading to the death of the BCR-ABL1 phenotype cells and thereby providing an effective therapy against CML. The KCL-22 cell line (purchased from DSMZ, Leibniz Institute, Germany) is established from the pleural effusion of a 32-year old woman with Philadelphia chromosome-positive CML in blast crisis in 1981, and has been described to contain the t(9;22) leading to BCR-ABL1 fusion gene and a p53 mutation. KCL-22 cell lines can be used in Xenograft models to show in vivo efficacy of compounds of the invention (see Assay section, infra). The compounds of the invention, as BCR-ABL1 inhibitors, including mutants thereof, are thus especially appropriate for the therapy of diseases related to its over-expression, such as ALL or CML leukemias.

Compounds of the invention have also been demonstrated to have anti-tumor activity, in vitro: The in vitro antitumor activity is tested, for example using leukemic cell lines such as Ba/F3-BCR-ABL1, KCL-22, K-562, MEG-01, KYO-1, LAMA-84, KU812, EM-2, CML-T1, BV-173, or ALL-SIL.

The present invention includes a method to treat cancer, comprising administering to a subject in need of such treatment an effective amount of a compound of the invention or a pharmaceutical composition.

A further embodiment comprises administering to the subject an additional therapeutic agent.

In a further embodiment, the additional therapeutic agent is a different BCR-ABL1 inhibitor selected from imatinib, nilotinib, dasatinib, dosutinib, radotinib, ponatinib and bafetinib.

In another embodiment is a method to treat a condition mediated by BCR-ABL1, comprising administering to a subject in need thereof an effective amount of a compound of the invention or a pharmaceutical composition.

BCR-ABL1 can contain one or more mutations. These mutations include V299L, T315I, F317I, F317L, Y253F, Y253H, E255K, E255V, F359C and F359V (UJane F. Apperley. Part 1: Mechanism of resistance to imatinib in chronic myeloid leukaemia. Lancet Oncology 2007; 8:1018).

In a further embodiment is a method to treat a condition mediated by the BCR-ABL1, where the BCR-ABL1 contains one or more mutations selected from V299L, T315I, F317I, F317L, Y253F, Y253H, E255K, E255V, F359C and F359V.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an ABL1/BCR-ABL1-mediated disorder, comprising the step of: administering to a patient in need thereof a therapeutically effective amount of a chemotherapeutic agent in combination with a therapeutically effective amount of a compound of formula (I).

In another aspect is a compound of formula I, or any specific embodiments thereof described above, for use in the treatment of cancer.

In a further aspect, the cancer is leukemia selected from chronic myeloid leukemia (CML) and acute lymphoblastic leukemia (ALL).

In another aspect is a compound of formula I or any specific embodiments thereof for use in the treatment of cancer in combination with an additional compound selected from imatinib, nilotinib, dasatinib, bosutinib, ponatinib and bafetinib.

In a further aspect, the compound of formula I is (R)—N-(4-(Chlorodifluoromethoxy)phenyl)-6-(3-hydroxypyrrolidin-1-yl)-5-(1H-pyrazol-5-yl)nicotinamide.

In a further aspect the compound of formula I is a pharmaceutically acceptable salt of (R)—N-(4-(Chlorodifluoromethoxy)phenyl)-6-(3-hydroxypyrrolidin-1-yl)-5-(1H-pyrazol-5-yl)nicotinamide.

In a further aspect, the additional compound is administered sequentially.

In a further aspect, the additional compound is administered simultaneously.

In a further aspect, the additional compound is nilotinib.
In a further aspect, the additional compound is imatinib.
In a further aspect, the additional compound is dasatinib.
In a further aspect, the additional compound is bosutinib.
In a further aspect, the additional compound is ponatinib.
In a further aspect, the additional compound is bafetinib.

In another aspect, the present invention relates to a method of treating a ABL1/BCR-ABL1-mediated disorder, comprising the step of: administering to a patient in need thereof a therapeutically effective amount of a chemothereutic agent in combination with a therapeutically effective amount of a compound of formula (I).

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution, suspension or solid dispersion in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

A solid dispersion formulation of the invention comprises, for example, an amorphous dispersion of a compound of the invention, an excipient (copolymers, such as the polyvinyl pyrrolidinone (PVP) VA64 (Kollidon® VA64 or Copovidone), and the like). The solid dispersion can further be enhanced with low viscosity hydroxylpropyl methyl celluloses (HPMCs) (such as Pharmacoat 603, Methocel E3, or the like). See Example 41, below, for more specific details for the preparation of a solid dispersion formulation of the invention.

In one embodiment of the invention is a pharmaceutical composition comprising an amorphous dispersion of (R)—N-(4-(chlorodifluoromethoxy)phenyl)-6-(3-hydroxypyrrolidin-1-yl)-5-(1H-pyrazol-5-yl)nicotinamide (Example 9) and 1 to 2 excipients; wherein the excipient is selected from HPMC AS, Pharmacoat 603, Eudragit L100, PVP K30, PVP VA64 and Eudragit EPO.

In a further embodiment, the excipients are PVP VA64 and Pharmacoat 603.

In a further embodiment, the percentage of Pharmacoat 603 is in the range of 30% to 45%, the percentage of PVP VA64 is in the range of 30% to 45% and the percentage of (R)—N-(4-(chlorodifluoromethoxy)phenyl)-6-(3-hydroxypyrrolidin-1-yl)-5-(1H-pyrazol-5-yl)nicotinamide (Example 9) is in the range of 20% to 30%.

In a further embodiment, the percentage of Pharmacoat 603 is 37.5%, the percentage of PVP VA64 is 37.5% and the percentage of (R)—N-(4-(chlorodifluoromethoxy)phenyl)-6-(3-hydroxypyrrolidin-1-yl)-5-(1H-pyrazol-5-yl)nicotinamide (Example 9) is 25%.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

In vivo PK parameters can be utilized for the estimation of human PK parameters. Applying various methods known in the art for prediction of human PK, the predicted human clearance can be estimated. For example, (R)—N-(4-(Chlorodifluoromethoxy)phenyl)-6-(3-hydroxypyrrolidin-1-yl)-5-(1H-pyrazol-5-yl)nicotinamide (Example 9) was estimated to be 3 mL/min/kg and volume of distribution was estimated to be 1 L/kg. The projected human efficacious daily dose for Example 9 was, therefore, estimated to be between 90 and 130 mg/day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17-beta-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposomes internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula (I) (or a pharmaceutical composition comprising a compound of the formula (I) in the treatment of one or more of the diseases mentioned herein; wherein the response to treatment is beneficial as demonstrated, for example, by the partial or complete removal of one or more of the symptoms of the disease up to complete cure or remission.

Philadelphia chromosome positive (Ph+) ALL accounts for 15-30% of adult ALL and up to 5% of pediatric ALL (Faderl S, Garcia-MAnero G, Thomas D, et al. Philadelphia Chromosome Positive Acute Lymphoblastic Leukemia—Current Concepts and Future Perspectives. Rev Clin Exp Hematol 2002; 6:142-160). Pediatric Ph+ ALL is characterized by an older age (median 9-10 years versus approximately 4 years for all ALL patients) and higher WBC counts at diagnosis. In both adults and children, Ph+ ALL is characterized by a reciprocal translocation between chromosomes 9 and 22 (t(9;22)(q34;q11)) resulting in fusion of the BCR gene on chromosome 22 with ABL gene sequences translocated from chromosome 9, resulting in expression of the BCR-ABL1 protein. There are 2 primary variants of BCR-ABL1, p190BCR-ABL1, detectable in approximately 85% of Ph+ ALL patients, and p210 BCR-ABL1, typical of CML, identified in approximately 15% of Ph+ ALL patients (Dombret H, Galbert J, Boiron J, et al. Outcome of Treatment in Adults with Philadelphia chromosome-posititve acute lymphoblastic leukemia—Results of the prospective multicenter LALA-94 trial. Blood 2002; 100:2357-2366; Faderl S, Garcia-MAnero G, Thomas D, et al. Philadelphia Chromosome Positive Acute Lymphoblastic Leukemia—Current Concepts and Future Perspectives. Rev Clin Exp Hematol 2002; 6:142-160).

The treatment of ALL is based on each patient's risk classification, with increasingly intensive treatment for patients who are at higher risk of relapse; this strategy maximizes remission rates while limiting unnecessary toxicities.

Progress has been incremental, from the introduction of combination chemotherapy and treatment for pre-symptomatic central nervous system leukemia to newer, intensive treatment regimens for patients at high risk for relapse (C. H. Pui and W. E. Evans. Acute Lymphoblastic Leukemia New Engl J Med 1998; 339:605-615;). Prior to the development of imatinib, Ph+ ALL patients were treated with intensive chemotherapy followed by hematopoietic stem cell transplant (HSCT), ideally with a matched related donor, as this was shown to result in improved EFS versus either HSCT with other donors or chemotherapy alone. Overall, and in contrast to the majority of pediatric patients with ALL, patients with Ph+ ALL have had a dire prognosis with low rates of event free survival (EFS) (Arico M, Valsecchi M G, Camitta B, Schrappe M, Chessells J, Baruchel A, Gaynon P, Silverman L, Janka-Schaub G, Kamps W, et al. New Engl J Med 2000; 342:998-1006).

Existing therapies (such as GLEEVEC®, TASIGNA®, SPRYCEL®, BOSULIF®, ICLUSIG™ and the like) bind to the ATP binding site of the kinase domain. In contrast, compounds of the invention are potent BCR-ABL1, ABL1 and ABL2 inhibitors that bind to a site on the kinase domain that is distinct from the ATP-binding site.

Therefore, compounds of the invention with their novel, allosteric mechanism of action, can be used as a stand-alone therapy or can be used sequentially or in combination with existing therapies selected from GLEEVEC®, TASIGNA®, SPRYCEL®, BOSULIF® and ICLUSIG™.

As a stand-alone therapy, compounds of the invention can be used to treat BCR-ABL1, ABL1 and ABL2 related diseases and disorders. BCR-ABL1 can be wild-type or a mutant BCR-ABL1 selected from V299L, T315I, F317I/L, Y253F/H, E255K/V, and F359C/V. Compounds of the invention could be used to treat patients who do not respond to existing therapies as a result of mutations arising in the ATP-binding site. As a combination therapy, compounds of the invention present a unique opportunity to treat patients with Ph+ leukemia using a combination of two potent, mechanistically distinct BCR-ABL inhibitors. The combination approach in the clinic could provide patients with a deeper and more sustained reduction in tumor burden with a reduced risk of relapse.

In another embodiment of the invention is a method for treating a warm-blooded animal having a leukemia selected from chronic myeloid leukemia (CML) and acute lymphoblastic leukemia (ALL) comprising administering to said animal a therapeutically effective amount of a compound of the invention or a pharmaceutically acceptable salt thereof.

In a further embodiment, the warm blooded animal is a human (patient).

In a further embodiment the compound of the invention is (R)—N-(4-(chlorodifluoromethoxy)phenyl)-6-(3-hydroxypyrrolidin-1-yl)-5-(1H-pyrazol-5-yl)nicotinamide (Example 9) or a pharmaceutically acceptable salt thereof.

In another embodiment of the invention is a method for treating a warm-blooded animal having a leukemia selected from chronic myeloid leukemia (CML) and acute lymphoblastic leukemia (ALL) comprising administering to said animal a sequential administration of a therapeutically effective amount of a compound of the invention or a pharmaceutically acceptable salt thereof and therapeutically effective amount of a compound selected from imatinib, nilotinib, dasatinib, bosutinib, ponatinib and bafetinib.

In a further embodiment, the warm blooded animal is human (patient).

In a further embodiment the compound of the invention is (R)—N-(4-(chlorodifluoromethoxy)phenyl)-6-(3-hydroxypyrrolidin-1-yl)-5-(1H-pyrazol-5-yl)nicotinamide (Example 9) or a pharmaceutically acceptable salt thereof.

In a further embodiment, the dose of (R)—N-(4-(chlorodifluoromethoxy)phenyl)-6-(3-hydroxypyrrolidin-1-yl)-5-(1H-pyrazol-5-yl)nicotinamide (Example 9) is 90-130 mg.

In a further embodiment, the dose of nilotinib is 10-50 mg/kg, Imatinib is 50-200 mg/kg, dasatinib is 5-20 mg/kg or ponatinib is 2-10 mg/kg.

In a further embodiment, the dose of bosutinib is 500 mg.

In another embodiment of the invention is a method for treating a warm-blooded animal having a leukemia selected from chronic myeloid leukemia (CML) and acute lymphoblastic leukemia (ALL) comprising administering to said animal a simultaneous administration of a therapeutically effective amount of a compound of the invention or a pharmaceutically acceptable salt thereof and therapeutically effective amount of a compound selected from imatinib, nilotinib, dasatinib, bosutinib, ponatinib and bafetinib.

In a further embodiment, the warm blooded animal is a human (patient).

In a further embodiment the compound of the invention is (R)—N-(4-(chlorodifluoromethoxy)phenyl)-6-(3-hydroxypyrrolidin-1-yl)-5-(1H-pyrazol-5-yl)nicotinamide (Example 9) or a pharmaceutically acceptable salt thereof.

In a further embodiment, the dose of (R)—N-(4-(chlorodifluoromethoxy)phenyl)-6-(3-hydroxypyrrolidin-1-yl)-5-(1H-pyrazol-5-yl)nicotinamide (Example 9) is 90-130 mg.

In a further embodiment, the dose of nilotinib is 10-50 mg/kg, Imatinib is 50-200 mg/kg, dasatinib is 5-20 mg/kg or ponatinib is 2-10 mg/kg.

In a further embodiment, the dose of bosutinib is 500 mg.

In another embodiment of the invention is a method for treating a warm-blooded animal having a leukemia selected from chronic myeloid leukemia (CML) and acute lymphoblastic leukemia (ALL) comprising administering to said animal a simultaneous administration of a therapeutically effective amount of a (R)—N-(4-(chlorodifluoromethoxy)phenyl)-6-(3-hydroxypyrrolidin-1-yl)-5-(1H-pyrazol-5-yl)nicotinamide (Example 9) or a pharmaceutically acceptable salt thereof and therapeutically effective amount of Nilotinib.

In another embodiment of the invention is a method for treating a warm-blooded animal having a leukemia selected from chronic myeloid leukemia (CML) and acute lymphoblastic leukemia (ALL) comprising administering to said animal a simultaneous administration of a therapeutically effective amount of a (R)—N-(4-(chlorodifluoromethoxy)phenyl)-6-(3-hydroxypyrrolidin-1-yl)-5-(1H-pyrazol-5-yl)nicotinamide (Example 9) or a pharmaceutically acceptable salt thereof and therapeutically effective amount of Nilotinib.

A compound of formula (I) can also be used in combination with other antineoplastic compounds. Such compounds include, but are not limited to ribonucleotide reductase inhibitors, topoisomerase I inhibitors; JAK inhibitors, such as ruxolitinib; smoothened inhibitors, such as LDE225; interferon; topoisomerase II inhibitors; microtubule active compounds; alkylating compounds; histone deacetylase inhibitors; mTOR inhibitors, such as RAD001; antineoplastic antimetabolites; platin compounds; compounds targeting/decreasing a protein or lipid kinase activity methionine aminopeptidase inhibitors; biological response modifiers; inhibitors of Ras oncogenic isoforms; telomerase inhibitors; proteasome inhibitors; compounds used in the treatment of hematologic malignancies, such as FLUDARABINE; compounds which target, decrease or inhibit the activity of PKC, such as midostaurin; HSP90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics, HSP990 and AUY922; temozolomide (TEMODAL®); kinesin spindle protein inhibitors, such as SB715992 or SB743921 from GlaxoSmithKline, or pentamidine/chlorpromazine from CombinatoRx; PI3K inhibitors, such as BEZ235, BKM120 or BYL719; MEK inhibitors such as ARRY142886 from Array PioPharma, AZD6244 from AstraZeneca, PD181461 from Pfizer, leucovorin, EDG binders, antileukemia compounds, S-adenosylmethionine decarboxylase inhibitors, antiproliferative antibodies or other chemotherapeutic compounds. Further, alternatively or in addition they may be used in combination with ionizing radiation. Further, alternatively or in addition they may be used in combination with JAK inhibitors, such as ruxolitinib.

Further, alternatively or in addition they may be used in combination with smoothened inhibitors, such as LDE225.

Further, alternatively or in addition they may be used in combination with interferon.

The term "ribonucleotide reductase inhibitors" refers to pyrimidine or purine nucleoside analogues including, but not limited to, fludarabine and/or cytosine arabinoside (ara-C), 6-thioguanine, 5-fluorouracil, cladribine, 6-mercaptopurine (especially in combination with ara-C against ALL), clofarabine, nelarabine (a prodrug of 9-β-arabinofuranosylguanine, ara-G), pentostatin, hydroxyurea or 2-hydroxy-1H-isoindole-1,3-dione derivatives (Nandy et al., Acta Oncologica 1994; 33:953-961.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, in the form as it is marketed. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds such as LDH589 disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity" as used herein includes, but is not limited to, protein tyrosine kinase and/or serine and/or threonine kinase inhibitors or lipid kinase inhibitors, for example:

a) compounds targeting, decreasing or inhibiting the activity of members of the ABL1 family, their gene-fusion products (e.g. BCR-ABL1 kinase) and mutants, such as compounds which target decrease or inhibit the activity of ABL1 family members and their gene fusion products, e.g. imatinib, nilotinib, dasatinib, bosutinib, ponatinib, bafetinib, PD180970, AG957, NSC 680410 and PD173955;

b) compounds targeting, decreasing or inhibiting the activity of members of the protein kinase C(PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor);

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. Example HSP90 inhibitors are HSP990 and AUY922.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt.

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "S-adenosylmethionine decarboxylase inhibitors" as used herein includes, but is not limited to the compounds disclosed in U.S. Pat. No. 5,461,076.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Where temperatures are given hereinbefore or hereinafter, "about" has to be added, as minor deviations from the numeric values given, e.g. variations of ±10%, are tolerable. All reactions may take place in the presence of one or more diluents and/or solvents. The starting materials may be used in equimolar amounts; alternatively, a compound may be used in excess, e.g. to function as a solvent or to shift equilibrium or to generally accelerate reaction rates. Reaction aids, such as acids, bases or catalysts may be added in suitable amounts, as known in the field, required by a reaction and in line with generally known procedures.

Compounds of formula (I) can be prepared by proceeding as in the following Reaction Scheme I:

Reaction Scheme I:

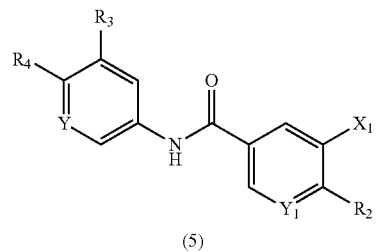

(5)

-continued

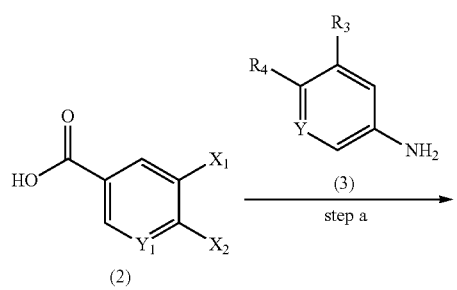
(2)

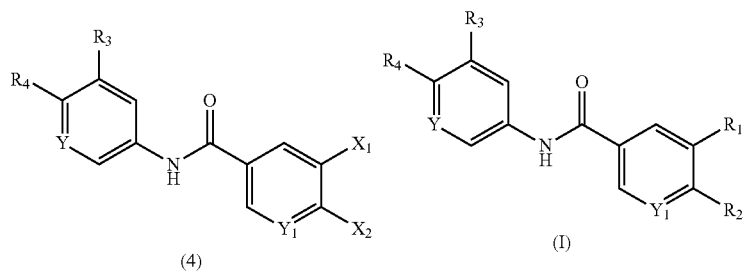
(4) (I)

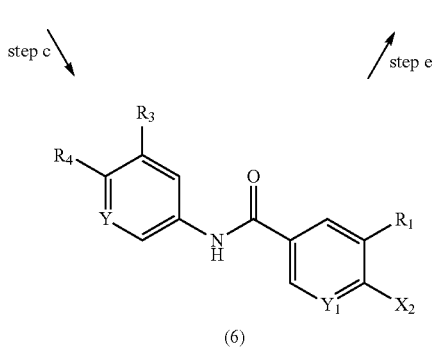
(6)

in which Y, Y$_1$, R$_1$, R$_2$, R$_3$ and R$_4$ are as defined for formula (I) in the Summary of the Invention and X$_1$ and X$_2$ represent halogen atoms, X$_1$ can be selected from chloro, bromo, or iodo and X$_2$ can be selected from chloro or fluoro.

Step a: A compound of formula (4) can be prepared by reacting the acid chloride from a compound of formula (2) with a compound of formula (3) in the presence of a suitable solvent (for example tetrahydrofuran, or the like), and an organic base (for example diisopropylethylamine, or the like). The reaction takes place from about 0° C. to about room temperature and can take up to about 2 hours to complete.

The acid chloride of a compound of formula (2) can be prepared with a chlorinating agent (for example thionyl chloride, or oxalyl chloride, or the like) in the presence of a catalyst (for example dimethylformamide, or the like) and a suitable solvent (for example toluene, or the like). The reaction takes place at about room temperature or by heating to about 85° C. and can take up to about 2 hours to complete.

Step b: A compound of formula (5) can be prepared by reacting a compound of formula (4) with R$_2$—H wherein R$_2$ is as defined in the Summary of the Invention, in the presence of a suitable solvent (for example 2-propanol, or dimethyl sulfoxide, or the like), and a suitable organic base (for example diisopropylethylamine, or triethylamine, or the like). The reaction takes place at about 90° C. to about 140° C. and can take from about 30 minutes to about 72 hours to complete.

Step c: A compound of formula (6) can be prepared by reacting a compound of formula (4), X$_1$ being preferably bromo or iodo, with R$_1$—Z$_1$, wherein R$_1$ is as defined herein, Z$_1$ being preferably a boronic acid or ester (Suzuki reaction), in the presence of a suitable solvent (for example dimethoxyethane, or a mixture of dimethoxyethane and water, or the like), a suitable inorganic base (for example sodium carbonate, or the like), and a palladium catalyst (for example bis(triphenylphosphine)palladium(II) dichloride, or 1,1'-bis(diphenylphosphino)ferrocene-palladium(II)dichloride dichloromethane complex, or tetrakis(triphenylphosphine)palladium(0), or the like) and optionally a cosolvent (for example, ethanol, or the like. The reaction takes place from about 80° C. to about 130° C. and can take from about 20 minutes to about 18 hours to complete.

Alternatively, step c can occur by reacting a compound of formula (4), X$_1$ being preferably bromo or iodo, with R$_1$—Z$_2$, wherein R$_1$ is as defined herein, Z$_2$ being preferably a trialkylstannyl reagent (Stille reaction), in the presence of a suitable solvent (for example dimethyl sulfoxide, or the like), and a palladium catalyst (for example tetrakis(triphenylphosphine)palladium(0). The reaction takes place at about 140° C. and can take up to about 18 hours to complete.

Step d: A compound of formula (I) can be prepared by reacting a compound of formula (5), X$_1$ being preferably bromo or iodo, with R$_1$—Z$_1$, wherein R$_1$ is as defined herein, Z$_1$ being preferably a boronic acid or ester (Suzuki reaction), in the presence of a suitable solvent (for example dimethoxyethane, or a mixture of dimethoxyethane and water, or the like), a inorganic base (for example sodium carbonate, or the like), and a palladium catalyst (for example bis(triphenylphosphine)palladium(II) dichloride, or 1,1'-bis(diphenylphosphino)ferrocene-palladium(II)dichloride dichloromethane complex, or tetrakis(triphenylphosphine)palladium(0), or the like) and optionally a cosolvent (for example, ethanol, or the like). The reaction takes place at about 80-130° C. and can take up to about 20 minutes to 2 hours to complete.

Step e: A compound of formula (I) can be prepared by reacting a compound of formula (6) with R$_2$—H wherein R$_2$ is as defined herein, in the presence of a suitable solvent (for example 2-propanol, or dimethyl sulfoxide, or the like), an organic base (for example diisopropylethylamine, or triethylamine, or the like). The reaction takes place at about 90-140° C. and can take up to about 30 minutes to 72 hours to complete.

Compounds of formula (I) can be prepared by proceeding as in the following Reaction Scheme II:

Reaction Scheme II:

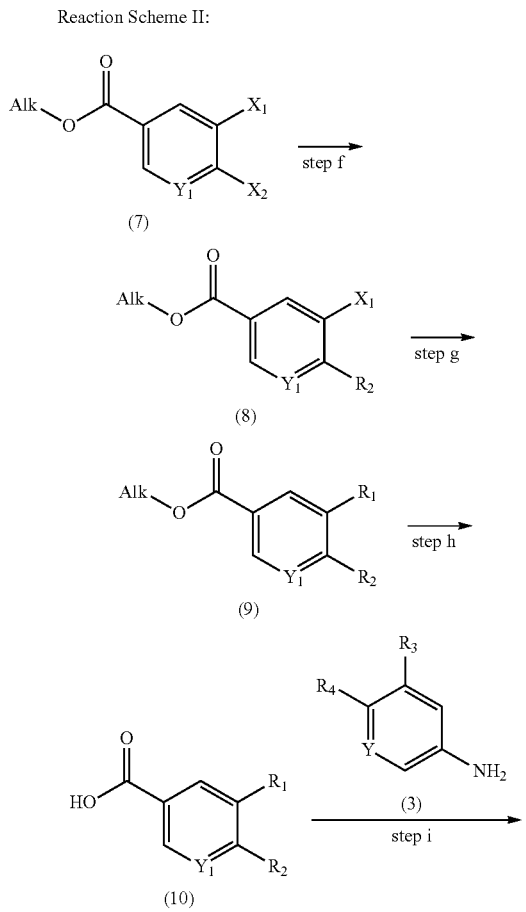

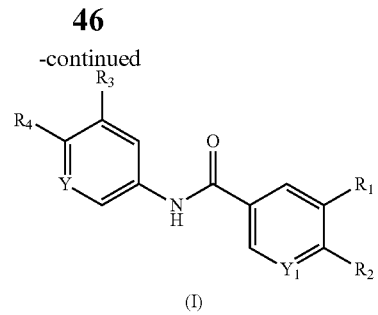

in which Y, $Y_1$, $R_1$, $R_2$, $R_3$ and $R_4$ are as defined for formula (I) in the Summary of the Invention and $X_1$ and $X_2$ represent halogen atoms, $X_1$ in particular chloro, bromo, or iodo, $X_2$ in particular chloro or fluoro and Alk is low alkyl chain in particular methyl.

Step f: A compound of formula (8) can be prepared by reacting a compound of formula (7) with $R_2$—H wherein $R_2$ is as defined herein, in analogy to Step b Step g: A compound of formula (9) can be prepared by reacting a compound of formula (8), $X_1$ being preferably bromo or iodo, with $R_1$—$Z_1$, where $R_1$ is as defined herein, $Z_1$ being preferably a boronic acid or ester (Suzuki reaction), in analogy to Step d.

Step h: A compound of formula (10) can be prepared by hydrolysis of the ester of a compound of formula (9) in the presence of a suitable solvent (for example water, or the like), an inorganic base (for example sodium hydroxide, or the like). The reaction takes place at room temperature and can take up to about 2 hours complete.

Step i: A compound of formula (I) can be prepared by reacting a compound of formula (10) with a compound of formula (3) in the presence of a coupling reagent (such as 1-ethyl-3-(3-dimethylaminopropyl)carbodiimide hydrochloride and hydroxybenzotriazole, or the like), a suitable base (such as N-methylmorpholine, diisopropylethylamine, or the like) and a suitable solvent (such as dichloromethane, dimethylformamide, or the like). The reaction takes place at room temperature and can take up to about 12 hours to complete.

Compounds of formula (I) can be prepared by proceeding as in the following Reaction Scheme III:

Reaction Scheme III:

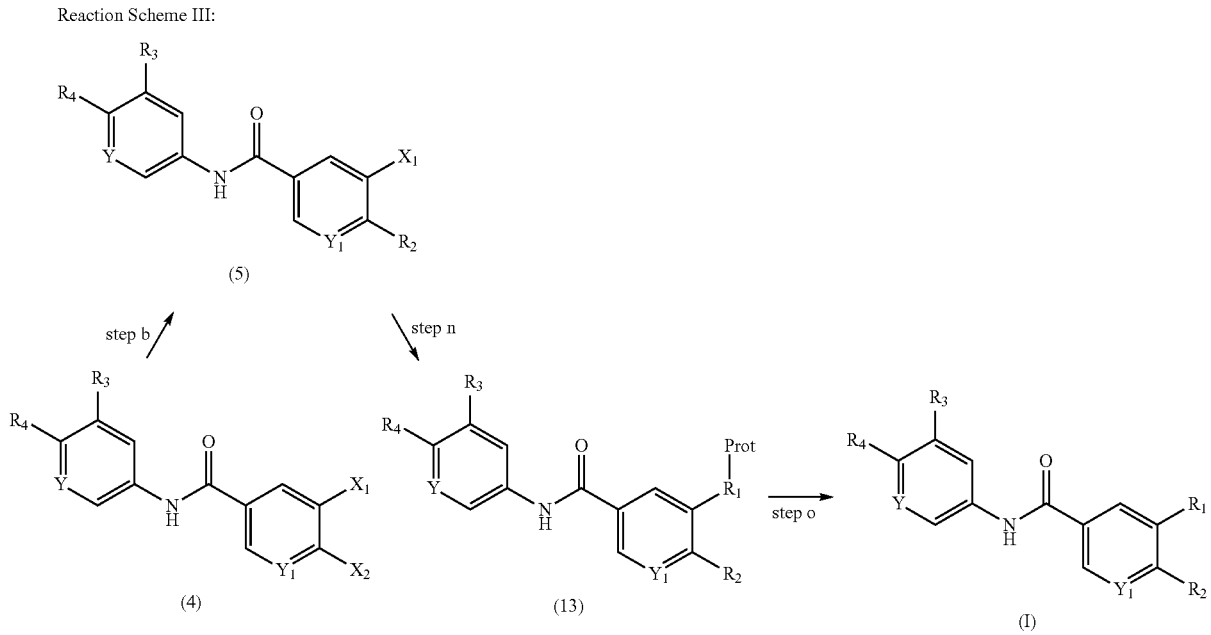

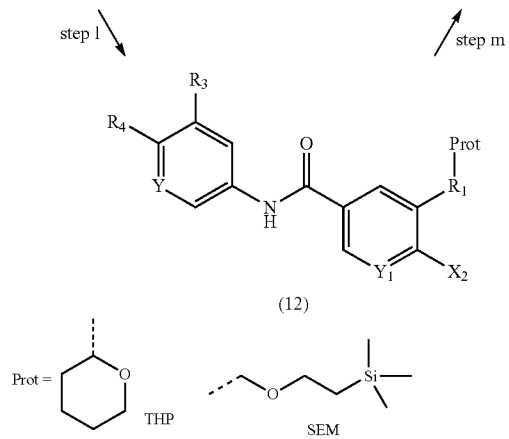

in which Y, $Y_1$, $R_1$, $R_2$, $R_3$ and $R_4$ are as defined for formula (I) in the Summary of the Invention and $X_1$ and $X_2$ represent halogen atoms, $X_1$ in particular chloro, bromo, or iodo, $X_2$ in particular chloro or fluoro, Prot represents a protecting group, in particular tetrahydro-2H-pyran-2-yl (THP) or 2-(trimethylsilyl)ethoxy]methyl (SEM) when $R_1$ is pyrazole with free NH.

Step l: A compound of formula (12) can be prepared by reacting a compound of formula (4) with Prot-$R_1$—$Z_1$ where $R_1$ is as defined herein, $Z_1$ being preferably a boronic acid or ester (Suzuki reaction), Prot is in particular THP or SEM, in analogy to Step c.

Step m: A compound of formula (13) can be prepared by reacting a compound of formula (12) with $R_2$—H wherein $R_2$ is as defined herein, in analogy to Step e.

Step n: A compound of formula (13) can be prepared by reacting a compound of formula (5) with Prot-$R_1$—$Z_1$ where $R_1$ is as defined herein, $Z_1$ being preferably a boronic acid or ester (Suzuki reaction), Prot is in particular THP or SEM, in analogy to Step d.

Step o: A compound of formula (I) can be prepared by reacting a compound of formula (13) with a deprotecting agent (for example tetra-n-butylammonium fluoride, or trifluoroacetic acid, or hydrochloric acid, or the like) in the presence of a suitable solvent (for example tetrahydrofuran, or dichloromethane, or the like). The reaction takes place at room temperature or to about 80° C. and can take up to about 2 to 24 hours to complete.

Compounds of formula (I), where $R_1$ is a pyrazole substituted by a $R_6$ group, can be prepared by proceeding as in the following Reaction Scheme IV:

Reaction Scheme IV:

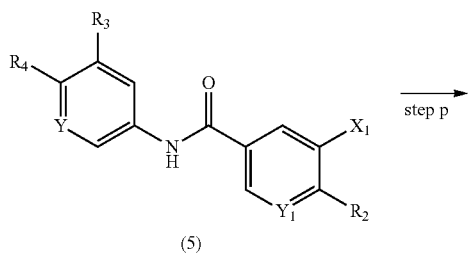

in which Y, $Y_1$, $R_2$, $R_3$, $R_4$ and $R_6$ are as defined for formula (I) in the Summary of the Invention and $X_1$ represents an halogen atom, in particular bromo, or iodo, and $R_6$ being lower alkyl, in particular methyl.

Step p: A compound of formula (14) can be prepared by reacting a compound of formula (5) with an alkylvinylketon (for example methylvinylketon, or the like) in the presence of a suitable solvent (for example dimethylformamide, or the like), an organic base (for example triethylamine, or the like), and a palladium catalyst (for example tri-o-tolylphosphine-palladium diacetate, or the like). The reaction takes place at about 130° C. and can take up to 16 hours to complete.

Step q: A compound of formula (Id) can be prepared by reacting a compound of formula (14) by reacting with a protected hydrazide (for example toluene-4-sulfonic acid hydrazide, or the like) in the presence of a suitable solvent (for example ethanol, or the like), The reaction takes place at about 80° C. and can take up to 2 hours to complete. Then the protecting group is removed in situ with an alcoholate (for example sodium methoxyde, or the like). The deprotection takes place at about 80° C. and can take up to 48 hours to complete.

Compounds of formula (I) can be prepared by proceeding as in the following Reaction Scheme V:

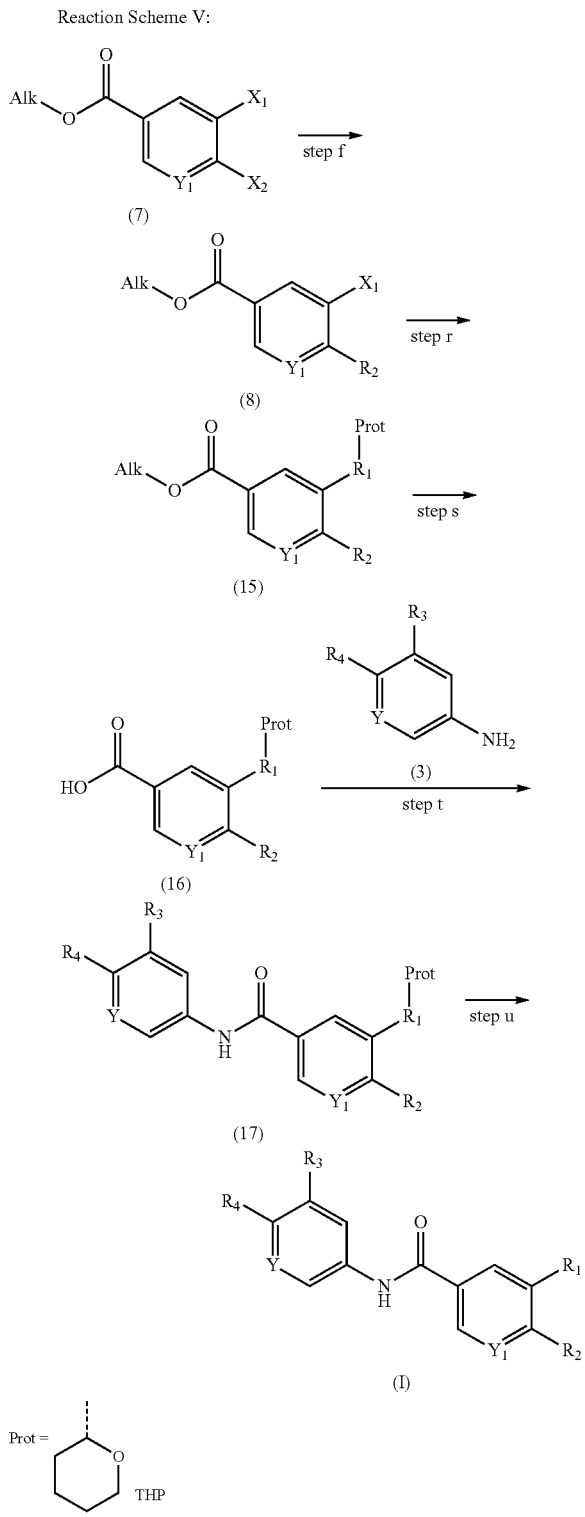

in which Y, $Y_1$, $R_1$, $R_2$, $R_3$ and $R_4$ are as defined for formula (I) in the Summary of the Invention, $X_1$ and $X_2$ represent halogen atoms, $X_1$ in particular chloro, bromo, or iodo, $X_2$ in particular chloro or fluoro and Alk is low alkyl chain in particular methyl, Prot represents a protecting group, in particular tetrahydro-2H-pyran-2-yl (THP) when $R_1$ is pyrazole with free NH.

Step r: A compound of formula (15) can be prepared by reacting a compound of formula (8), $X_1$ being preferably bromo or iodo, with Prot-$R_1$—$Z_1$, where $R_1$ is as defined herein, Prot is in particular tetrahydro-2H-pyran-2-yl (THP) when $R_1$ is pyrazole with free NH, $Z_1$ being preferably a boronic acid or ester (Suzuki reaction), in analogy to Step d.

Step s: A compound of formula (16) can be prepared by hydrolysis of the ester of a compound of formula (15) in the presence of a suitable solvent (for example water and methanol, or the like), an inorganic base (for example sodium hydroxide, or the like). The reaction takes place at room temperature and can take up to about 14 hours complete.

Step t: A compound of formula (17) can be prepared by reacting a compound of (16) with a compound of formula (3) in the presence of a coupling reagent (such as 1-ethyl-3-(3-dimethylaminopropyl)carbodiimide hydrochloride and hydroxybenzotriazole, or the like), a suitable base (such as N-methylmorpholine, or the like) and a suitable solvent (such as tetrahydrofuran, or the like). The reaction takes place at about 25°-65° C. and can take up to about 2 days to complete.

Step u: A compound of formula (I) can be prepared by reacting a compound of formula (17) with a deprotecting agent (for example hydrochloric acid, or the like) in the presence of a suitable solvent (for example tetrahydrofuran and methanol, or the like). The reaction takes place at room temperature about 2 hours to complete.

Detailed examples of the synthesis of compounds of formula (I) can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula (I) can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Wherever compounds of the formula (I), and/or N-oxides, tautomers and/or (preferably pharmaceutically acceptable) salts thereof are mentioned, this comprises such modified formulae, while preferably the molecules of the formula (I), their N-oxides, their tautomers and/or their salts are meant.

Alternatively, the salt forms of the compounds of the invention can be prepared using salts of the starting materials or intermediates. In view of the close relationship between the novel compounds of the formula (I) in free form and those in the form of their salts, including those salts that can be used as intermediates, for example in the purification or identification of the novel compounds, any reference to the compounds or a compound of the formula (I) hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid. Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier M G, Langley D R, Kadow J F, Senter P D, Knipe J O, Tun M M, Vyas D M and Doyle T W (1994) Synthesis of etoposide phosphate, BMY-4048 1: a watersoluble clinically active prodrug of etoposide. Bioorg Med Chem Lett 4:2567-2572; and Rautio J, Kumpulainen H, Heimbach T, Oliyai R, Oh D, Järvinen T and Savolainen J (2008); Prodrugs: design and clinical applications. Nat Rev Drug Discov. 7:255-70). For example, a compound of the invention can form a phosphate ester of a hydroxyl group. More specifically, a compound of the invention can form a prodrug as shown:

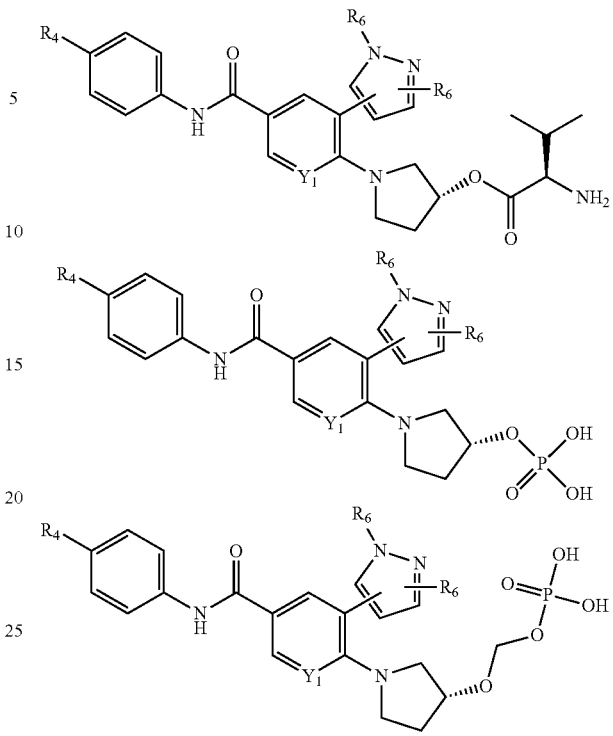

Further, a compound of the invention can be a prodrug of another compound of the invention. To illustrate, example 36 is a prodrug of example 37 and example 37 is a potential metabolite of example 36.

Protected derivatives of the compounds of the invention can be made by means known to those of ordinary skill in the art. If one or more other functional groups, for example carboxy, hydroxy, amino, sulfhydryl or the like are or need to be protected in a starting material as described herein or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which are groups that are added at a starting material or intermediate stage and removed to obtain a final compound. Also in the case of conversions of a compound of the formula (I) into a different compound of the formula (I), protecting groups may be introduced and removed, if useful or required. The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. Diastereomeric mixtures for example may be separated into their individual diastereomers by means of fractionated crystallization, chromatography, solvent distribution, and similar procedures. This separation may take place either at the level of a starting compound or in a compound of formula (I) itself. Enantiomers may be separated through the formation of diastereomeric salts, for example by salt formation with an enantiomer-pure chiral acid, or by means of chromatography, for example by HPLC, using chromatographic substrates with chiral ligands. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of formula (I) can be made by a process, which involves:

(a) those of reaction schemes I-V; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following Examples illustrate the invention without limiting the scope thereof. In the Examples provided, temperatures are given in degrees Celsius. Unless otherwise indicated, the reactions take place at room temperature. Further, if not indicated otherwise, the analytical HPLC conditions are as follows:

Condition 1:

UPLC-MS, column Acquity BEH C18, 1.7 µm, 2.1×50 mm, oven at 40° C., eluents: A=water+0.1% formic acid and B=MeCN+0.1% formic acid, gradient from 20% to 100% B in 4.3 min, flow 0.7 mL/min, detection UV/VIS (DAD), ESI (+/−).

Condition 2:

LC-MS, column Ascentis® Express C18 2.7 µm 2.1×30 mm, 50° C., eluents: A=water+0.05% formic acid+3.75 mM ammonium acetate and B=MeCN+0.04% formic acid, gradient from 5% to 95% B in 3.7 min, flow 1.2 mL/min to 1.4 mL/min in 3.7 min, detection UV/VIS (DAD), ESI (+/−).

Condition 3:

UPLC-MS, column Acquity HSS T3, 1.8 µm, 2.1×50 mm, oven at 50° C., eluents: A=water+0.05% formic acid+3.75 mM ammonium acetate and B=MeCN+0.04% formic acid, gradient from 2% to 98% B in 1.40 min, then 98% B for 0.75 min, flow 1.2 mL/min, detection UV/VIS (DAD), ESI (+/−).

Condition 4:

HPLC, column Chromolith® Performance, RP-18e, 100×4 6 mm+precolumn 5×4.6 mm at RT, eluents: A=water+0.1% formic acid and B=MeCN+0.1% formic acid, gradient from 2% to 100% B in 8 min, then 100% B for 2 min, flow 2.0 mL/min, detection UV/VIS (DAD).

Condition 5:

HPLC, column CC125/4 Nucleosil® 100-3 C18HD, 4.0×125 mm, eluents: A=water+0.1% TFA and B=MeCN+0.1% TFA, gradient from 2% to 100% B in 7 min, then 100% B for 2 min and finally 100% to 2% B in 1 min, flow 1.0 mL/min, detection UV 215 nm.

Condition 6:

similar condition as Condition 3, oven at 60° C. instead of 50° C.

Condition 7:

HPLC, column Eclipse XDB C18, 5 µm, 4.6×150 mm, oven at 25° C., eluents: A=water+0.1% $H_3PO_4$ and B=MeCN, gradient from 10% to 95% B in 17 min, flow 1.0 mL/min, detection UV/VIS (DAD) 210 nm.

Condition 8:

LC-MS, column Poroshell® 120 SB-C18, 3.0×50 mm, 2.7 µm, eluents: A=water+0.1% TFA and B=MeCN+0.1% TFA, gradient from 5% B for 0.5 min, 5% to 95% B in 6.5 min, 95% B for 3 min, 95% to 5% B in 0.1 min, 5% B for 2 min, flow 0.8 mL/min, UV/VIS (DAD), ESI (+).

Further, if not indicated otherwise, the preparative HPLC conditions are as follows:

Condition 9:

Preparative HPLC, Column. XBridge C18 30×100 mm, 5 μm; flow rate 30 mL/min; mobile phase: A=water+0.1% formic acid; B=MeCN; variable gradient, from initial % B to final % B, and runtime as specified in the Examples.

Condition 10:

Preparative HPLC Gilson system, column SunFire™ prep C18 OBD, 5 μm 30×100 mm, eluents: A=water+0.1% TFA and B=MeCN, gradient 5% B for 2 min, then 5% to 100% B in 20 min and finally 100% B in 3 min, flow 30 mL/min, detection UV/VIS.

Preparative achiral SFC is done using the following system: Waters SFC THAR100; flow rate 100 mL/min; mobile phase: A=supercritical $CO_2$; B=MeOH; variable gradient, from initial % B to final % B runtime and columns as specified in the Examples. Details for the columns:

Column DEAP: column Diethyl amino (250×30 mm, 5 μm, 60 Å), Princeton

Column Diol: column Diol (250×30 mm, 5 μm, 60 Å), Princeton $^1$H-NMR spectra were recorded on a 300 MHz, or a 400 MHz NMR spectrometer as indicated. Significant peaks are tabulated in the order: multiplicity (s, singlet; d, doublet; t, triplet; q, quartet; m, multiplet; br. s, broad singlet) and number of protons.

In the following Examples, the abbreviations given below are used: aq. (aqueous); DAD (diode array detector); DCM (dichloromethane); DIPEA (diisopropyl-ethylamine); DMF (N,N-dimethylformamide); DME (dimethoxyethane); DMSO (dimethyl sulfoxide); dppf (1,1'-bis(diphenylphosphino)ferrocene); eq. (equivalents); ESI (electrospray ionization); EtOAc (ethyl acetate); EtOH (ethanol); $Et_2O$ (diethyl ether); h (hour); HPLC (high performance liquid chromatography); HV (high vacuum); iPrOH (isopropanol); $iPr_2O$ (diisopropyl ether); LC (liquid chromatography); M (molar); MeCN (acetonitrile); MeOH (methanol); MeTHF (2-methyltetrahydrofuran); min (minutes); mL (milliliters); MP (macroporous); MPLC (medium pressure liquid chromatography); MS (mass spectrometry); MW (microwave); n-BuLi (n-butyllithium); NMM (N-methylmorpholine); NMP (N-methylpyrrolidinone); NMR (nuclear magnetic resonance); PL (polystyrene); $PPh_3$ (triphenylphosphine); PTFE (polytetrafluorethylene); RM (reaction mixture); RT (room temperature); sat. (saturated); sec (seconds); SFC (supercritical fluid chromatography); Si-Thiol (3-mercaptopropyl modified silica gel); SPE (solid phase extraction); TBAF (tetra-n-butylammonium fluoride); TBME (methyl tert-butyl ether); TFA (trifluoroacetic acid); THF (tetrahydrofuran); $t_R$ (retention time); UPLC (ultra performance liquid chromatography) and UV (Ultraviolet).

Example 1

(R)-4-(3-Hydroxypyrrolidin-1-yl)-3-(1H-pyrazol-5-yl)-N-(4-(trifluoromethoxy)phenyl)benzamide

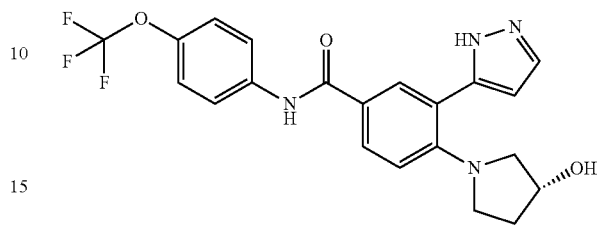

(R)-4-(3-Hydroxypyrrolidin-1-yl)-N-(4-(trifluoromethoxy)phenyl)-3-(1-((2-(trimethylsilyl)ethoxy)methyl)-1H-pyrazol-5-yl)benzamide (Stage 1.1, 149 mg, 0.2 mmol) was added to a MW vial, which was sealed and flushed with argon. A solution of 1 M TBAF in THF (2.98 mL, 2.98 mmol) was then added and the RM was stirred at 80° C. for 3 days. The RM was diluted with EtOAc (40 mL), washed with sat. $NaHCO_3$ and brine, dried over $Na_2SO_4$ and the solvent was evaporated off under reduced pressure. The crude product was purified by preparative SFC (Column DEAP, from 25% to 30% in 6 min) to yield the title compound as a white solid. UPLC-MS (Condition 3) $t_R$=0.98 min, m/z=433.3 [M+H]$^+$, m/z=431.3 [M−H]$^−$; $^1$H-NMR (400 MHz, DMSO-$d_6$) δ ppm 1.75 (br. s, 1H) 1.86 (br. s, 1H) 2.70-2.79 (m, 1H) 3.03-3.19 (m, 2H) 3.19-3.28 (m, 1H) 4.20 (br. s, 1H) 4.73-4.92 (m, 1H) 6.34 (d, J=11.00 Hz, 1H) 6.73-6.94 (m, 1H) 7.32 (d, J=8.80 Hz, 2H) 7.65 (d, J=104.42 Hz, 1H) 7.81-7.96 (m, 4H) 10.10 (s, 1H) 12.88 (d, J=81.67 Hz, 1H).

Stage 1.1: (R)-4-(3-Hydroxypyrrolidin-1-yl)-N-(4-(trifluoromethoxy)phenyl)-3-(1-(2-(trimethylsilyl)ethoxy)methyl)-1H-pyrazol-5-yl)benzamide

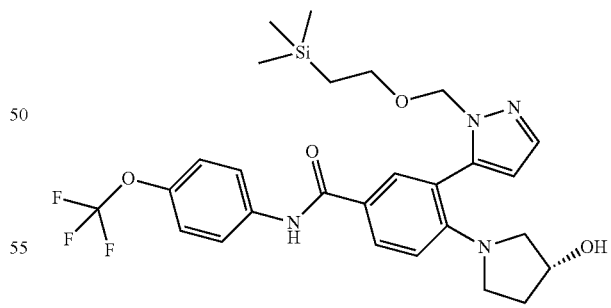

A suspension of (R)-3-bromo-4-(3-hydroxypyrrolidin-1-yl)-N-(4-(trifluoromethoxy)phenyl)benzamide (Stage 1.2, 100 mg, 0.225 mmol), 5-(4,4,5,5-tetramethyl-1,3,2-dioxaborolan-2-yl)-1-((2-(trimethylsilyl)ethoxy)methyl)-1H-pyrazole (146 mg, 0.45 mmol), Pd(PPh$_3$)$_2$Cl$_2$ (17.34 mg, 0.025 mmol) and $Na_2CO_3$ (119 mg, 1.123 mmol) in a mixture of water (272 μL), DME (953 μL) and EtOH (136 μL) was subjected to MW irradiation at 125° C. for 20 min. The RM was diluted with THF (3 mL), treated with Si-Thiol (Silicycle, 1.44 mmol/g, 94 mg, 0.135 mmol), filtered and the filtrate was evaporated off under reduced pressure to give a residue which was purified by flash chromatography (RediSep® Silica gel column, 4 g, cyclohexane/EtOAc from 40% to 100% EtOAc) to yield the title compound as a yellow oil. UPLC-MS (Condition 1) $t_R$=3.28 min, m/z=563.2 [M+H]$^+$, m/z=561.2 [M−H]$^−$.

Stage 1.2: (R)-3-Bromo-4-(3-hydroxypyrrolidin-1-yl)-N-(4-(trifluoromethoxy)phenyl)benzamide

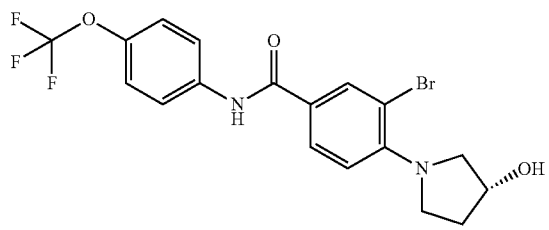 [SMILES: O=C(Nc1ccc(OC(F)(F)F)cc1)c1ccc(N2CC[C@@H](O)C2)c(Br)c1]

A mixture of 3-bromo-4-fluoro-N-(4-(trifluoromethoxy)phenyl)benzamide (Stage 1.3, 100 mg, 0.264 mmol), (R)-pyrrolidin-3-ol (46.1 mg, 0.529 mmol) and TEA (147 µL, 1.058 mmol) in DMSO (199 µL) was stirred at 90° C. for 16 h. The RM was diluted with TBME/EtOAc (1:1) (30 mL), washed with 0.5 M HCl (3×5 mL) and brine (5 mL) and the solvent was evaporated off under reduced pressure to give a crude product that was purified by flash chromatography (RediSep® Silica gel column, 4 g, cyclohexane/EtOAc-EtOH+0.1% NH$_4$OH (8:2), from 30% to 80% EtOAc-EtOH+ 0.1% NH$_4$OH (8:2)) to yield the title compound as an off-white solid. UPLC-MS (Condition 1) $t_R$=2.83 min, m/z=444.9/446.9 [M+H]$^+$, m/z=443.0/445.0 [M−H]$^−$; $^1$H-NMR (400 MHz, DMSO-d$_6$) δ ppm 1.80-1.92 (m, 1H) 1.92-2.04 (m, 1H) 3.24-3.30 (m, 1H). 3.36-3.46 (m, 1H) 3.60-3.72 (m, 1H) 3.81 (dd, J=10.51, 4.65 Hz, 1H) 4.36 (d, J=2.69 Hz, 1H) 4.97 (d, J=3.42 Hz, 1H) 6.93 (d, J=8.80 Hz, 1H) 7.34 (d, J=8.56 Hz, 2H) 7.80-7.90 (m, 3H) 8.14 (d, J=1.96 Hz, 1H) 10.19 (s, 1H).

Stage 1.3: 3-Bromo-4-fluoro-N-(4-(trifluoromethoxy)phenyl)benzamide

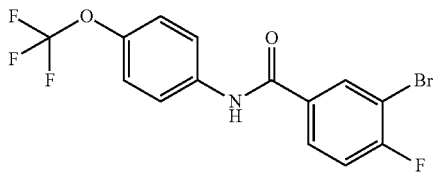

SOCl$_2$ (2.92 mL, 40.0 mmol) and DMF (0.5 mL) were added dropwise to a suspension of 3-bromo-4-fluorobenzoic acid (1.752 g, 8 mmol) in toluene (20 mL) and the RM was stirred at 80° C. for 1 h. The solvent was evaporated off under reduced pressure and the residue was diluted with THF (15 mL). DIPEA (2.79 mL, 16.00 mmol) was added and the mixture was cooled to 0° C., treated with a solution of 4-trifluoromethoxyaniline (1.181 mL, 8.80 mmol) in THF (5 mL) and stirred for 1 h. The RM was treated with aq. 1 M HCl (50 mL), and extracted with TBME. The combined extracts were washed with aq. 1 M HCl, aq. 1 M NaOH and brine, dried over MgSO$_4$ and the solvent was evaporated off under reduced pressure to give a residue was crystallized from n-heptane/DCM to afford the title compound as a white solid. UPLC-MS (Condition 1) $t_R$=3.18 min, m/z=377.9/379.9 [M+H]$^+$, m/z=375.9/377.9 [M−H]$^−$; $^1$H-NMR (400 MHz, DMSO-d$_6$) δ ppm 7.38 (d, J=8.6 Hz, 2H) 7.56 (t, J=8.7 Hz, 1H) 7.87 (d, J=9.0 Hz, 2H) 8.00-8.06 (m, 1H) 8.32 (dd, J=6.6, 2.2 Hz, 1H) 10.50 (s, 1H).

Example 2

(R)-6-(3-Hydroxypyrrolidin-1-yl)-5-(1H-pyrazol-3-yl)-N-(4-(trifluoromethoxy)phenyl)nicotinamide

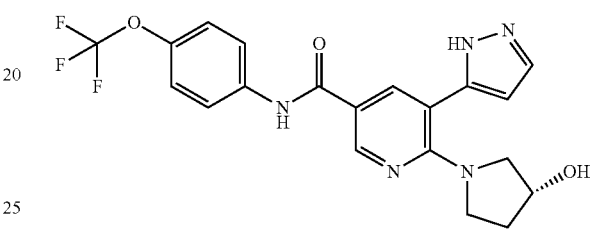

A mixture of DME (570 µL), water (163 µL) and EtOH (81 µL) was added to a mixture of (R)-5-bromo-6-(3-hydroxypyrrolidin-1-yl)-N-(4-(trifluoromethoxy)phenyl)nicotinamide (Stage 2.2, 60 mg, 0.134 mmol), (1H-pyrazol-3-yl)boronic acid (45.1 mg, 0.403 mmol) Pd(PPh$_3$)$_2$Cl$_2$ (9.44 mg, 0.013 mmol), Na$_2$CO$_3$ (42.8 mg, 0.403 mmol) in a MW vial. The vial was sealed, evacuated/purged 3 times with argon and the RM was subjected to MW irradiation at 120° C. for 10 min. Additional (1H-pyrazol-3-yl)boronic acid (45.1 mg, 0.403 mmol) was added and the RM was subjected to MW irradiation at 120° C. for 30 min, diluted with THF (1 mL) and treated with Si-Thiol (Silicycle 1.27 mmol/g, 52.9 mg, 0.067 mmol), filtered and the filtrate was evaporated off under reduced pressure to give a residue which was purified by preparative HPLC (Condition 9, 15% for 0.2 min then 15% to 45% in 14 min) to yield the title compound as a white solid.

Alternatively, Example 2 was prepared by treating a suspension of 6-((R)-3-hydroxypyrrolidin-1-yl)-5-(1-(tetrahydro-2H-pyran-2-yl)-1H-pyrazol-5-yl)-N-(4-(trifluoromethoxy)phenyl)nicotinamide (Stage 2.1, 68.3 g, 132 mmol) in DCM (1 L) with TFA (305 mL, 3959 mmol) at RT for 5.5 h. The solvent was evaporated off under reduced pressure and the residue was dissolved in EtOAc (2 L), washed with a sat. solution of NaHCO$_3$ (3×500 mL) and brine (2×500 mL), and dried over Na$_2$SO$_4$. The solvent was evaporated off under reduced pressure and the residue was suspended in DCM (300 mL) and stirred at RT for 15 min. The crystalline material was filtered, washed with DCM (200 mL), dried under reduced pressure, dissolved in MeOH (500 mL) and treated with Si-Thiol (Biotage, 10.0 g, 13 mmol) for 15 h at 30° C. The mixture was filtered and the solvent was evaporated off under reduced pressure to give the crude product which was purified by flash chromatography (Silica gel, 2 kg, DCM/MeOH 95:5) and crystallized from MeCN to afford the title compound as a white crystalline solid.

Analytical data for Example 2: HPLC (Condition 5) $t_R$=5.37 min, HPLC Chiral (CHIRALPAK® AD-H, 250×4.6 mm, eluent:EtOH/MeCN (98:2), 0.5 mL/min, UV 210 nm) $t_R$ 9.62 min, UPLC-MS (condition 1) $t_R$=1.79 min, m/z=434.1/435.1 [M+H]$^+$, m/z=432.1/433.1 [M−H]$^−$;

¹H-NMR (400 MHz, DMSO-d₆) δ ppm 1.65-1.76 (m, 1H) 1.76-1.87 (m, 1H) 2.97 (d, J=11.37 Hz, 1H) 3.19-3.29 (m, 2H) 3.34-3.48 (m, 1H) 4.10-4.23 (m, 1H) 4.89 (br. s, 1H) 6.40 (s, 1H) 7.33 (d, J=8.70 Hz, 2H) 7.58/7.82 (br. s, 1H) 7.89 (d, J=8.70 Hz, 2H) 8.06 (s, 1H) 8.77 (s, 1H) 10.21 (s, 1H) 12.88/13.07 (br. s, 1H).

Stage 2.1: 6-((R)-3-Hydroxypyrrolidin-1-yl)-5-(1-(tetrahydro-2H-pyran-2-yl)-1H-pyrazol-5-yl)-N-(4-(trifluoromethoxy)phenyl)nicotinamide

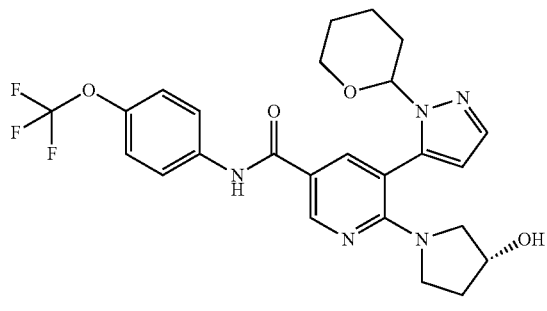 [SMILES: O=C(Nc1ccc(OC(F)(F)F)cc1)c1cnc(N2CC[C@@H](O)C2)c(-c2ccnn2C2CCCCO2)c1]

1-(Tetrahydro-2H-pyran-2-yl)-1H-pyrazole-5-boronic acid pinacol ester (59.9 g, 214.4 mmol), K₃PO₄ (105.7 g, 498.1 mmol) and Pd(PPh₃)₄ (9.6 g, 8.30 mmol) were added to a suspension of (R)-5-bromo-6-(3-hydroxypyrrolidin-1-yl)-N-(4-(trifluoromethoxy)phenyl)nicotinamide (Stage 2.2, 74 g, 165.8 mmol) in toluene (740 mL) and stirred at 110° C. for 2.5 h under argon. The mixture was then diluted with EtOAc (2 L), washed with water (2×1 L) and dried over Na₂SO₄. The solvent was evaporated off under reduced pressure and the crude residue was purified by flash chromatography (Silica gel, 2 kg, DCM/MeOH 95:5). The resulting material was dissolved in a mixture of MeOH (500 mL) and THF (800 mL) and was treated with Si-Thiol (Biotage, 15 g, 19.5 mmol) at RT for 17 h. The mixture was filtered and the solvent was evaporated off under reduced pressure to give a residue which was crystallized from MeOH to give the title compound as a white crystalline solid. HPLC (Condition 5) t_R=5.99 min, UPLC-MS (Condition 6) m/z=518.2 [M+H]⁺; ¹H-NMR (400 MHz, DMSO-d₆) δ ppm 1.42 (br. s, 3H) 1.63-1.98 (m, 4H) 2.20-2.37 (m, 1H) 2.71-2.94 (m, 1H) 3.21 (d, J=6.65 Hz, 3H) 3.32-3.51 (m, 1H) 3.69-3.92 (m, 1H) 4.08-4.24 (m, 1H) 4.75-4.88 (m, 1H) 4.89-5.17 (m, 1H) 6.29-6.49 (m, 1H) 7.32 (d, J=8.99 Hz, 2H) 7.59 (s, 1H) 7.78-8.10 (m, 3H) 8.80 (t, J=2.54 Hz, 1H) 10.05-10.28 (m, 1H).

Stage 2.2: (R)-5-Bromo-6-(3-hydroxypyrrolidin-1-yl)-N-(4-(trifluoromethoxy)phenyl)nicotinamide

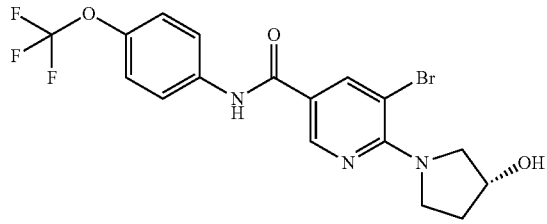 [SMILES: O=C(Nc1ccc(OC(F)(F)F)cc1)c1cnc(N2CC[C@@H](O)C2)c(Br)c1]

(R)-Pyrrolidin-3-ol (17.1 ml, 211.2 mmol) and DIPEA (67.6 ml, 387.6 mmol) were added to a suspension of 5-bromo-6-chloro-N-(4-(trifluoromethoxy)phenyl)nicotinamide (Stage 2.3, 69.6 g, 175.9 mmol) in iPrOH (120 mL) and stirred at 140° C. for 1 h. The mixture was diluted with EtOAc (1 L), washed with 1N HCl (2×200 mL), a sat. solution of NaHCO₃ (200 mL) and brine (2×200 mL) and dried over Na₂SO₄. The solvent was evaporated off under reduced pressure and the product was crystallized from EtOAc/iPr₂O to afford the title compound as a white crystalline solid. HPLC (Condition 5) t_R=6.58 min, UPLC-MS (Condition 6) m/z=446.0/448.0 [M+H]⁺; ¹H-NMR (400 MHz, DMSO-d₆) δ ppm 1.78-2.01 (m, 2H) 3.55 (d, J=11.34 Hz, 1H) 3.64-3.76 (m, 1H) 3.79-3.91 (m, 2H) 4.33 (br. s, 1H) 4.97 (d, J=3.13 Hz, 1H) 7.33 (d, J=9.38 Hz, 2H) 7.83 (d, J=8.99 Hz, 2H) 8.30-8.36 (m, 1H) 8.66 (d, J=2.35 Hz, 1H) 10.20 (s, 1H).

Stage 2.3: 5-Bromo-6-chloro-N-(4-(trifluoromethoxy)phenyl)nicotinamide

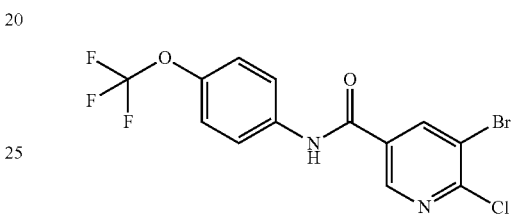

A stirred solution of 5-bromo-6-chloro-nicotinic acid (375 g, 1.586 mol) and DMF (37 mL) in toluene (3.1 L) was treated dropwise with SOCl₂ (347 mL, 4.758 mol) at RT and then stirred at 85° C. for 2.5 h. The solvent was evaporated off under reduced pressure and the residue was dissolved in THF (3.1 L), cooled to −25° C., treated firstly with DIPEA (543 mL, 3.172 mol) and then by the dropwise addition of a solution of 4-(trifluoromethoxy)aniline (295 g, 1.665 mol) in THF (3.1 L), After 30 min at 10° C. the solvent was evaporated off under reduced pressure and the residue was dissolved in TBME (4 L), washed with 1N HCl (2×1 L), a sat. solution of NaHCO₃ (1 L) and brine (2×200 mL) and dried over Na₂SO₄. The solvent was evaporated off under reduced pressure and the product was crystallized from EtOAc/n-heptane to give the title compound as a beige crystalline solid. UPLC-MS (Condition 3) t_R=1.25 min, m/z=393/395/397 [M−H]⁻; ¹H-NMR (400 MHz, DMSO-d₆) δ ppm 7.40 (d, J=8.60 Hz, 2H) 7.86 (d, J=8.60 Hz, 2H) 8.73 (d, J=2.20 Hz, 1H) 8.92 (d, J=2.20 Hz, 1H) 10.69 (s, 1H).

Example 3

(R)-6-(3-Hydroxypyrrolidin-1-yl)-5-(3-methyl-1H-pyrazol-5-yl)-N-(4-(trifluoromethoxy)phenyl)nicotinamide

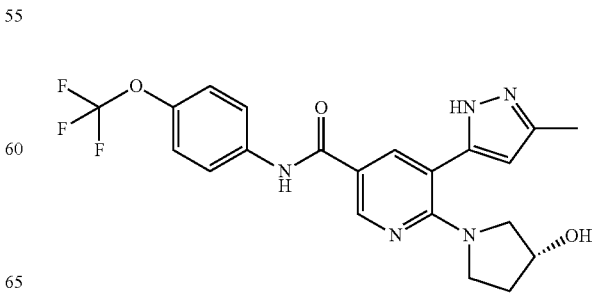

(R,E)-6-(3-Hydroxypyrrolidin-1-yl)-5-(3-oxobut-1-en-1-yl)-N-(4-(trifluoromethoxy)phenyl)nicotinamide (Stage 3.1, 50 mg, 0.091 mmol) and toluene-4-sulfonic acid hydrazide (34.5 mg, 0.181 mmol) and EtOH (302 µL) were added to a MW vial, which was sealed and stirred at 80° C. for 1.5 h. The mixture was cooled to RT, NaOMe (17.15 mg, 0.318 mmol) was added and the RM was stirred at 80° C. for 48 h. Aq. The RM was acidified with aq. formic acid, filtered through a 0.2 µM PTFE membrane filter and purified by preparative HPLC (Condition 9, from 20% to 50% in 18 min) to yield the title compound as a white solid. UPLC-MS (Condition 1) $t_R$=2.08 min, m/z=448.0 [M+H]$^+$, m/z=446.0 [M−H]$^-$; $^1$H-NMR (400 MHz, DMSO-d$_6$) δ ppm 1.68-1.79 (m, 1H) 1.78-1.90 (m, 1H) 2.29 (br. s, 3H) 2.98 (d, J=11.74 Hz, 1H) 3.25-3.37 (m, 2H) 3.40-3.53 (m, 1H) 4.21 (br. s, 1H) 4.83 (br. s, 1H) 6.13 (s, 1H) 7.33 (d, J=8.31 Hz, 2H) 7.86 (d, 2H) 8.01 (br. s, 1H) 8.71 (br. s, 1H) 10.15 (s, 1H) 12.57 (br. s, 1H).

Stage 3.1: (R,E)-6-(3-Hydroxypyrrolidin-1-yl)-5-(3-oxobut-1-en-1-yl)-N-(4-(trifluoromethoxy)phenyl)nicotinamide

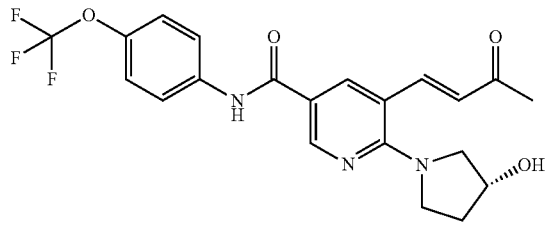 [SMILES: CC(=O)/C=C/c1cc(C(=O)Nc2ccc(OC(F)(F)F)cc2)cnc1N1CC[C@@H](O)C1]

(R)-5-Bromo-6-(3-hydroxypyrrolidin-1-yl)-N-(4-(trifluoromethoxy)phenyl)nicotinamide (Stage 2.2, 250 mg, 0.560 mmol), Pd(OAc)$_2$ (3.77 mg, 0.017 mmol), tri-o-tolylphosphine (20.46 mg, 0.067 mmol), but-3-en-2-one (55.1 µL, 0.672 mmol) and TEA (102 µL, 0.728 mmol) were added to a MW vial, which was sealed and purged with argon. DMF (1.87 mL) was added and the RM was stirred at 130° C. for 6 h. Additional but-3-en-2-one (22.96 µL, 0.280 mmol) was then added and mixture was stirred at 130° C. for 16 h. The RM was poured into water (25 mL) and extracted with DCM (3×20 mL). The combined extracts were dried over MgSO$_4$ and the solvent was evaporated off under reduced pressure to give the crude product which was purified by flash chromatography (RediSep® Silica gel column, 12 g, cyclohexane/EtOAc-EtOH+0.1% NH$_4$OH (9:1) from 40% to 75% EtOAc-EtOH+0.1% NH$_4$OH (9:1)). Fractions containing pure product were combined and the solvent was evaporated off under reduced pressure to give a residue which was azeotroped with xylene and triturated in cyclohexane to yield the title compound as a yellow solid. UPLC-MS (Condition 1) $t_R$=2.39 min, m/z=436.0 [M+H]$^+$, m/z=434.0 [M−H]$^-$; $^1$H-NMR (400 MHz, DMSO-d$_6$) δ ppm 1.82-1.91 (m, 1H) 1.91-2.00 (m, 1H) 2.35 (s, 3H) 3.43 (d, J=11.25 Hz, 1H) 3.59-3.67 (m, 1H) 3.78-3.88 (m, 2H) 4.34 (br. s, 1H) 4.99 (d, J=3.18 Hz, 1H) 6.61 (d, J=15.89 Hz, 1H) 7.36 (d, J=8.31 Hz, 2H) 7.81-7.93 (m, J=16.14, 9.29 Hz, 3H) 8.29 (d, J=2.20 Hz, 1H) 8.71 (d, J=2.45 Hz, 1H) 10.21 (s, 1H).

Example 4

(R)-6-(3-Hydroxypyrrolidin-1-yl)-5-(4-methyl-1H-pyrazol-5-yl)-N-(4-(trifluoromethoxy)phenyl)nicotinamide

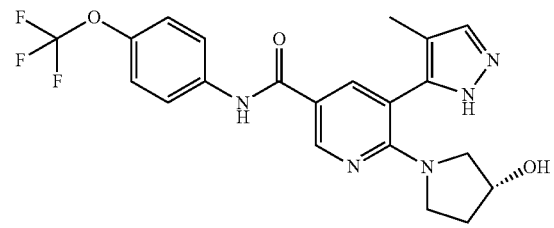 [SMILES: Cc1cn[nH]c1-c1cc(C(=O)Nc2ccc(OC(F)(F)F)cc2)cnc1N1CC[C@@H](O)C1]

DIPEA (43.9 µL, 0.252 mmol) was added to a solution of 6-chloro-5-(4-methyl-1-(tetrahydro-2H-pyran-2-yl)-1H-pyrazol-5-yl)-N-(4-(trifluoromethoxy)phenyl)nicotinamide (Stage 4.1, 55 mg, 0114 mmol) and (R)-pyrrolidin-3-ol (11.96 mg, 0.137 mmol) in iPrOH (114 µL) in a vial, which was sealed and heated at 140° C. for 18 h. After cooling to RT, the RM was dissolved in EtOAc, washed with brine, dried over Na$_2$SO$_4$ and the solvent was evaporated off under reduced pressure and the crude product was purified by flash chromatography (RediSep® Silica gel column, EtOAc/MeOH 98:2) to afford 6-((R)-3-hydroxypyrrolidin-1-yl)-5-(4-methyl-1-(tetrahydro-2H-pyran-2-yl)-1H-pyrazol-5-yl)-N-(4-(trifluoromethoxy)phenyl)nicotinamide as an off-white foam. This intermediate (39 mg, 0.073 mmol) was dissolved in DCM (0.8 mL), treated with TFA (0.262 mL, 3.4 mmol) and stirred at RT for 3 h. The RM was poured into 25 mL Na$_2$CO$_3$ 10% and extracted with EtOAc. The combined extracts were dried over Na$_2$SO$_4$ and the solvent was evaporated off under reduced pressure and the crude product was purified by flash chromatography (RediSep® Silica gel column, DCM/MeOH from 2% to 10% MeOH) to afford the title compound as an off-white powder. HPLC (Condition 4) $t_R$=4.46 min, UPLC-MS (Condition 3) $t_R$=0.92 min, m/z=448.4 [M+H]$^+$; $^1$H-NMR (400 MHz, DMSO-d$_6$) δ ppm 1.64-1.81 (m, 2H) 1.86 (s, 3H) 2.78-2.97 (m, 1H) 3.07-3.41 (m, 3H) 4.18 (br. s, 1H) 4.81 (br. s, 1H) 7.32 (d, J=8.60 Hz, 2H) 7.58 (br. s, 1H) 7.85 (d, J=9.38 Hz, 2H) 7.93 (br. s, 1H) 8.73 (br. s, 1H) 10.14 (s, 1H) 12.63 (br. s, 1H).

Stage 4.1: 6-Chloro-5-(4-methyl-1-(tetrahydro-2H-pyran-2-yl)-1H-pyrazol-5-yl)-N-(4-(trifluoromethoxy)phenyl)nicotinamide

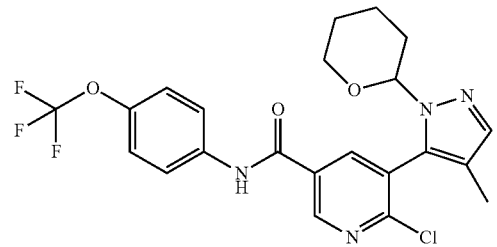 [SMILES: Cc1cnn(C2CCCCO2)c1-c1cc(C(=O)Nc2ccc(OC(F)(F)F)cc2)cnc1Cl]

K₃PO₄ (127 mg, 0.6 mmol) was added to a solution of 6-chloro-5-iodo-N-(4-(trifluoromethoxy)phenyl)nicotinamide (Stage 4.2, 89 mg, 0.2 mmol) and 4-methyl-1-(tetrahydro-2H-pyran-2-yl)-5-(4,4,5,5-tetramethyl-1,3,2-dioxaborolan-2-yl)-1H-pyrazole (58.4 mg, 0.2 mmol) in dioxane (1 mL) in a vial which was flushed with argon, heated to 110° C. and then PdCl₂(dppf) (7.32 mg, 0.01 mmol) was added. The vial was sealed and the RM was stirred under argon at 110° C. for 18 h. The RM was cooled to RT, dissolved in EtOAc and washed with brine. The organic phase was dried over Na₂SO₄ and the solvent was evaporated off under reduced pressure. and the residue was purified by flash chromatography (RediSep® Silica gel column, n-heptane/EtOAc form 50% to 100% EtOAc) to afford the title compound as a white foam. HPLC (Condition 4) $t_R$=6.24 min, UPLC-MS (Condition 3) $t_R$=1.22 min, m/z=481.2 [M+H]⁺.

Stage 4.2: 6-Chloro-5-iodo-N-(4-(trifluoromethoxy)phenyl)nicotinamide

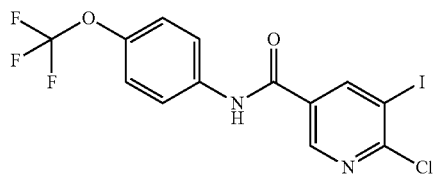 [SMILES: O=C(Nc1ccc(OC(F)(F)F)cc1)c1cnc(Cl)c(I)c1]

DMF (0.13 mL) and SOCl₂ (0.734 mL, 10.05 mmol) were added to a mixture of 6-chloro-5-iodonicotinic acid (1.00 g, 3.35 mmol) and 4-(trifluoromethoxy)aniline (0.623 mg, 3.52 mmol) in toluene (7 mL) and the RM was stirred at 80° C. for 1 h. The solvent was evaporated off under reduced pressure and under argon the residue was dissolved in THF (7.00 mL) and DIPEA (1.17 mL, 6.7 mmol), cooled to −15° C. treated dropwise with a solution of 4-(trifluoromethoxy)aniline (0.476 mL, 3.52 mmol) in THF (7.00 mL) and stirred at RT for 1 h. The solvent was evaporated off under reduced pressure and the residue treated with aq. 1N HCl (30 mL) and extracted with TBME (100 mL). The combined extracts were washed with sat. aq. Na₂CO₃ (30 mL) and brine (30 mL), dried over Na₂SO₄ and the solvent was evaporated off under reduced pressure until crystallization commenced. The product was triturated with n-heptane, filtered and dried to afford the title compound as an off-white solid. HPLC (Condition 4) $t_R$=6.36 min, UPLC-MS (Condition 3) $t_R$=1.23 min, m/z=441.1 [M−H]⁻.

Example 5

(R)-5-(4-Fluoro-1H-pyrazol-5-yl)-6-(3-hydroxypyrrolidin-1-yl)-N-(4-(trifluoromethoxy)phenyl)nicotinamide

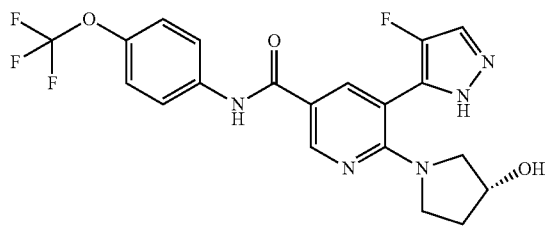 [SMILES: O=C(Nc1ccc(OC(F)(F)F)cc1)c1cnc(N2CC[C@@H](O)C2)c(-c2[nH]ncc2F)c1]

DIPEA (71.9 µL, 0.412 mmol) was added to a solution of 6-chloro-5-(4-fluoro-1H-pyrazol-5-yl)-N-(4-(trifluoromethoxy)phenyl)nicotinamide (Stage 5.1, 75 mg, 0.187 mmol) and (R)-pyrrolidin-3-ol (19.97 mg, 0.225 mmol) in iPrOH (187 µL) in a vial which was sealed and heated at 140° C. for 1 h. After cooling at RT, the RM was dissolved in EtOAc and washed with brine, dried over Na₂SO₄ and the solvent was evaporated off under reduced pressure to give the crude product which was purified by flash chromatography (RediSep® Silica gel column, DCM/MeOH from 2% to 10% MeOH) to afford the title compound as a white foam. HPLC (Condition 4) $t_R$=4.73 min, UPLC-MS (Condition 3) $t_R$=0.93 min, m/z=452.4 [M+H]⁺; ¹H-NMR (400 MHz, DMSO-d₆) δ ppm 1.64-1.95 (m, 2H) 3.00 (d, J=11.34 Hz, 1H) 3.18-3.51 (m, 3H) 4.22 (br. s, 1H) 4.86 (br. s, 1H) 7.32 (d, J=8.60 Hz, 2H) 7.77-8.11 (m, 4H) 8.76 (br. s, 1H) 10.17 (s, 1H) 12.90 (br. s, 1H).

Stage 5.1: 6-Chloro-5-(4-fluoro-1H-pyrazol-5-yl)-N-(4-(trifluoromethoxy)phenyl)nicotinamide

Pd(Ph₃P)₄ (17.33 mg, 0.015 mmol) was added to solution of 6-chloro-5-iodo-N-(4-(trifluoromethoxy)phenyl)nicotinamide (Stage 4.2, 133 mg, 0.3 mmol) and 4-fluoro-5-(tributylstannyl)-1H-pyrazole (101 mg, 0.270 mmol) in DMSO (1 mL) in a vial under an argon atmosphere. The vial was sealed and the RM mixture was heated at 100° C. for 18 h. After cooling to RT, the RM was dissolved in EtOAc, washed with brine, dried over Na₂SO₄ and the solvent was evaporated off under reduced pressure to give the crude product which was purified by flash chromatography (RediSep® Silica gel column, n-heptane/EtOAc from 10% to 50% EtOAc) to afford the title compound as an off-white powder. HPLC (Condition 4) $t_R$=5.5 min, UPLC-MS (Condition 3) $t_R$=1.05 min, m/z=399.2 [M–H]⁻.

Example 6

(R)-6-(3-Hydroxypyrrolidin-1-yl)-5-(1-methyl-1H-pyrazol-4-yl)-N-(4-(trifluoromethoxy)phenyl)nicotinamide

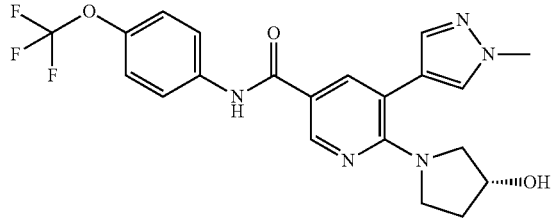 [SMILES: Cn1cc(-c2cc(C(=O)Nc3ccc(OC(F)(F)F)cc3)cnc2N2CC[C@@H](O)C2)cn1]

A mixture of (R)-5-bromo-6-(3-hydroxypyrrolidin-1-yl)-N-(4-(trifluoromethoxy)phenyl)nicotinamide (Stage 2.2, 60 mg, 0.134 mmol), 1-methyl-4-(4,4,5,5-tetramethyl-1,3,2-dioxaborolan-2-yl)-1H-pyrazole (42 mg, 0.202 mmol), Pd(PPh₃)₂Cl₂ (9.44 mg, 0.013 mmol), Na₂CO₃ (42.8 mg, 0.403 mmol), DME (570 μL), water (163 μL) and EtOH (81 μL) in a MW vial was sealed, evacuated/purge with argon and subjected to MW irradiation at 120° C. for 10 min. The RM was diluted with THF (1 mL), treated with Si-Thiol (Silicycle, 1.44 mmol/g, 46.7 mg, 0.067 mmol), filtered and the filtrate was evaporated off under reduced pressure to give a residue which was purified by preparative HPLC (Condition 9, 25% for 0.2 min then 15% to 45% in 14 min) to yield the title compound as a white solid. LC-MS (Condition 2) $t_R$=1.61 min, m/z=448.2/449.2 [M+H]⁺, m/z=446.1 [M–H]⁻; ¹H-NMR (400 MHz, DMSO-d₆) δ ppm 1.71-1.80 (m, 1H) 1.81-1.91 (m, 1H) 2.98 (d, J=11.25 Hz, 1H) 3.25-3.39 (m, 0.2H) 3.44-3.53 (m, 1H) 3.89 (s, 3H) 4.22 (s, 1H) 4.84 (s, 1H) 7.34 (d, J=8.56 Hz, 2H) 7.53 (s, 1H) 7.84 (d, J=5.38 Hz, 2H) 7.86-7.88 (m, 1H) 7.94 (d, J=2.45 Hz, 1H) 8.67 (d, J=2.45 Hz, 1H) 10.14 (s, 1H).

Example 7

(S)-6-(3-(Hydroxymethyl)pyrrolidin-1-yl)-5-(1H-pyrazol-5-yl)-N-(4-(trifluoromethoxy)phenyl)nicotinamide

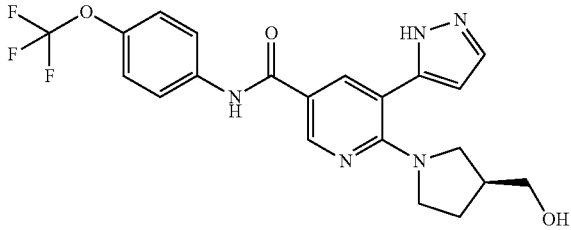 [SMILES: O=C(Nc1ccc(OC(F)(F)F)cc1)c1cnc(N2CC[C@H](CO)C2)c(-c2ccn[nH]2)c1]

The title compound was prepared in an analogous fashion to that of Example 2 using (S)-5-bromo-6-(3-(hydroxymethyl)pyrrolidin-1-yl)-N-(4-(trifluoromethoxy)phenyl)nicotinamide (Stage 7.1) and (1H-pyrazol-3-yl)boronic acid to afford a white solid. UPLC-MS (Condition 1) $t_R$=1.89 min, m/z=448.0 [M+H]⁺, m/z=446.1 [M–H]⁻; ¹H-NMR (400 MHz, DMSO-d₆) δ ppm 1.48-1.64 (m, 1H) 1.77-1.90 (m, 1H) 2.15-2.28 (m, 1H) 3.03 (dd, J=11.25, 6.85 Hz, 1H) 3.22 (br. s, 2H) 3.25-3.31 (m, 2H) 3.34-3.39 (m, 1H) 4.62 (br. s, 1H) 6.39 (br. s, 1H) 7.34 (d, J=8.56 Hz, 2H) 7.51-7.84 (m, 1H) 7.83-7.90 (m, 2H) 8.03 (s, 1H) 8.68-8.79 (m, 1H) 10.19 (s, 1H) 12.87-13.12 (m, 1H).

Stage 7.1: (S)-5-Bromo-6-(3-(hydroxymethyl)pyrrolidin-1-yl)-N-(4-(trifluoromethoxy)phenyl)nicotinamide

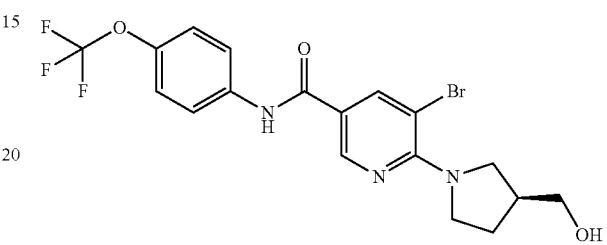

A mixture of 5-bromo-6-chloro-N-(4-(trifluoromethoxy)phenyl)nicotinamide (Stage 2.3, 500 mg, 1.264 mmol), (S)-beta-prolinol hydrochloride (226 mg, 1.643 mmol), DIPEA (662 μL, 3.79 mmol) and iPrOH (1.945 mL) in a sealed vial was subjected to MW irradiation at 140° C. for 60 min. The solvent was evaporated off under reduced pressure and the residue was treated with aq. 0.5 M HCl (20 mL) and extracted with EtOAc. The combined extracts were washed with 0.5 M HCl (10 ml) and water, dried over MgSO₄ and the solvent was evaporated off under reduced pressure to give the product which was triturated with cyclohexane, filtered and dried to afford the title compound as a white solid. UPLC-MS (Condition 1) $t_R$=2.76 min, m/z=460.0/462.0 [M+H]⁺, m/z=458.0/460.0 [M–H]⁻; ¹H-NMR (400 MHz, DMSO-d₆) δ ppm 1.59-1.76 (m, 1H) 1.92-2.04 (m, 1H) 2.26-2.44 (m, 2H) 3.37-3.50 (m, 2H) 3.56 (dd, J=11.00, 7.34 Hz, 1H) 3.67-3.85 (m, 3H) 4.71 (br. s, 1H) 7.35 (d, J=8.56 Hz, 2H) 7.85 (d, 1H) 8.34 (d, J=1.96 Hz, 1H) 8.68 (d, J=1.96 Hz, 1H) 10.21 (s, 1H).

Example 8

(S)—N-(4-(Chlorodifluoromethoxy)phenyl)-6-(3-hydroxypyrrolidin-1-yl)-5-(1H-pyrazol-5-yl)nicotinamide

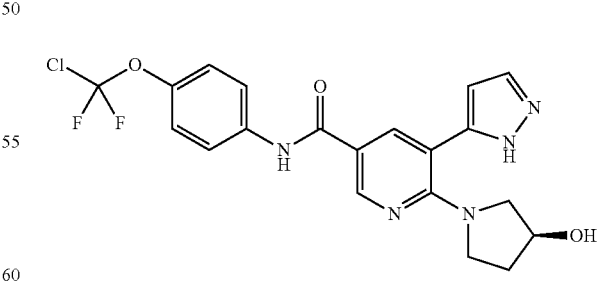

K₃PO₄ (41.3 mg, 0.195 mmol) was added to a solution of (S)-5-bromo-N-(4-(chlorodifluoromethoxy)phenyl)-6-(3-hydroxypyrrolidin-1-yl)nicotinamide (Stage 8.1, 30 mg, 0.067 mmol) and 1-(tetrahydro-2H-pyran-2-yl)-5-(4,4,5,5-tetramethyl-1,3,2-dioxaborolan-2-yl)-1H-pyrazole (36.2 mg, 0.13 mmol) in toluene (0.32 mL) in a vial which was flushed with argon. Pd(PPh$_3$)$_4$ (3.75 mg, 0.032 mmol) was added. The vial was sealed and heated at 110° C. for 18 h. After cooling at RT, the RM was dissolved in EtOAc, washed with brine, dried over Na$_2$SO$_4$ and the solvent was evaporated off under reduced pressure to give a crude product was purified by flash chromatography (RediSep® Silica gel column, DCM/MeOH from 2% to 5% MeOH) to afford N-(4-(chlorodifluoromethoxy)phenyl)-6-(S)-3-hydroxypyrrolidin-1-yl)-5-(1-(tetrahydro-2H-pyran-2-yl)-1H-pyrazol-5-yl)nicotinamide, a portion of which (21 mg, 0.039 mmol) was dissolved in DCM (0.5 mL), treated with TFA (0.141 mL, 1.82 mmol) and stirred at RT for 3 h. The RM was poured into 10% aq. Na$_2$CO$_3$ (10 mL) and extracted with EtOAc. The combined extracts were dried over Na$_2$SO$_4$ and the solvent was evaporated off under reduced pressure to give the crude product which was purified by flash chromatography (RediSep® Silica gel column, DCM/MeOH from 2% to 5% MeOH) to afford the title compound. HPLC (Condition 4) t$_R$=4.49 min, HPLC Chiral (CHIRALCEL® OD-H, 250×4.6 mm, eluent: n-heptane/EtOH/MeOH (85:10:5), 1 mL/min, UV DAD, t$_R$=13.32 min, UPLC-MS (Condition 3) t$_R$=0.92 min, m/z=450.3 [M+H]$^+$; $^1$H-NMR (400 MHz, DMSO-d$_6$) δ ppm 1.65-1.76 (m, 1H) 1.77-1.92 (m, 1H) 2.86-2.97 (m, 1H) 3.18-3.35 (m, 2H) 3.34-3.47 (m, 1H) 4.10-4.24 (m, 1H) 4.66-4.93 (m, 1H) 6.28-6.42 (m, 1H) 7.31 (d, J=8.99 Hz, 2H) 7.85 (d, J=8.99 Hz, 3H) 7.96-8.05 (m, 1H) 8.64-8.81 (m, 1H) 10.17 (s, 1H) 12.80-13.14 (m, 1H).

Stage 8.1: (S)-5-Bromo-N-(4-(chlorodifluoromethoxy)phenyl)-6-(3-hydroxypyrrolidin-1-yl)nicotinamide

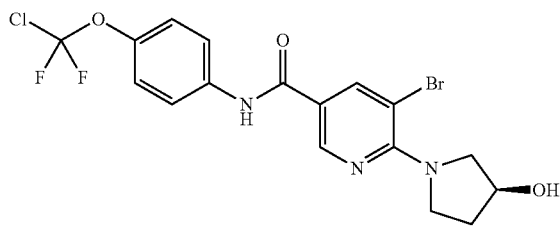 [SMILES: O=C(Nc1ccc(OC(F)(F)Cl)cc1)c1cnc(N2CC[C@H](O)C2)c(Br)c1]

DIPEA (190 µL, 1.1 mmol) was added to a solution of 5-bromo-6-chloro-N-(4-(chlorodifluoromethoxy)phenyl)nicotinamide (Stage 9.3, 206 mg, 0.5 mmol) and (S)-pyrrolidin-3-ol (52.3 mg, 0.6 mmol) in iPrOH (500 µL) in a vial, which was sealed and heated at 140° C. for 1 h. After cooling at RT, the RM was dissolved in EtOAc, washed with 0.5 M aq. HCl and brine, dried over Na$_2$SO$_4$ and the solvent was evaporated off under reduced pressure to give the crude product which was purified by flash chromatography (RediSep® Silica gel column, n-heptane/EtOAc from 20 to 100% EtOAc) to afford the title compound as a white crystalline powder. HPLC (Condition 4) t$_R$=5.59 min, UPLC-MS (Condition 3) t$_R$=1.17 min, m/z=462.0/464.1 [M+H]$^+$.

Example 9

(R)—N-(4-(Chlorodifluoromethoxy)phenyl)-6-(3-hydroxypyrrolidin-1-yl)-5-(1H-pyrazol-5-yl)nicotinamide

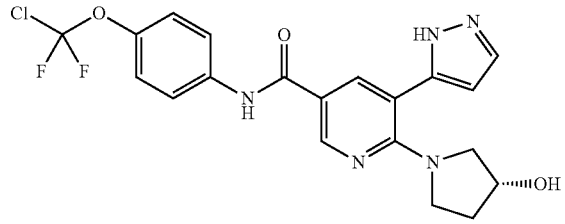 [SMILES: O=C(Nc1ccc(OC(F)(F)Cl)cc1)c1cnc(N2CC[C@@H](O)C2)c(-c2ccn[nH]2)c1]

A mixture of (R)-5-Bromo-N-(4-(chlorodifluoromethoxy)phenyl)-6-(3-hydroxypyrrolidin-1-yl)nicotinamide (Stage 9.2, 100 mg, 0.216 mmol) and 5-(4,4,5,5-tetramethyl-1,3,2-dioxaborolan-2-yl)-1-(2-(trimethylsilyl)ethoxy)methyl)-1H-pyrazole (215 mg, 0.663 mmol), Pd(PPh$_3$)$_2$Cl$_2$ (17 mg, 0.024 mmol), Na$_2$CO$_3$ (115 mg, 1.081 mmol), DME (917 µL), water (262 µL) and EtOH (131 µL) in a MW vial was sealed, evacuated/purged 3 times with argon and subjected to MW irradiation at 125° C. for 20 min. The RM was diluted with 2 mL of DME, stirred with Si-Thiol (Silicycle 1.44 mmol/g, 90 mg, 0.130 mmol) for 3 h. The mixture was centrifuged and the supernatant was filtered through a 0.45 µm PTFE filter and the solvent was evaporated off under reduced pressure. The crude product was purified by flash chromatography (RediSep® Silica gel column, 12 g, cyclohexane/EtOAc from 40% to 100% EtOAc) to afford the protected intermediate as a colorless oil. Ethylene diamine (96 µL, 1.428 mmol) and TBAF 1 M in THF (1.428 mL, 1.428 mmol) were then added and the RM was stirred at 80-85° C. for 5 days. The solvent was evaporated off under reduced pressure and the residue was dissolved in EtOAc (40 mL), washed 3 times with sat. aq. NaHCO$_3$ and brine, dried over Na$_2$SO$_4$ and The solvent was evaporated off under reduced pressure to give a residue which was purified by preparative SFC (Column DEAP, from 25% to 30% in 6 min) to yield the title compound as a white solid.

Alternatively, Example 9 was prepared by adding TFA (168 mL, 2182 mmol) to a solution of N-(4-(chlorodifluoromethoxy)phenyl)-6-(R)-3-hydroxypyrrolidin-1-yl)-5-(1-(tetrahydro-2H-pyran-2-yl)-1H-pyrazol-5-yl)nicotinamide (Stage 9.1, 31.3 g, 54.6 mmol) in DCM (600 mL). The mixture was stirred at RT for 2.5 h. The solvent was evaporated off under reduced pressure and the residue was dissolved in EtOAc (1.5 L), washed with a sat. solution of NaHCO$_3$ (3×500 mL) and brine (500 mL), dried over Na$_2$SO$_4$ and the solvent was evaporated off under reduced pressure to give a residue which was suspended in DCM (300 mL), stirred at RT for 15 min, filtered, washed with DCM (200 mL), dried and purified by chromatography (Silica gel, 1 kg, DCM/MeOH 95:5). The residue was dissolved in MeOH (500 mL) and treated with Si-Thiol (Biotage, 5.0 g, 6.5 mmol) for 16 h at 25° C. The resin was filtered off, the solvent was evaporated off under reduced pressure and the residue was crystallized from MeCN to afford the title compound as a white crystalline solid.

Alternatively, Example 9 was prepared by the dropwise addition of aqueous HCl (7.7 mL of 6M) to a solution of N-(4-(chlorodifluoromethoxy)phenyl)-6-(R)-3-hydroxypyrrolidin-1-yl)-5-(1-(tetrahydro-2H-pyran-2-yl)-1H-pyrazol-5-yl)nicotinamide (Stage 9.1, 3.8 g, 7.12 mmol) in MeOH (20 mL) and THF (10 mL) with cooling (below 35° C.). The mixture was stirred at 22° C. for 2 h and then added to cooled (10° C.) 1.2 M NaOH (22 mL). Throughout the addition the temperature was kept below 30° C. and pH was kept in the range of 9-10. The RM was then stirred for 30 min at 30° C. The solvent was evaporated off under reduced pressure, until the desired compound precipitated. The precipitate was filtered and dried to give the title compound as a yellow solid.

Analytical data for Example 9: HPLC (Condition 5) $t_R$=5.54 min, HPLC Chiral (CHIRALCEL® OD-H, 250×4.6 mm, eluent: n-heptane/EtOH/MeOH (85:10:5), 1 mL/min, UV 210 nm) $t_R$=10.17 min, UPLC-MS (condition 3) $t_R$=0.93 min, m/z=450.3 [M+H]$^+$, m/z=494.1 [M+formic acid-H]$^-$; $^1$H-NMR (400 MHz, DMSO-$d_6$) δ ppm 1.65-1.76 (m, 1H) 1.76-1.87 (m, 1H) 2.93 (d, J=11.73 Hz, 1H) 3.19-3.29 (m, 2H) 3.35-3.51 (m, 1H) 4.10-4.25 (m, 1H) 4.89 (br. s, 1H) 6.41 (br. s, 1H) 7.33 (d, J=8.50 Hz, 2H) 7.57/7.83 (br. s, 1H) 7.90 (d, J=8.50 Hz, 2H) 8.07 (br. s, 1H) 8.77 (br. s, 1H) 10.23 (s, 1H) 12.97/13.15 (br. s, 1H).

Stage 9.1: N-(4-(Chlorodifluoromethoxy)phenyl)-6-(R)-3-hydroxypyrrolidin-1-yl)-5-(1-(tetrahydro-2H-pyran-2-yl)-1H-pyrazol-5-yl)nicotinamide

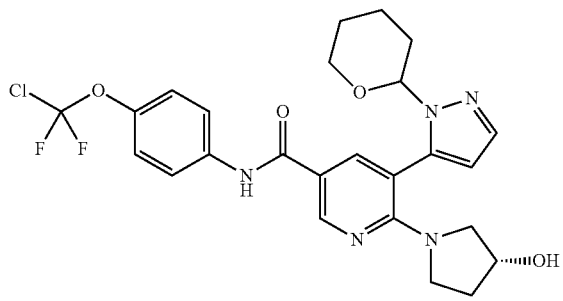 [SMILES: O=C(Nc1ccc(OC(F)(F)Cl)cc1)c1cnc(N2CC[C@@H](O)C2)c(-c2ccnn2C2CCCCO2)c1]

1-(Tetrahydro-2H-pyran-2-yl)-5-(4,4,5,5-tetramethyl-1,3,2-dioxaborolan-2-yl)-1H-pyrazole (29.6 g, 102 mmol), $K_3PO_4$ (51.6 g, 236 mmol) and Pd(PPh$_3$)$_4$ (4.55 g, 3.93 mmol) were added to a suspension of (R)-5-bromo-N-(4-(chlorodifluoromethoxy)phenyl)-6-(3-hydroxypyrrolidin-1-yl)nicotinamide (Stage 9.2, 36.4 g, 79 mmol) in toluene (360 mL) under an argon atmosphere and the mixture was stirred at 110° C. for 4 h. The RM was poured into brine (500 mL) and extracted with EtOAc (2×1 L). The combined extracts were washed with brine (500 mL), dried over Na$_2$SO$_4$, and the solvent was evaporated off under reduced pressure to give a residue which was purified by chromatography (Silica gel column, 1.5 kg, DCM/MeOH 95:5) to afford a dark yellow foam, that was dissolved in MeOH/DCM (1 L of 3:1) and treated with Si-Thiol (Biotage, 35 g, 45.5 mmol) for 17 h at 30° C. The resin was filtered off, and solvent was evaporated off under reduced pressure, until the desired compound crystallized. The product was filtered washed with MeOH and dried to afford the title compound.

Alternatively, Stage 9.1 was prepared by adding 4-(chlorodifluoromethoxy)aniline (16.6 g, 84.9 mmol), NMM (21.7 g, 212.1 mmol), hydroxybenzotriazole hydrate (HOBt.H$_2$O, 11.9 g, 77.77 mmol) and 1-ethyl-3-(3-dimethylaminopropyl) carbodiimide hydrochloride (EDCI.HCl, 20.9 g, 109.0 mmol) to a solution of 6-((R)-3-hydroxypyrrolidin-1-yl)-5-(1-(tetrahydro-2H-pyran-2-yl)-1H-pyrazol-5-yl)nicotinic acid (Stage 9.4, 29.83 g, 70.7 mmol) in THF (271 mL). The mixture was stirred for 1.5 h at 25° C. and then at 65° C. for 16 h. After cooling the RM to 35° C., further EDCI.HCl (13.3 g, 69.4 mmol) was added and the RM was stirred for 1.5 h at 35° C. then again at 65° C. for 16 h. After cooling the RM to 35° C., water (150 mL) was added, the THF was removed under reduced pressure, EtOAc (180 mL) was added and the mixture was stirred for at 35° C. for 1 h. The two layers were separated and the aq. phase was then extracted with EtOAc (60 mL). The combined organic layers were washed with water (90 mL), brine (90 mL). The solvent was evaporated off under reduced pressure to give a brown solid which was purified by column chromatography (Silica gel, DCM/MeOH 40:1 to 20:1) to afford the title compound as a yellow solid.

Analytical data for Stage 9.1: HPLC (Condition 5) $t_R$=6.12 min, UPLC-MS (Condition 3) $t_R$=1.06 min, m/z=533.2 [M+H]$^+$; $^1$H-NMR (400 MHz, DMSO-$d_6$) δ ppm 1.36-2.02 (m, 7H) 2.23-2.38 (m, 1H) 3.08-3.29 (m, 2H) 3.32-3.52 (m, 2H) 3.73-3.93 (m, 1H) 4.13-4.25 (m, 1H) 4.80-4.90 (m, 1H) 4.95-5.17 (m, 1H) 6.33-6.50 (m, 1H) 7.33 (d, J=8.99 Hz, 2H) 7.61 (d, J=1.56 Hz, 1H) 7.86 (d, J=8.99 Hz, 2H) 7.97-8.11 (m, 1H) 8.82 (s, 1H) 10.13-10.25 (m, 1H).

Stage 9.2: (R)-5-Bromo-N-(4-(chlorodifluoromethoxy)phenyl)-6-(3-hydroxypyrrolidin-1-yl)nicotinamide

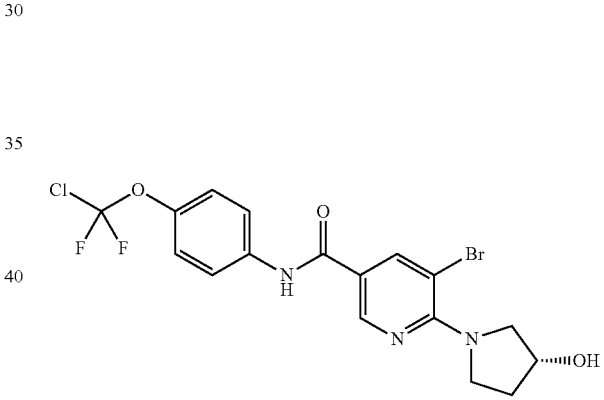

(R)-Pyrrolidin-3-ol (9.55 g, 109.6 mmol) and DIPEA (35.1 ml, 201.3 mmol) were added to a suspension of 5-bromo-6-chloro-N-(4-(chlorodifluoromethoxy)phenyl)nicotinamide (Stage 9.3, 37.7 g, 91.5 mmol) in iPrOH (65 mL) and stirred at 140° C. for 1 h. EtOAc (700 mL) was added and the solution was washed 1N HCl (2×200 mL), sat. NaHCO$_3$ (200 mL) and brine (2×200 mL), dried over Na$_2$SO$_4$, and the solution was concentrated under reduced pressure until crystallization commenced. n-Heptane (1 L) were added and the mixture was stirred at RT for 30 min, filtered and washed with iPr$_2$O (500 mL) to afford the title compound as a white crystalline solid. HPLC (Condition 5) $t_R$=6.68 min, UPLC-MS (Condition 3) $t_R$=1.10 min, m/z=462.2/464.2 [M+H]$^+$; $^1$H-NMR (400 MHz, DMSO-$d_6$) δ ppm 1.78-2.01 (m, 2H) 3.55 (d, J=11.34 Hz, 1H) 3.66-3.75 (m, 1H) 3.79-3.93 (m, 2H) 4.34 (br. s, 1H) 4.98 (d, =3.13 Hz, 1H) 7.32 (d, J=8.99 Hz, 2H) 7.84 (d, J=8.99 Hz, 2H) 8.33 (d, J=1.96 Hz, 1H) 8.66 (d, J=1.96 Hz, 1H) 10.21 (s, 1H).

Stage 9.3: 5-Bromo-6-chloro-N-(4-(chlorodifluoromethoxy)phenyl)nicotinamide

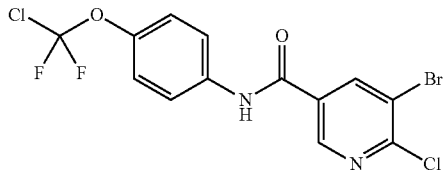

DMF (2.55 mL, 33.0 mmol) and SOCl$_2$ (24.08 ml, 330 mmol) were added to a suspension of 5-bromo-6-chloronicotinic acid (26 g, 110 mmol) in toluene (220 mL) and the RM was stirred at 80° C. for 1 h. The solvent was evaporated off under reduced pressure and the residue was dissolved in THF (220 mL) and cooled to −16° C. DIPEA (38.4 mL, 220 mmol) was added, followed by dropwise addition of a solution of 4-(chlorodifluoromethoxy)aniline (22.35 g, 115 mmol) in THF (220 mL) over 15 min. The suspension was stirred for 1 h at RT. The solvent was evaporated off under reduced pressure and the residue was dissolved in TBME (700 mL), washed with 1N HCl (2×200 mL), sat. NaHCO$_3$ (200 mL) and brine (2×200 mL), dried over Na$_2$SO$_4$, and the solvent was evaporated off under reduced pressure to give the product which was crystallized from EtOAc—n-heptane to afford the title compound as a white crystalline solid. HPLC (Condition 5) $t_R$=7.77 min, UPLC-MS (Condition 3) $t_R$=1.24 min, m/z=409.1/411.1/413.1 [M+H]$^+$; $^1$H-NMR (400 MHz, DMSO-d$_6$) δ ppm 7.38 (d, =8.99 Hz, 2H) 7.85 (d, =8.99 Hz, 2H) 8.72 (br. s, 1H) 8.92 (br. s, 1H) 10.68 (s, 1H).

Stage 9.4: 6-((R)-3-Hydroxypyrrolidin-1-yl)-5-(1-(tetrahydro-2H-pyran-2-yl)-1H-pyrazol-5-yl)nicotinic acid

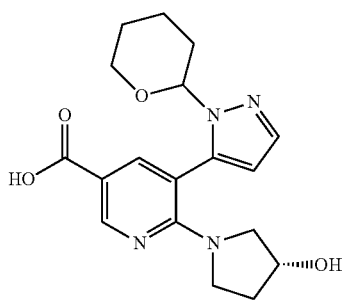 [SMILES: O=C(O)c1cnc(N2CC[C@@H](O)C2)c(-c2ccnn2C2CCCCO2)c1]

Aq. NaOH (180 mL of 2.6 M) was added to a solution of methyl 6-((R)-3-hydroxypyrrolidin-1-yl)-5-(1-(tetrahydro-2H-pyran-2-yl)-1H-pyrazol-5-yl)nicotinate (Stage 9.5, 111 g, 299 mmol) in MeOH (270 mL) and the RM was stirred at RT for 14 h. The MeOH was evaporated off under reduced pressure and the aq. residue was treated with brine (90 mL), extracted with MeTHF twice (540 mL+360 mL) and the combined organic layers were washed with water (90 mL). MeTHF was added to the combined aq. layers, the biphasic mixture was cooled to 0° C. and acidified (pH=4-4.5) with aq. HCl solution (18%) and extracted with MeTHF. The combined organic extracts were washed with brine and the solvent was evaporated off under reduced pressure to give a residue which was recrystallized from a EtOAc/TBME (1:1) to afford the title compound as a white solid. HPLC (Condition 7) $t_R$=4.74 min, LC-MS (Condition 8) $t_R$=3.37 min, m/z=359.0 [M+H]$^+$; $^1$H-NMR (400 MHz, DMSO-d$_6$) δ ppm 1.44 (br. s, 2H), 1.51 (d, J=11.54 Hz, 2H), 1.64-1.86 (m, 4H), 1.90 (br. s, 1H), 2.31 (d, J=9.29 Hz, 1H), 2.77 (br. s, 1H), 3.10 (br. s, 1H), 3.21 (d, J=8.78 Hz, 2H), 3.27-3.51 (m, 4H), 3.87 (d, J=11.54 Hz, 1H), 4.16 (br. s, 1H), 4.75-4.93 (m, 1H), 5.04 (br. s, 1H), 6.35 (d, J=17.32 Hz, 1H), 7.51-7.64 (m, 1H), 7.64-7.82 (m, 1H), 8.67 (d, J=2.26 Hz, 1H), 12.58 (br. s, 1H).

Stage 9.5: Methyl 6-((R)-3-hydroxypyrrolidin-1-yl)-5-(1-(tetrahydro-2H-pyran-2-yl)-1H-pyrazol-5-yl)nicotinate

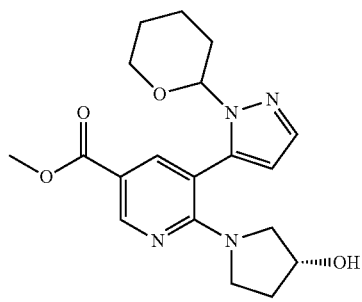 [SMILES: COC(=O)c1cnc(N2CC[C@@H](O)C2)c(-c2ccnn2C2CCCCO2)c1]

A mixture of (R)-methyl 5-bromo-6-(3-hydroxypyrrolidin-1-yl)nicotinate (Stage 9.6, 90 g, 299 mmol), 1-(tetrahydro-2H-pyran-2-yl)-1H-pyrazole-5-boronic acid pinacol ester (103.9 g, 373.6 mmol), K$_3$PO$_4$ (126.9 g, 597.7 mmol), Pd(PPh$_3$)$_2$Cl$_2$ (6.29 g, 8.97 mmol) in toluene (900 mL) was stirred at 92° C. and for 16 h. After cooling the mixture to RT, the solution was washed with water (450 mL), 5% NaHCO$_3$ solution (430 mL) and the solvent was evaporated off under reduced pressure to give a residue which was used without further purifications in the next step. HPLC (Condition 7) $t_R$=6.929 min, LC-MS (Condition 8) $t_R$=4.30 min, m/z=373.0 [M+H]$^+$; $^1$H-NMR (400 MHz, DMSO-d$_6$) δ ppm 1.19-1.28 (m, 1H), 1.35-1.63 (m, 4H), 1.63-1.86 (m, 3H), 1.89 (br. s, 1H), 2.12-2.39 (m, 1H), 3.11 (br. s, 1H), 3.18-3.48 (m, 4H), 3.78 (s, 4H), 3.88 (d, J=11.54 Hz, 1H), 4.08-4.24 (m, 1H), 4.86 (dd, J=18.20, 2.89 Hz, 1H), 5.02 (d, J=8.28 Hz, 1H), 6.39 (br. s, 1H), 7.58 (d, J=1.25 Hz, 1H), 7.78 (br. s, 1H), 8.69 (t, J=2.01 Hz, 1H).

Stage 9.6: (R)-methyl 5-bromo-6-(3-hydroxypyrrolidin-1-yl)nicotinate

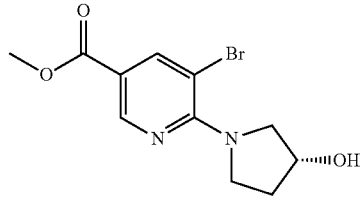 [SMILES: COC(=O)c1cnc(N2CC[C@@H](O)C2)c(Br)c1]

DIPEA (105.3 g, 142.2 mL, 814.4 mmol) was added to a solution of methyl-5-bromo-6-chroronicotinate (85 g, 339.5 mmol) and (R)-pyrrolidin-3-ol (54.2 g, 441.2 mmol) in isopropyl acetate and the RM was stirred at 70° C. for 14 h. The solvent was evaporated off under reduced pressure to give a the residue which was dissolved in toluene (850 mL), washed with water (127 mL) and brine (127 mL) and concentrated under reduced pressure until precipitation commenced. n-Heptane (340 mL) was slowly added to the stirred mixture at 22° C., which was then cooled to 0° C. and the product was filtered, washed with a toluene/n-heptane mixture (1:1.5) and dried to give the title compound as a yellow solid. HPLC (Condition 7) $t_R$=8.54 min, LC-MS (Condition 8) $t_R$=4.62 min, m/z=300.9/302.9 [M+H]$^+$; $^1$H-NMR (400 MHz, DMSO-d$_6$) δ ppm 1.77-1.99 (m, 2H), 3.57 (d, J=11.54 Hz, 1H), 3.72 (ddd, J=11.11, 7.97, 3.26 Hz, 1H), 3.78 (s, 3H), 3.81-3.90 (m, 2H), 4.26-4.39 (m, 1H), 4.99 (br. s, 1H), 8.11 (d, J=2.01 Hz, 1H), 8.56 (d, J=1.76 Hz, 1H).

Example 10

(S)—N-(4-(Chlorodifluoromethoxy)phenyl)-6-(3-(hydroxymethyl)pyrrolidin-1-yl)-5-(1H-pyrazol-5-yl)nicotinamide

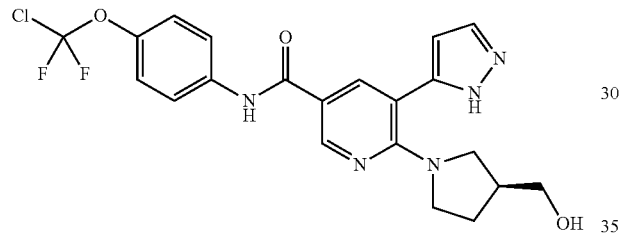

A mixture of (S)-5-bromo-N-(4-(chlorodifluoromethoxy)phenyl)-6-(3-(hydroxymethyl)pyrrolidin-1-yl)nicotinamide (Stage 10.1, 119 mg, 0.25 mmol), 1-(tetrahydro-2H-pyran-2-yl)-5-(4,4,5,5-tetramethyl-1,3,2-dioxaborolan-2-yl)-1H-pyrazole (139 mg, 0.5 mmol), Pd(PPh$_3$)$_2$Cl$_2$ (0.018 g, 0.025 mmol), Na$_2$CO$_3$ (0.106 g, 1.000 mmol), DME (1.061 mL), water (0.303 mL) and EtOH (0.152 mL) were added to a MW vial which was sealed, evacuated/purged 3 times with argon then subjected to MW irradiation at 125° C. for 20 min. The RM was diluted with DME (2 mL) and stirred overnight with Si-Thiol (Silicycle 1.43 mmol/g, 0.105 g, 0.150 mmol). The mixture was centrifuged and the supernatant was filtered through a 0.45 μm PTFE filter and the solvent was evaporated off under reduced pressure. The crude product was purified by flash chromatography (RediSep® Silica gel column, 12 g, cyclohexane/EtOAc from 20% to 90% EtOAc) to afford the protected intermediate which was treated with a mixture of DCM (2.5 mL) and TFA (0.963 mL, 12.50 mmol) and stirred at RT for 2 h. The solvent was evaporated off under reduced pressure and the residue treated with a solution of 7 N NH$_3$ in MeOH (2 mL, 14 mmol). The solvent was evaporated off under reduced pressure and the residue was purified by preparative SFC (Column DEAP, isocratic 28% in 9 min) to afford the title compound as a yellow oil. UPLC-MS (Condition 1) $t_R$=1.87 min, m/z=464.1 [M+H]$^+$, m/z=462.1 [M–H]$^-$; $^1$H-NMR (400 MHz, DMSO-d$_6$) δ ppm 1.49-1.65 (m, 1H) 1.75-1.97 (m, 1H) 2.14-2.30 (m, 1H) 3.04 (dd, J=11.37, 6.97 Hz, 1H) 3.14-3.26 (m, 2H) 3.26-3.29 (m, 1H) 3.35-3.46 (m, 2H) 4.60 (t, J=5.14 Hz, 1H) 6.39 (d, J=1.96 Hz, 1H) 7.33 (d, J=9.05 Hz, 2H) 7.76 (br. s, 1H) 7.84-7.94 (m, 2H) 8.04 (d, J=2.45 Hz, 1H) 8.74 (s, 1H) 10.18 (s, 1H) 12.87 (br. s, 1H).

Stage 10.1: (S)-5-Bromo-N-(4-(chlorodifluoromethoxy)phenyl)-6-(3-(hydroxymethyl)pyrrolidin-1-yl)nicotinamide

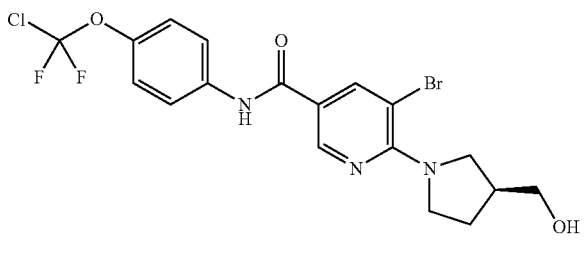 [SMILES: O=C(Nc1ccc(OC(F)(F)Cl)cc1)c1cnc(N2CC[C@H](CO)C2)c(Br)c1]

The title compound was prepared in an analogous fashion to that described in Stage 9.2 using 5-bromo-6-chloro-N-(4-(chlorodifluoromethoxy)phenyl)nicotinamide (Stage 9.3) and (S)-1-pyrrolidin-3-yl-methanol to afford an off-white crystalline solid. HPLC (Condition 4) $t_R$5.82 min, UPLC-MS (Condition 3) $t_R$=1.14 min, m/z=476.2/478.3 [M+H]$^+$.

Example 11

(R)-6-(3-Hydroxypyrrolidin-1-yl)-5-(1H-pyrazol-5-yl)-N-(4-((trifluoromethyl)thio)phenyl)nicotinamide

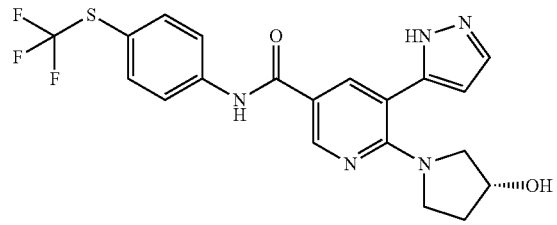 [SMILES: O=C(Nc1ccc(SC(F)(F)F)cc1)c1cnc(N2CC[C@@H](O)C2)c(-c2ccn[nH]2)c1]

The title compound was prepared in an analogous fashion to that described in Example 9 using (R)-5-bromo-6-(3-hydroxypyrrolidin-1-yl)-N-(4-((trifluoromethyl)thio)phenyl)nicotinamide (Stage 11.1) and 5-(4,4,5,5-tetramethyl-1,3,2-dioxaborolan-2-yl)-1-(2-(trimethylsilyl)ethoxy)methyl)-1H-pyrazole to afford a white solid. UPLC-MS (Condition 3) $t_R$=0.97 min, m/z=450.2 [M+H]$^+$, m/z=448.1 [M–H]$^-$; $^1$H-NMR (400 MHz, DMSO-d$_6$) δ ppm 1.67-1.78 (m, 1H) 1.78-1.88 (m, 1H) 2.94 (d, J=11.92 Hz, 1H) 3.19-3.34 (m, 2H) 3.38-3.50 (m, 1H) 4.20 (br. s, 1H) 4.81-4.93 (m, 1H)

6.33-6.45 (m, 1H) 7.83 (m, J=113.40, 8.20 Hz, 3H) 7.93 (d, J=8.66 Hz, 2H) 7.99-8.08 (m, 1H) 8.70-8.81 (m, 1H) 10.30 (s, 1H) 12.90-13.16 (m, 1H).

Stage 11.1: (R)-5-Bromo-6-(3-hydroxypyrrolidin-1-yl)-N-(4-((trifluoromethyl)thio)phenyl)nicotinamide

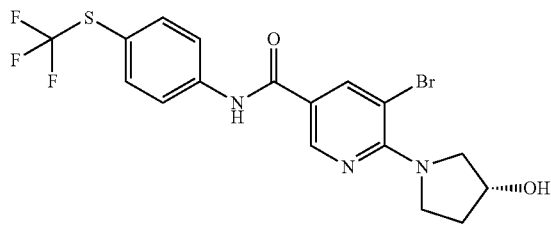 [SMILES: O=C(Nc1ccc(SC(F)(F)F)cc1)c1cnc(N2CC[C@@H](O)C2)c(Br)c1]

DIPEA (73 µL, 0.42 mmol) was added to a solution of 5-bromo-6-chloro-N-(4-((trifluoromethyl)thio)phenyl)nicotinamide (Stage 11.2, 123 mg, 0.3 mmol) and (R)-pyrrolidin-3-ol (31.4 mg, 0.36 mmol) in iPrOH (300 µL) in a vial, which was sealed and heated at 140° C. for 1 h. After cooling at RT, the RM was diluted with EtOAc, washed with brine, dried over $Na_2SO_4$ and the solvent evaporated off under reduced pressure to give a residue which was triturated with $iPr_2O$, filtered and dried to afford the title compound as a white crystalline powder. HPLC (Condition 4) $t_R$=5.9 min, UPLC-MS (Condition 3) $t_R$=1.21 min, m/z=464.1 [M+H]$^+$.

Stage 11.2: 5-Bromo-6-chloro-N-(4-((trifluoromethyl)thio)phenyl)nicotinamide

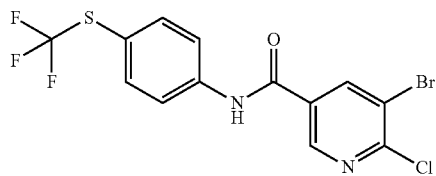

DMF (0.12 mL) was added followed by slow addition of $SOCl_2$ (0.73 mL, 10 mmol) to a mixture of 5-bromo-6-chloro-nicotinic acid (473 mg, 2 mmol) in toluene (5 mL), and the RM was then stirred at 80° C. for 1 h. After cooling at RT, the toluene was evaporated off under reduce pressure and the residue was dissolved in THF (0.4 mL). DIPEA (0.7 mL, 4 mmol) was added and the solution was cooled to 0° C. under nitrogen. 4-trifluoromethylsulfanyl-aniline (438 mg, 2.2 mmol) in THF (1 mL) was then added dropwise and the RM was stirred at 0° C. for 2 h. The RM was diluted with TBME (50 mL), treated with 1 M HCl and extracted with TBME. The combined extracts were washed with 1 M aq. NaOH and brine, dried over $Na_2SO_4$ and the solvent was evaporated off under reduced pressure and the product was crystallized from TBME/n-hexane to give the title compound as an off-white crystalline powder. HPLC (Condition 4) $t_R$=6.63 min, UPLC-MS (Condition 3) $t_R$=1.33 min, m/z=411.1 [M+H]$^+$.

Example 12

(S)-6-(3-(Hydroxymethyl)pyrrolidin-1-yl)-5-(1H-pyrazol-5-yl)-N-(4-((trifluoromethyl)thio)phenyl)nicotinamide

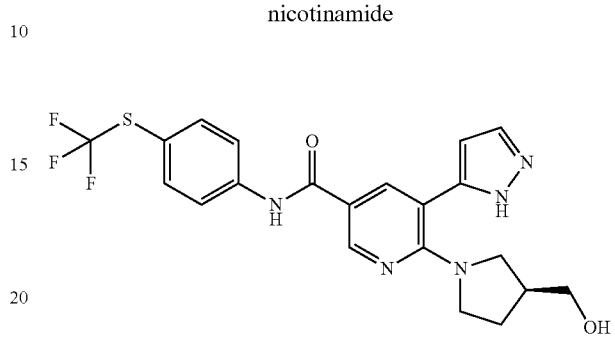

The title compound was prepared in an analogous fashion to that described in Example 10 using (S)-5-bromo-6-(3-(hydroxymethyl)pyrrolidin-1-yl)-N-(4-((trifluoromethyl)thio)phenyl)nicotinamide (Stage 12.1) and 1-(tetrahydro-2H-pyran-2-yl)-5-(4,4,5,5-tetramethyl-1,3,2-dioxaborolan-2-yl)-1H-pyrazole to afford a pale yellow powder. UPLC-MS (Condition 3) $t_R$=0.99 min, m/z=464.2 [M+H]$^+$, m/z=462.2 [M−H]$^-$; $^1$H-NMR (400 MHz, DMSO-d$_6$) d ppm 1.48-1.64 (m, 1H) 1.76-1.93 (m, 1H) 2.15-2.27 (m, 1H) 3.04 (dd, J=11.49, 7.09 Hz, 1H) 3.18-3.26 (m, 2H) 3.27-3.29 (m, 1H) 3.32-3.41 (m, 2H) 4.60 (br. s, 1H) 6.39 (d, J=1.71 Hz, 1H) 7.67 (d, J=8.56 Hz, 2H) 7.80 (br. s, 1H) 7.87-7.99 (m, 2H) 8.04 (d, J=2.45 Hz, 1H) 8.74 (br. s, 1H) 10.28 (s, 1H) 12.76-13.20 (m, 1H).

Stage 12.1: (S)-5-Bromo-6-(3-(hydroxymethyl)pyrrolidin-1-yl)-N-(4-((trifluoromethyl)thio)phenyl)nicotinamide

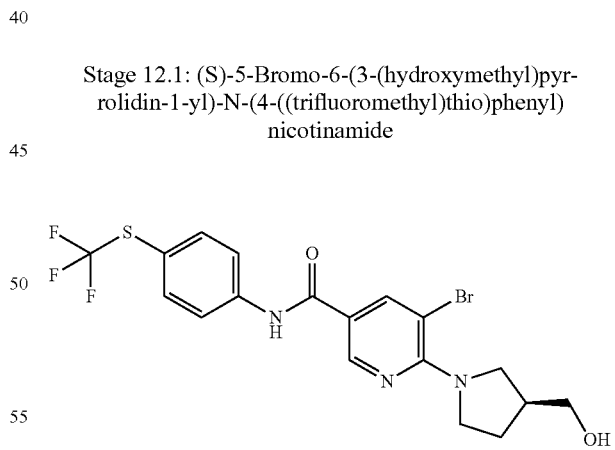

DIPEA (4.89 mL, 28.0 mmol) was added to a solution of 5-bromo-6-chloro-N-(4-((trifluoromethyl)thio)phenyl)nicotinamide (Stage 11.2, 2.88 g, 7.0 mmol) and (S)-1-pyrrolidin-3-yl-methanol (1.156, 8.40 mmol) in iPrOH (7.0 mL) in a vial, which was sealed and then heated at 140° C. for 1 h. After cooling at RT, the RM was dissolved in EtOAc, washed with aq. 0.5 M HCl and brine, dried over $Na_2SO_4$ and the solvent was evaporated off under reduced pressure to give a residue which was triturated with $iPr_2O$, filtered and dried to give the

Example 13

(R)—N-(3-Fluoro-4-(trifluoromethoxy)phenyl)-6-(3-hydroxypyrrolidin-1-yl)-5-(1H-pyrazol-5-yl)nicotinamide

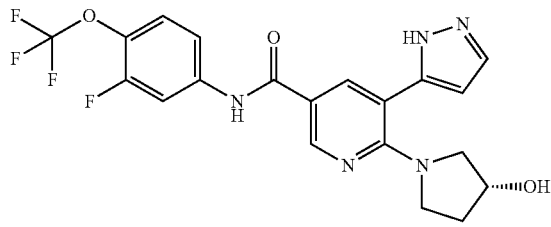 [SMILES: O=C(Nc1ccc(OC(F)(F)F)c(F)c1)c1cnc(N2CC[C@@H](O)C2)c(-c2ccn[nH]2)c1]

A mixture of (R)—N-(3-fluoro-4-(trifluoromethoxy)phenyl)-6-(3-hydroxypyrrolidin-1-yl)-5-(1-(2-(trimethylsilyl)ethoxy)methyl)-1H-pyrazol-5-yl)nicotinamide (Stage 13.1, 64 mg, 0.11 mmol), ethylene diamine (37.2 μL, 0.55 mmol) and 1 M TBAF in THF (1.651 mL, 1.651 mmol) in a MW vial was sealed and stirred at 80-85° C. for 20 h. The solvent was evaporated off under reduced pressure and the residue was dissolved in EtOAc (40 mL), washed 3 times with sat. aq. NaHCO$_3$ and brine, dried over Na$_2$SO$_4$ and the solvent was evaporated off under reduced pressure to give a crude product which was purified by preparative SFC (Column Diol, isocratic 27%) to yield the title compound as a white solid. UPLC-MS (Condition 3) t$_R$=0.95 min, m/z=452.3 [M+H]$^+$, m/z=450.3 [M−H]$^-$; $^1$H-NMR (400 MHz, DMSO-d$_6$) δ ppm 1.64-1.78 (m, 1H) 1.78-1.89 (m, 1H) 2.95 (d, J=11.74 Hz, 1H) 3.29 (br. s, 2H) 3.37-3.49 (m, 1H) 4.20 (br. s, 1H) 4.83 (br. s, 1H) 6.35-6.42 (m, 1H) 7.52 (t, J=9.05 Hz, 1H) 7.62 (d, J=9.29 Hz, 1H) 7.74 (br. s, 1H) 7.98 (dd, J=13.20, 2.20 Hz, 1H) 8.02 (d, J=2.20 Hz, 1H) 8.74 (d, J=1.71 Hz, 1H) 10.31 (br. s, 1H) 12.95 (br. s, 1H).

Stage 13.1: (R)—N-(3-Fluoro-4-(trifluoromethoxy)phenyl)-6-(3-hydroxypyrrolidin-1-yl)-5-(1-(2-(trimethylsilyl)ethoxy)methyl)-1H-pyrazol-5-yl)nicotinamide

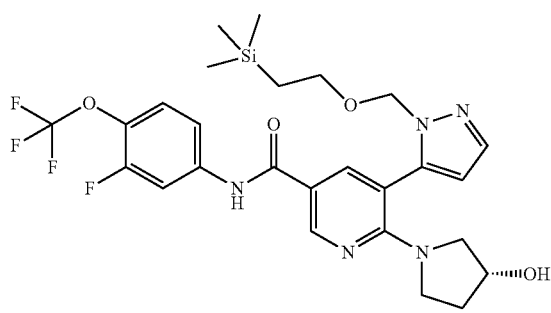 [SMILES: C[Si](C)(C)CCOCn1nccc1-c1cc(C(=O)Nc2ccc(OC(F)(F)F)c(F)c2)cnc1N1CC[C@@H](O)C1]

A mixture of (R)-5-bromo-N-(3-fluoro-4-(trifluoromethoxy)phenyl)-6-(3-hydroxypyrrolidin-1-yl)nicotinamide (Stage 13.2, 100 mg, 0.215 mmol), 5-(4,4,5,5-tetramethyl-1,3,2-dioxaborolan-2-yl)-1-(2-(trimethylsilyl)ethoxy)methyl)-1H-pyrazole (104 mg, 0.321 mmol), Pd(PPh$_3$)$_2$Cl$_2$ (15.2 mg, 0.022 mmol), Na$_2$CO$_3$ (91 mg, 0.862 mmol), DME (914 μL), water (261 μL) and EtOH (131 μL) in a MW vial was sealed, evacuated/purged 3 times with argon and subjected to MW irradiation at 125° C. for 20 min. The RM was diluted with DME (3 mL), then stirred overnight with Si-Thiol (Silicycle 1.44 mmol/g, 90 mg, 0.129 mmol). The mixture was centrifuged and the supernatant was filtered through a 0.45 μm PTFE filter and the solvent was evaporated off under reduced pressure to give a residue which was purified by preparative SFC (Column DEAP, from 15% to 20% in 6 min) to yield the title compound as a yellow transparent oil. UPLC-MS (Condition 3) t$_R$=1.28 min, m/z=581.2 [M+H]$^+$, m/z=580.4 [M−H]$^-$.

Stage 13.2: (R)-5-Bromo-N-(3-fluoro-4-(trifluoromethoxy)phenyl)-6-(3-hydroxypyrrolidin-1-yl)nicotinamide

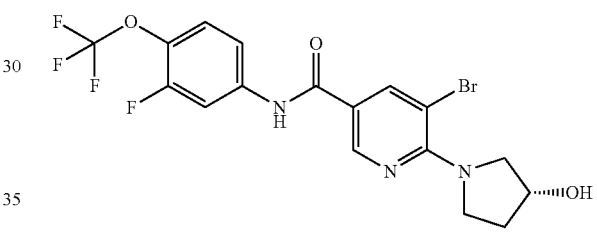

The title compound was prepared in an analogous fashion to that described in Stage 9.2 using 5-bromo-6-chloro-N-(3-fluoro-4-(trifluoromethoxy)phenyl)nicotinamide (Stage 13.3) and (R)-pyrrolidin-3-ol to afford an off-white crystalline solid. HPLC (Condition 4) t$_R$=5.82 min, UPLC-MS (Condition 3) t$_R$=1.17 min, m/z=464.1 [M+H]$^+$.

Stage 13.3: 5-Bromo-6-chloro-N-(3-fluoro-4-(trifluoromethoxy)phenyl)nicotinamide

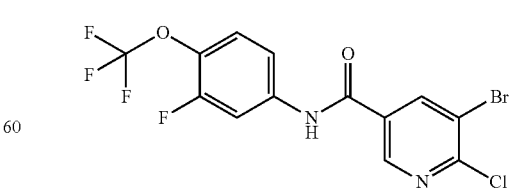

The title compound was prepared in an analogous fashion to that described in Stage 11.2 using 5-bromo-6-chloro-nicotinic acid and 3-fluoro-4-trifluoromethoxy-aniline to afford an off-white crystalline solid. HPLC (Condition 4) $t_R$=6.43 min, UPLC-MS (Condition 3) $t_R$=1.29 min, m/z=413 [M−H]⁻.

Example 14

(S)—N-(3-Fluoro-4-(trifluoromethoxy)phenyl)-6-(3-(hydroxymethyl)pyrrolidin-1-yl)-5-(1H-pyrazol-5-yl)nicotinamide

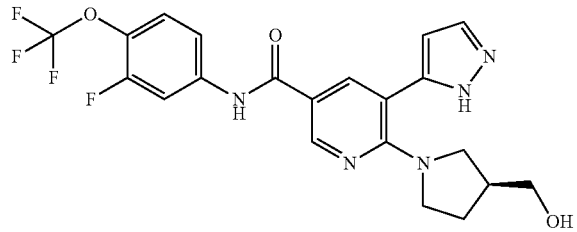 [SMILES: O=C(Nc1ccc(OC(F)(F)F)c(F)c1)c1cnc(N2CC[C@H](CO)C2)c(-c2ccn[nH]2)c1]

The title compound was prepared in an analogous fashion to that described in Example 10 using (S)-5-bromo-N-(3-fluoro-4-(trifluoromethoxy)phenyl)-6-(3-(hydroxymethyl)pyrrolidin-1-yl)nicotinamide (Stage 14.1) and 1-(tetrahydro-2H-pyran-2-yl)-5-(4,4,5,5-tetramethyl-1,3,2-dioxaborolan-2-yl)-1H-pyrazole to afford a pale yellow powder. UPLC-MS (Condition 3) $t_R$=0.96 min, m/z=466.2 [M+H]⁺, m/z=464.2 [M−H]⁻. ¹H-NMR (400 MHz, DMSO-d₆) d ppm 2.77 (s, 3H) 3.38-3.61 (m, 4H) 4.61 (br. s, 1H) 6.47 (s, 1H) 7.68 (d, J=8.56 Hz, 2H) 7.83 (br. s, 1H) 7.93 (d, J=8.80 Hz, 2H) 8.15 (br. s, 1H) 8.71 (br. s, 1H) 10.36 (s, 1H) 12.83-13.15 (m, 1H).

Stage 14.1: (S)-5-Bromo-N-(3-fluoro-4-(trifluoromethoxy)phenyl)-6-(3-(hydroxymethyl)pyrrolidin-1-yl)nicotinamide

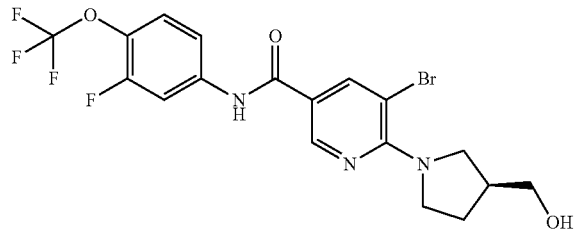 [SMILES: O=C(Nc1ccc(OC(F)(F)F)c(F)c1)c1cnc(N2CC[C@H](CO)C2)c(Br)c1]

The title compound was prepared in an analogous fashion to that described in Stage 9.2 using 5-bromo-6-chloro-N-(3-fluoro-4-(trifluoromethoxy)phenyl)nicotinamide (Stage 13.3) and (S)-1-pyrrolidin-3-yl-methanol to afford an off-white crystalline solid. HPLC (Condition 4) $t_R$=5.99 min, UPLC-MS (Condition 3) $t_R$=1.18 min, m/z=478.1/480.1 [M+H]⁺.

Example 15

(R)—N-(3-Fluoro-4-((trifluoromethyl)thio)phenyl)-6-(3-hydroxypyrrolidin-1-yl)-5-(1H-pyrazol-5-yl)nicotinamide

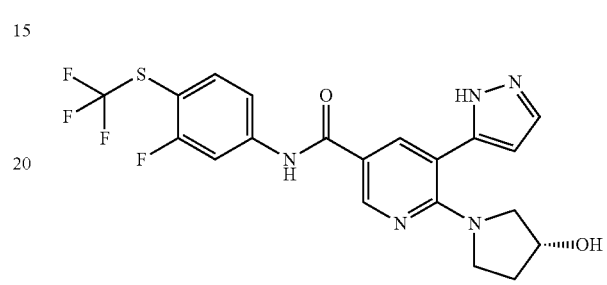

The title compound was prepared in an analogous fashion to that described in Example 13 using (R)—N-(3-fluoro-4-((trifluoromethyl)thio)phenyl)-6-(3-hydroxypyrrolidin-1-yl)-5-(1-(2-(trimethylsilyl)ethoxy)methyl)-1H-pyrazol-5-yl)nicotinamide (Stage 15.1) to afford an off-white solid. UPLC-MS (Condition 3) $t_R$=1.00 min, m/z=468.3 [M+H]⁺, m/z=466.1 [M−H]⁻; ¹H-NMR (400 MHz, DMSO-d₆) δ ppm 1.68-1.78 (m, 1H) 1.79-1.89 (m, 1H) 2.96 (d, J=11.74 Hz, 1H) 3.24-3.30 (m, 2H) 3.40-3.49 (m, 1H) 4.20 (d, J=2.20 Hz, 1H) 4.84 (br. s, 1H) 6.38 (d, J=1.96 Hz, 1H) 7.66-7.78 (m, 3H) 7.98 (dd, J=11.98, 1.96 Hz, 1H) 8.03 (d, J=2.45 Hz, 1H) 8.75 (d, J=2.45 Hz, 1H) 10.24-10.72 (m, 1H) 12.59-13.22 (m, 1H).

Stage 15.1: (R)—N-(3-Fluoro-4-((trifluoromethyl)thio)phenyl)-6-(3-hydroxypyrrolidin-1-yl)-5-(1-(2-(trimethylsilyl)ethoxy)methyl)-1H-pyrazol-5-yl)nicotinamide

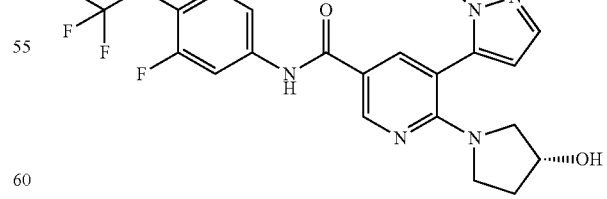

The title compound was prepared in an analogous fashion to that described in Stage 13.1 using (R)-5-bromo-N-(3-fluoro-4-((trifluoromethyl)thio)phenyl)-6-(3-hydroxypyrrolidin-1-yl)nicotinamide (Stage 15.2) and 5-(4,4,5,5-tetramethyl-1,3,2-dioxaborolan-2-yl)-1-(2-(trimethylsilyl)ethoxy)

methyl)-1H-pyrazole to afford a yellow resin. UPLC-MS (Condition 3) $t_R$=1.33 min, m/z=598.4 [M+H]$^+$, m/z=596.5 [M−H]$^−$.

Stage 15.2: (R)-5-Bromo-N-(3-fluoro-4-(((trifluoromethyl)thio)phenyl)-6-(3-hydroxypyrrolidin-1-yl)nicotinamide

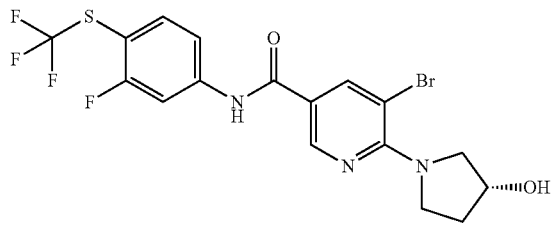 [SMILES: O=C(Nc1ccc(SC(F)(F)F)c(F)c1)c1cnc(N2CC[C@@H](O)C2)c(Br)c1]

The title compound was prepared in an analogous fashion to that described in Stage 9.2 using 5-bromo-6-chloro-N-(3-fluoro-4-((trifluoromethyl)thio)phenyl)nicotinamide (Stage 15.3) and (R)-pyrrolidin-3-ol to afford an off-white crystalline solid. HPLC (Condition 4) $t_R$=6.11 min, UPLC-MS (Condition 3) $t_R$=1.23 min, m/z=480.1 [M+H]$^+$.

Stage 15.3: 5-Bromo-6-chloro-N-(3-fluoro-4-((trifluoromethyl)thio)phenyl)nicotinamide

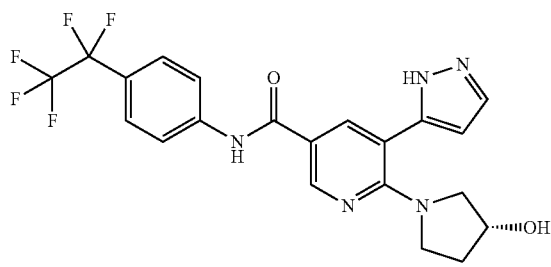 [SMILES: O=C(Nc1ccc(C(F)(F)C(F)(F)F)cc1)c1cnc(N2CC[C@@H](O)C2)c(-c2ccn[nH]2)c1]

The title compound was prepared in an analogous fashion to that described in Stage 11.2 using 5-bromo-6-chloro-nicotinic acid and 3-fluoro-4-trifluoromethylsulfanyl-aniline to afford a white crystalline solid. HPLC (Condition 4) $t_R$=6.71 min, UPLC-MS (Condition 3) $t_R$1.34 min, m/z=429 [M−H]$^−$.

Example 16

(R)-6-(3-Hydroxypyrrolidin-1-yl)-N-(4-(perfluoroethyl)phenyl)-5-(1H-pyrazol-5-yl)nicotinamide

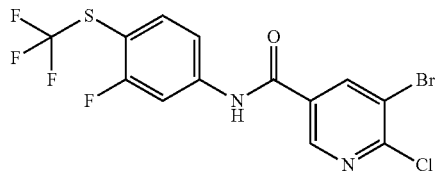

A mixture of (R)-6-(3-hydroxypyrrolidin-1-yl)-N-(4-(perfluoroethyl)phenyl)-5-(1-((2-(trimethylsilyl)ethoxy)methyl)-1H-pyrazol-5-yl)nicotinamide (Stage 16.1, 68 mg, 0.114 mmol) and ethylene damien (38.4 μL, 0.569 mmol) in a MW vial and sealed under an argon atmosphere 1 M TBAF in THF (1.707 mL, 1.707 mmol) was added and the RM was stirred at 80° C. for 20 h. The solvent was evaporated off under reduced pressure and the residue was dissolved in EtOAc (40 mL), washed 3 times with sat. aq. NaHCO$_3$ and brine, dried over Na$_2$SO$_4$ and the solvent was evaporated off under reduced pressure to give a residue which was purified by preparative SFC (Column Diol, isocratic 27% in 9 min) to afford the title compound as an off-white solid. UPLC-MS (Condition 3) $t_R$=0.98 min, m/z=468.2 [M+H]$^+$, m/z=466.2 [M−H]$^−$; $^1$H-NMR (400 MHz, DMSO-d$_6$) δ ppm 1.68-1.78 (m, 1H) 1.83 (dd, J=8.80, 4.40 Hz, 1H) 2.96 (d, J=11.74 Hz, 1H) 3.19-3.29 (m, 2H) 3.40-3.50 (m, 1H) 4.20 (br. s, 1H) 4.83 (br. s, 1H) 6.39 (d, J=1.96 Hz, 1H) 7.65 (d, J=8.80 Hz, 2H) 7.77 (br. s, 1H) 8.02 (d, J=9.05 Hz, 2H) 8.05 (d, J=2.45 Hz, 1H) 8.76 (d, J=2.20 Hz, 1H) 10.33 (s, 1H) 12.91 (br. s, 1H).

Stage 16.1: (R)-6-(3-Hydroxypyrrolidin-1-yl)-N-(4-(perfluoroethyl)phenyl)-5-(1-((2-(trimethylsilyl)ethoxy)methyl)-1H-pyrazol-5-yl)nicotinamide

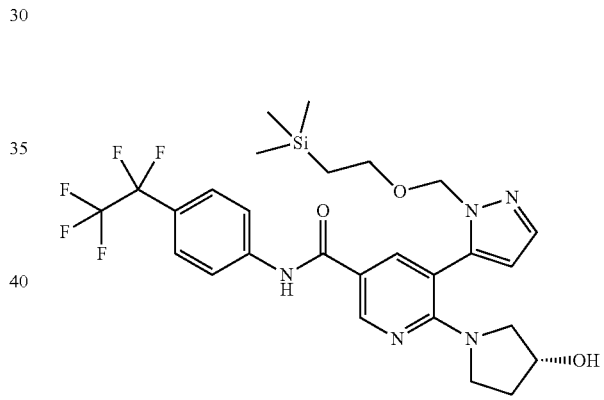

A mixture of (R)-5-bromo-6-(3-hydroxypyrrolidin-1-yl)-N-(4-(perfluoroethyl)phenyl)nicotinamide (Stage 16.2, 100 mg, 0.208 mmol), 5-(4,4,5,5-tetramethyl-1,3,2-dioxaborolan-2-yl)-1-(2-(trimethylsilyl)ethoxy)methyl)-1H-pyrazole (135 mg, 0.416 mmol), Pd(PPh$_3$)$_2$Cl$_2$ (14.62 mg, 0.021 mmol), Na$_2$CO$_3$ (88 mg, 0.833 mmol), DME (883 μL), water (252 μL) and EtOH (126 μL) in a MW vial, which was sealed, evacuated/purged 3 times with argon and subjected to MW irradiation at 125° C. for 20 min. The RM was diluted with 3 mL of DME, then stirred overnight with Si-Thiol (Silicycle 1.44 mmol/g, 87 mg, 0.125 mmol) overnight. The mixture was centrifuged and the supernatant was filtered through a 0.45 μm PTFE filter and the solvent was evaporated off under reduced pressure to give a residue which was purified by preparative SFC (Column Diol, from 15% to 20% in 6 min) to yield the title compound as a colorless transparent resin. UPLC-MS (Condition 3) $t_R$=1.31 min, m/z=598.4 [M+H]$^+$, m/z=596.3 [M−H]$^−$.

Stage 16.2: (R)-5-Bromo-6-(3-hydroxypyrrolidin-1-yl)-N-(4-(perfluoroethyl)phenyl)nicotinamide

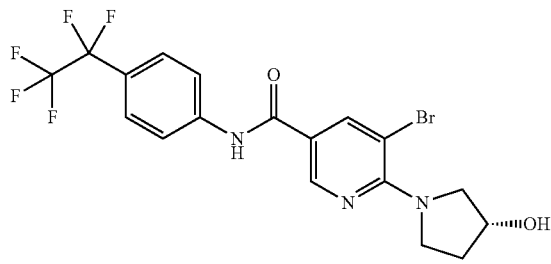 [SMILES: O=C(Nc1ccc(C(F)(F)C(F)(F)F)cc1)c1cnc(N2CC[C@@H](O)C2)c(Br)c1]

The title compound was prepared in an analogous fashion to that described in Stage 9.2 using 5-bromo-6-chloro-N-(4-(perfluoroethyl)phenyl)nicotinamide (Stage 16.3) and (R)-pyrrolidin-3-ol to afford an off-white crystalline solid. HPLC (Condition 4) $t_R$=5.96 min, UPLC-MS (Condition 3) $t_R$=1.20 min, m/z=480.2 [M+H]$^+$.

Stage 16.3: 5-Bromo-6-chloro-N-(4-(perfluoroethyl)phenyl)nicotinamide

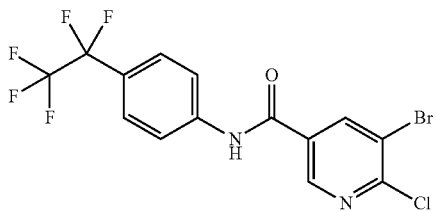 [SMILES: O=C(Nc1ccc(C(F)(F)C(F)(F)F)cc1)c1cnc(Cl)c(Br)c1]

The title compound was prepared in an analogous fashion to that described in Stage 11.2 using 5-bromo-6-chloro-nicotinic acid and 4-pentafluoroethyl-aniline to afford a white crystalline solid. HPLC (Condition 4) $t_R$=6.61 min, UPLC-MS (Condition 3) $t_R$=1.32 min, m/z=429 [M−H]$^−$.

Example 17

(R)-6-(3-Hydroxypyrrolidin-1-yl)-N-(4-(pentafluorosulfanyl)phenyl)-5-(1H-pyrazol-5-yl)nicotinamide

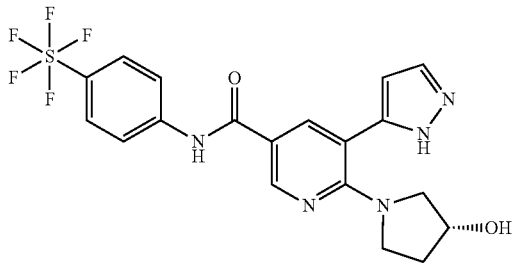 [SMILES: O=C(Nc1ccc(S(F)(F)(F)(F)F)cc1)c1cnc(N2CC[C@@H](O)C2)c(-c2ccn[nH]2)c1]

The title compound was prepared in an analogous fashion to that described in Example 8 using (R)-5-bromo-6-(3-hydroxypyrrolidin-1-yl)-N-(4-(pentafluorosulfanyl)phenyl)nicotinamide (Stage 17.1) and 1-(tetrahydro-2H-pyran-2-yl)-5-(4,4,5,5-tetramethyl-1,3,2-dioxaborolan-2-yl)-1H-pyrazole to afford a beige solid. HPLC (Condition 4) $t_R$=4.68 min, UPLC-MS (Condition 3) $t_R$=0.92 min, m/z=476.3 [M+H]$^+$; $^1$H-NMR (400 MHz, DMSO-d$_6$) δ ppm 1.64-1.91 (m, 2H) 2.93 (d, J=11.73 Hz, 1H) 3.19-3.34 (m, 2H) 3.36-3.49 (m, 1H) 4.12-4.24 (m, 1H) 4.81 (d, J=3.13 Hz, 1H) 6.38 (s, 1H) 7.73-7.89 (m, 3H) 7.92-8.09 (m, 3H) 8.73 (d, J=1.96 Hz, 1H) 10.37 (s, 1H) 12.82-13.17 (m, 1H).

Stage 17.1: (R)-5-Bromo-6-(3-hydroxypyrrolidin-1-yl)-N-(4-(pentafluorosulfanyl)phenyl)nicotinamide

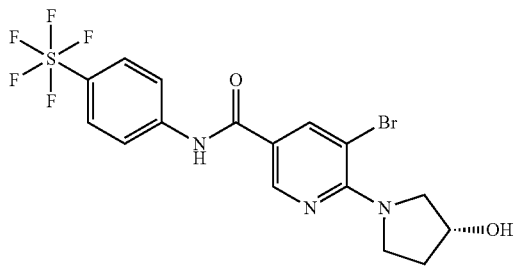 [SMILES: O=C(Nc1ccc(S(F)(F)(F)(F)F)cc1)c1cnc(N2CC[C@@H](O)C2)c(Br)c1]

The title compound was prepared in an analogous fashion to that described in Stage 9.2 using 5-bromo-6-chloro-N-(4-(pentafluorosulfanyl)phenyl)nicotinamide (Stage 17.2) and (R)-pyrrolidin-3-ol to afford a solid. UPLC-MS (Condition 3) $t_R$=1.16 min, m/z=490.1 [M+H]$^+$.

Stage 17.2: 5-Bromo-6-chloro-N-(4-(pentafluorosulfanyl)phenyl)nicotinamide

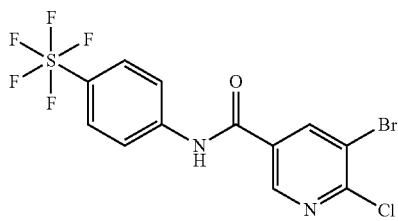 [SMILES: O=C(Nc1ccc(S(F)(F)(F)(F)F)cc1)c1cnc(Cl)c(Br)c1]

The title compound was prepared in an analogous fashion to that described in Stage 11.2 using 5-bromo-6-chloro-nicotinic acid and 4-aminophenylsulfur pentafluoride to afford an orange solid. HPLC (Condition 4), $t_R$=6.43 min, UPLC-MS (Condition 3), $t_R$=1.27 min, m/z=435.3/437.2 [M+H]$^+$.

Example 18

(R)—N-(4-((Chlorodifluoromethyl)thio)phenyl)-6-(3-hydroxypyrrolidin-1-yl)-5-(1H-pyrazol-5-yl)nicotinamide

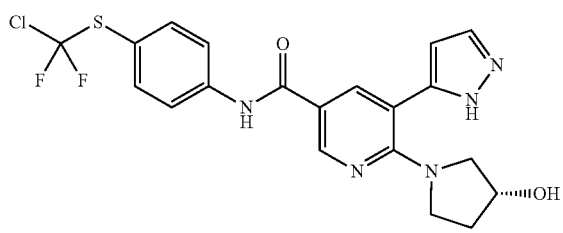 [SMILES: O=C(Nc1ccc(SC(F)(F)Cl)cc1)c1cnc(N2CC[C@@H](O)C2)c(-c2ccn[nH]2)c1]

The title compound was prepared in an analogous fashion to that described in Example 8 using (R)-5-bromo-N-(4-((chlorodifluoromethyl)thio)phenyl)-6-(3-hydroxypyrrolidin-1-yl)nicotinamide (Stage 18.1) and 1-(tetrahydro-2H-pyran-2-yl)-5-(4,4,5,5-tetramethyl-1,3,2-dioxaborolan-2-yl)-1H-pyrazole to afford an off-white solid. HPLC (Condition 4) $t_R$=4.94 min, UPLC-MS (Condition 3) $t_R$=0.99 min, m/z=466.3 [M+H]$^+$; $^1$H-NMR (400 MHz, DMSO-d$_6$) δ ppm 1.65-1.88 (m, 2H) 2.86-2.99 (m, 1H) 3.19-3.33 (m, 2H) 3.36-3.51 (m, 1H) 4.13-4.23 (m, 1H) 4.76-4.90 (m, 1H) 6.31-6.42 (m, 1H) 7.65 (d, J=8.21 Hz, 2H) 7.76-7.84 (m, 1H) 7.92 (d, J=8.60 Hz, 2H) 7.98-8.08 (m, 1H) 8.66-8.82 (m, 1H) 10.28 (s, 1H) 12.82-13.14 (m, 1H).

Stage 18.1: (R)-5-Bromo-N-(4-((chlorodifluoromethyl)thio)phenyl)-6-(3-hydroxypyrrolidin-1-yl)nicotinamide

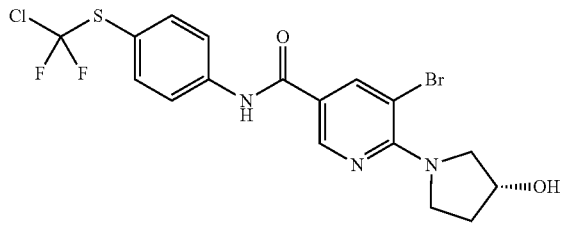 [SMILES: O=C(Nc1ccc(SC(F)(F)Cl)cc1)c1cnc(N2CC[C@@H](O)C2)c(Br)c1]

The title compound was prepared in an analogous fashion to that described in Stage 9.2 using 5-bromo-6-chloro-N-(4-((chlorodifluoromethyl)thio)phenyl)nicotinamide (Stage 18.2) and (R)-pyrrolidin-3-ol to afford an off-white crystalline solid. HPLC (Condition 4) $t_R$=5.97 min, UPLC-MS (Condition 3) $t_R$=1.19 min, m/z=478.2/480.1 [M+H]$^+$.

Stage 18.2: 5-Bromo-6-chloro-N-(4-((chlorodifluoromethyl)thio)phenyl)nicotinamide

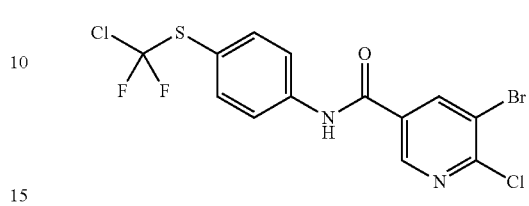

The title compound was prepared in an analogous fashion to that described in Stage 11.2 using 5-bromo-6-chloro-nicotinic acid and 4-((chloro-difluoromethyl)thio)aniline (Stage 18.3) to afford an off-white crystalline solid. HPLC (Condition 4) $t_R$=6.78 min, UPLC-MS (Condition 3) $t_R$=1.32 min, m/z=425 [M−H]$^-$.

Stage 18.3: 4-((Chlorodifluoromethyl)thio)aniline

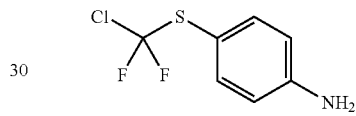

To a solution of 4-nitrophenylchlorodifluoromethyl sulfide (prepared as described in DE2845997, 627, 67.5 g, 0.28 mol) in ethanol (270 mL) and water (68 mL) stirred at 72° C. was added concentrated HCl (3.4 mL, 41.5 mmol) and iron powder (203 g, 3.63 mol) in three portions over 10 min. The RM was stirred at 82° C. for 30 min, filtered through Celite0 (EtOH), the solvent was evaporated off under reduced pressure to give a yellow oil which was dissolved in DCM and washed with sat. NaHCO$_3$ and brine. The organic phase was dried over MgSO4, filtered and the filtrate was evaporated off under reduced pressure to give the crude product as a yellow oil which was distilled (b.p. 88-92° C., 0.9 mmHg) and filtered through Celite® to afford the title compound as a pale yellow oil. $^1$H-NMR (300 MHz, CDCl$_3$) δ ppm 3.98 (br. s, 2H) 6.67 (dd, 2H) 7.43 (dd, 2H).

Example 19

(R)-6-(3-Hydroxypyrrolidin-1-yl)-N-(4-(perfluoroethoxy)phenyl)-5-(1H-pyrazol-5-yl)nicotinamide

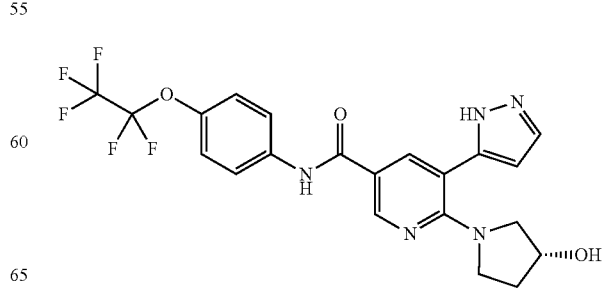

The title compound was prepared in an analogous fashion to that described in Example 8 using (R)-5-bromo-6-(3-hydroxypyrrolidin-1-yl)-N-(4-(perfluoroethoxy)phenyl)nicotinamide (Stage 19.1) and 1-(tetrahydro-2H-pyran-2-yl)-5-(4,4,5,5-tetramethyl-1,3,2-dioxaborolan-2-yl)-1H-pyrazole to afford an off-white solid. HPLC (Condition 4) $t_R$=4.86 min, UPLC-MS (Condition 3) $t_R$=0.97 min, m/z=484.4 [M+H]$^+$; $^1$H-NMR (400 MHz, DMSO-d$_6$) δ ppm 1.62-1.92 (m, 2H) 2.94 (d, J=1.00 Hz, 1H) 3.18-3.34 (m, 2H) 3.37-3.51 (m, 1H) 4.13-4.22 (m, 1H) 4.70-4.91 (m, 1H) 6.37 (br. s, 1H) 7.31 (d, J=8.99 Hz, 2H) 7.86 (m, J=9.00 Hz, 3H) 8.01 (br. s, 1H) 8.65-8.83 (m, 1H) 10.17 (s, 1H) 12.84-13.11 (m, 1H).

Stage 19.1: (R)-5-Bromo-6-(3-hydroxypyrrolidin-1-yl)-N-(4-(perfluoroethoxy)phenyl)nicotinamide

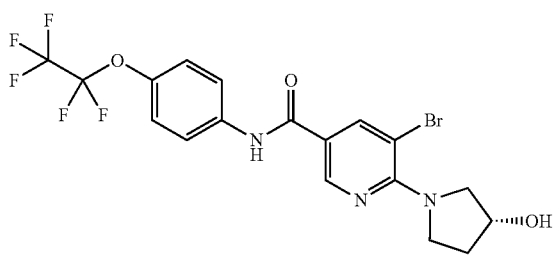 [SMILES: O=C(Nc1ccc(OC(F)(F)C(F)(F)F)cc1)c1cnc(N2CC[C@@H](O)C2)c(Br)c1]

The title compound was prepared in an analogous fashion to that described in Stage 9.2 using 5-bromo-6-chloro-N-(4-(perfluoroethoxy)phenyl)nicotinamide (Stage 19.2) and (R)-pyrrolidin-3-ol to afford an off-white crystalline solid. HPLC (Condition 4) $t_R$=6.01 min, UPLC-MS (Condition 3) $t_R$=1.17 min, m/z=496.2 [M+H]$^+$.

Stage 19.2: 5-Bromo-6-chloro-N-(4-(perfluoroethoxy)phenyl)nicotinamide

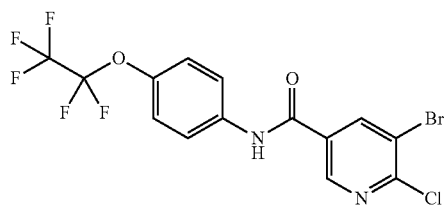 [SMILES: O=C(Nc1ccc(OC(F)(F)C(F)(F)F)cc1)c1cnc(Cl)c(Br)c1]

The title compound was prepared in an analogous fashion to that described in Stage 9.3 using 5-bromo-6-chloro-nicotinic acid and 4-(perfluoroethoxy)aniline to afford an off-white crystalline solid. HPLC (Condition 4) $t_R$=6.73 min, UPLC-MS (Condition 3) $t_R$=1.30 min, m/z=443.1 [M–H]$^-$.

Example 20

(R)—N-(4-(Chlorodifluoromethoxy)phenyl)-4-(3-hydroxypyrrolidin-1-yl)-3-(1H-pyrazol-5-yl)benzamide

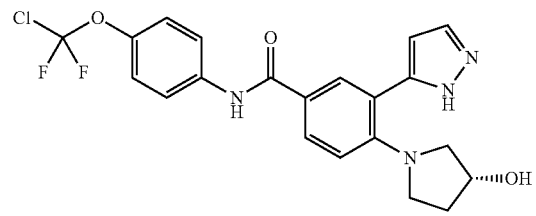 [SMILES: O=C(Nc1ccc(OC(F)(F)Cl)cc1)c1ccc(N2CC[C@@H](O)C2)c(-c2ccn[nH]2)c1]

The title compound was prepared in an analogous fashion to that described in Example 8 using (R)-3-bromo-N-(4-(chlorodifluoromethoxy)phenyl)-4-(3-hydroxypyrrolidin-1-yl)benzamide (Stage 20.1) and 1-(Tetrahydro-2H-pyran-2-yl)-1H-pyrazole-5-boronic acid pinacol ester to afford an off-white solid. UPLC-MS (Condition 3) $t_R$=0.99 min, m/z=449.0 [M+H]$^+$, m/z=493.0 [M+formic acid-H]$^-$; $^1$H NMR (400 MHz, DMSO-d$_6$) δ ppm 1.67-1.79 (m, 1H) 1.80-1.92 (m, 1H) 2.72 (d, J=10.88 Hz, 1H) 3.03-3.18 (m, 2H) 3.19-3.30 (m, 1H) 4.19 (br. s, 1H) 4.77-4.92 (m, 1H) 6.22-6.42 (m, 1H) 6.76-6.93 (m, 1H) 7.31 (d, J=8.56 Hz, 2H) 7.45-7.81 (m, 1H) 7.83-7.95 (m, 4H) 10.12 (s, 1H) 12.71-13.12 (m, 1H).

Stage 20.1: (R)-3-Bromo-N-(4-(chlorodifluoromethoxy)phenyl)-4-(3-hydroxypyrrolidin-1-yl)benzamide

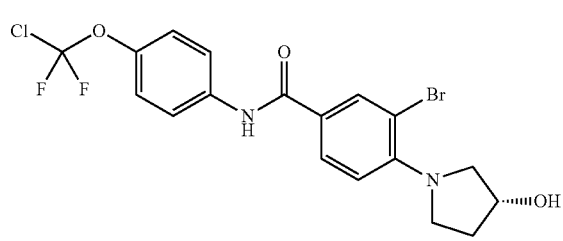 [SMILES: O=C(Nc1ccc(OC(F)(F)Cl)cc1)c1ccc(N2CC[C@@H](O)C2)c(Br)c1]

A mixture of 3-bromo-N-(4-(chlorodifluoromethoxy)phenyl)-4-fluorobenzamide (1 g, 2.53 mmol), (R)-pyrrolidin-3-ol (0.331 g, 3.80 mmol), TEA (0.706 mL, 5.07 mmol) and DMSO (2.53 mL) was stirred at 90° C. for 20 h. The RM was treated with 0.5 M HCl (50 mL) and extracted with EtOAc. The combined extracts were washed with 0.5 M HCl, sat. aq. NaHCO$_3$ and brine, dried over Na$_2$SO$_4$ and the solvent was evaporated off under reduced pressure to give the crude product which was purified by flash chromatography (RediSep® Silica gel column, 40 g, cyclohexane/EtOAc, from 1% to 4.5% EtOAc). The fractions containing the pure product were combined and the solvent was evaporated off under reduced pressure to give a residue which was triturated under cyclohexane to yield the title product as a white amorphous solid. UPLC-MS (Condition 3) $t_R$=1.15 min, m/z=462.9 [M+H]$^+$, m/z=460.9 [M–H]$^-$; $^1$H NMR (400 MHz, DMSO-d$_6$) δ ppm 1.81-1.90 (m, 1H) 1.92-2.03 (m, 1H) 3.27 (dd, J=10.39, 1.10

Hz, 1H) 3.36-3.44 (m, 1H) 3.62-3.71 (m, 1H) 3.81 (dd, J=10.45, 4.71 Hz, 1H) 4.32-4.40 (m, 1H) 4.99 (d, J=3.42 Hz, 1H) 6.93 (d, J=8.80 Hz, 1H) 7.33 (d, J=9.05 Hz, 2H) 7.82-7.91 (m, 3H) 8.14 (d, J=2.20 Hz, 1H) 10.21 (s, 1H).

Stage 20.2: 3-Bromo-N-(4-(chlorodifluoromethoxy)phenyl)-4-fluorobenzamide

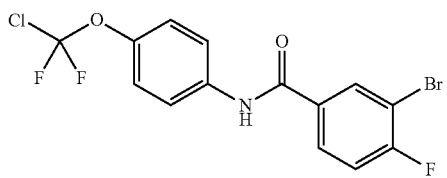 [SMILES: O=C(Nc1ccc(OC(F)(F)Cl)cc1)c1ccc(F)c(Br)c1]

The title compound was prepared in an analogous fashion to that described in Stage 1.3 using 3-bromo-4-fluorobenzoic acid and 4-(chlorodifluoromethoxy)aniline to afford an off-white solid. UPLC-MS (Condition 3) $t_R$=1.25 min, m/z=394.0 [M+H]$^+$, m/z=391.9 [M–H]$^-$; 1H NMR (400 MHz, DMSO-d$_6$) δ ppm 7.37 (d, J=9.17 Hz, 2H) 7.57 (t, J=8.68 Hz, 1H) 7.84-7.91 (m, 2H) 8.03 (ddd, J=8.62, 4.83, 2.32 Hz, 1H) 8.32 (dd, J=6.60, 2.20 Hz, 1H) 10.52 (s, 1H).

Example 21

(S)-6-(3-(Aminomethyl)pyrrolidin-1-yl)-N-(4-(chlorodifluoromethoxy)phenyl)-5-(1H-pyrazol-5-yl)nicotinamide

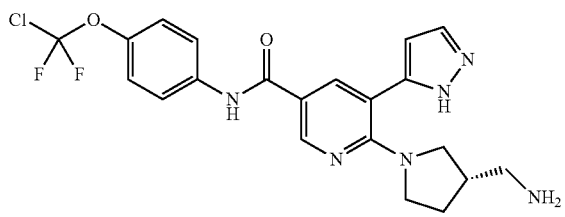 [SMILES: NC[C@@H]1CCN(c2ncc(C(=O)Nc3ccc(OC(F)(F)Cl)cc3)cc2-c2ccn[nH]2)C1]

The title compound was prepared in an analogous fashion to that described in Example 8 using (S)-tert-butyl((1-(3-bromo-5-(4-(chlorodifluoromethoxy)phenyl)carbamoyl)-pyridin-2-yl)pyrrolidin-3-yl)methyl)carbamate (Stage 21.1) and 1-(tetrahydro-2H-pyran-2-yl)-5-(4,4,5,5-tetramethyl-1,3,2-dioxaborolan-2-yl)-1H-pyrazole to afford an off-white powder. HPLC (Condition 4) $t_R$=4.15 min, UPLC-MS (Condition 3) $t_R$=0.78 min, m/z=463.1 [M+H]$^+$; $^1$H-NMR (400 MHz, DMSO-d$_6$) δ ppm 1.50-1.62 (m, 1H) 1.91 (d, J=6.26 Hz, 1H) 2.27 (s, 1H) 2.72 (d, J=7.04 Hz, 2H) 3.04-3.16 (m, 3H) 3.30 (br. s, 2H) 3.47 (dd, J=11.34, 7.04 Hz, 1H) 6.38 (d, J=1.96 Hz, 2H) 7.31 (d, J=8.60 Hz, 2H) 7.64-7.91 (m, 2H) 8.05 (d, J=2.35 Hz, 1H) 8.72 (d, J=1.95 Hz, 1H) 10.19 (s, 1H) 12.86-13.01 (m, 1H).

Stage 21.1: (S)-tert-Butyl((1-(3-bromo-5-(4-(chlorodifluoromethoxy)phenyl)-carbamoyl)pyridin-2-yl)pyrrolidin-3-yl)methyl)carbamate

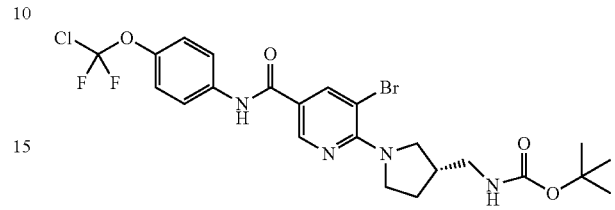

The title compound was prepared in an analogous fashion to that described in Stage 8.1 using 5-bromo-6-chloro-N-(4-(chlorodifluoromethoxy)phenyl)nicotinamide (Stage 9.3) and (R)-1-pyrrolidin-3-ylmethyl-carbamic acid tert-butyl ester to afford a crystalline solid. HPLC (Condition 4) $t_R$=6.09 min, UPLC-MS (Condition 3) $t_R$=1.36 min, m/z=577.2 [M+H]$^+$.

Example 22

(R)—N-(4-(Chlorodifluoromethoxy)phenyl)-4-(3-hydroxypyrrolidin-1-yl)-3-(3-methyl-1H-pyrazol-5-yl)benzamide

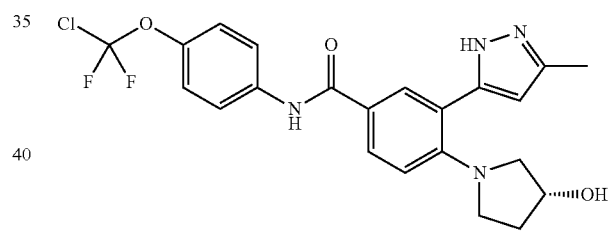

3-Methyl-1-(tetrahydro-2H-pyran-2-yl)-5-(4,4,5,5-tetramethyl-1,3,2-dioxaborolan-2-yl)-1H-pyrazole (Stage 23.1, 128 mg, 0.329 mmol), K$_3$PO$_4$ (140 mg, 0.658 mmol) and Pd(PPh$_3$)$_4$ (15.22 mg, 0.013 mmol) were added to a solution of (R)-3-bromo-N-(4-(chlorodifluoromethoxy)phenyl)-4-(3-hydroxypyrrolidin-1-yl)benzamide (Stage 20.1, 80 mg, 0.165 mmol) in toluene (1.5 mL) under an argon atmosphere. and the RM was heated at 110° C. for 2 h. The solvent was evaporated off under reduced pressure and the residue was dissolved in DCM (4 mL) and treated with TFA (0.507 mL, 6.58 mmol) and stirred at RT for 2 h. The RM was treated with sat. aq. Na$_2$CO$_3$ (20 mL) and extracted with EtOAc. The combined extracts were washed with brine (20 mL), dried over Na$_2$SO$_4$, and the solvent was evaporated off under reduced pressure to give a crude product which was purified by preparative HPLC (Condition 10-20% to 80% B in 20 min). Fractions containing pure product were combined, treated with sat. aq. Na$_2$CO$_3$ and the MeCN was evaporated off under reduced pressure. The aq. residue was extracted with DCM and the combined extracts were dried over Na$_2$SO$_4$, filtered and the filtrate was evaporated off under reduced pressure to give a residue which was crystallized from DCM/n-hexane to give the title product as a white solid.

HPLC (Condition 5) t$_R$=6.41 min, UPLC-MS (Condition 3) t$_R$=1.03 min, m/z=463 [M+H]$^+$; $^1$H-NMR (400 MHz, DMSO-d$_6$) δ ppm 1.67-1.78 (m, 1H) 1.84 (s, 1H) 2.16-2.30 (m, 3H) 2.74 (d, J=10.56 Hz, 1H) 3.04-3.33 (m, 3H) 4.14-4.23 (m, 1H) 4.76-4.87 (m, 1H) 6.07 (s, 1H) 6.73-6.86 (m, 1H) 7.29 (d, J=8.21 Hz, 2H) 7.78-7.90 (m, J=8.99 Hz, 4H) 10.07 (s, 1H) 12.34-12.56 (m, 1H).

Example 23

(R)—N-(4-(Chlorodifluoromethoxy)phenyl)-6-(3-hydroxypyrrolidin-1-yl)-5-(3-methyl-1H-pyrazol-5-yl)nicotinamide

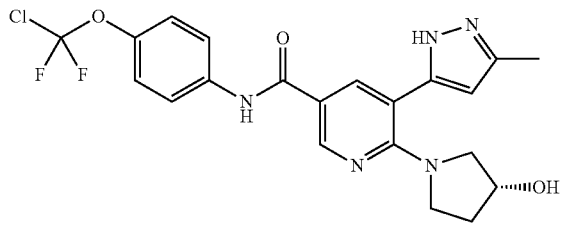 [SMILES: Cc1cc(-c2cc(C(=O)Nc3ccc(OC(F)(F)Cl)cc3)cnc2N2CC[C@@H](O)C2)[nH]n1]

3-Methyl-1-(tetrahydro-2H-pyran-2-yl)-5-(4,4,5,5-tetramethyl-1,3,2-dioxaborolan-2-yl)-1H-pyrazole (Stage 23.1, 150 mg, 0.359 mmol), K$_3$PO$_4$ (147 mg, 0.692 mmol) and Pd(PPh$_3$)$_4$ (15.98 mg, 0.014 mmol) were added to a solution of (R)-5-Bromo-N-(4-(chlorodifluoromethoxy)phenyl)-6-(3-hydroxypyrrolidin-1-yl)nicotinamide (Stage 9.2, 80 mg, 0.173 mmol) in toluene (1.5 mL) under an argon atmosphere and the RM was stirred at 110° C. for 2 h. The solvent was evaporated off under reduced pressure and the residue was dissolved in DCM (1.5 mL), treated with TFA (0.533 mL, 6.92 mmol) and stirred at RT for 2 h. The RM was treated with sat. aq. Na$_2$CO$_3$ (20 mL) and extracted with EtOAc. The combined extracts were washed with brine (20 mL), dried over Na$_2$SO$_4$, and the solvent was evaporated off under reduced pressure to give a crude product which was purified by flash chromatography (Silica gel column, 12 g, DCM/MeOH from 99:1 to 92:8) and crystallized from DCM/n-hexane to give the title product as a white solid. HPLC (Condition 5) t$_R$=5.92 min, UPLC-MS (Condition 3) t$_R$=0.94 min, m/z=464.1 [M+H]$^+$; $^1$H-NMR (400 MHz, DMSO-d$_6$) δ ppm 1.67-1.89 (m, 2H) 2.19-2.31 (m, 3H) 2.98 (d, J=10.95 Hz, 1H) 3.24-3.35 (m, 2H) 3.39-3.52 (m, 2H) 4.16-4.25 (m, 1H) 4.80-4.90 (m, 1H) 6.11-6.17 (m, 1H) 7.32 (d, J=8.60 Hz, 2H) 7.87 (d, J=8.99 Hz, 2H) 7.97-8.06 (m, 1H) 8.66-8.78 (m, 1H) 10.16 (s, 1H) 12.51-12.70 (m, 1H).

Stage 23.1: 3-Methyl-1-(tetrahydro-2H-pyran-2-yl)-5-(4,4,5,5-tetramethyl-1,3,2-dioxaborolan-2-yl)-1H-pyrazole

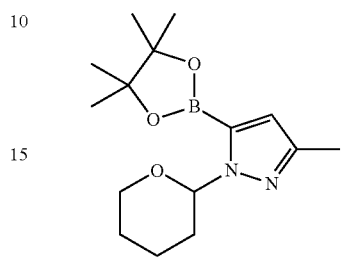

A mixture of 3-methylpyrazole (3.0 g, 35.4 mmol), 3,4-dihydro-2H-pyrane (4.97 mL, 53.2 mmol) and TFA (0.02 mL, 0.260 mmol) was stirred at 85° C. for 6 h under an argon atmosphere. The RM was cooled to RT and NaH 60% in mineral oil (0.061 g, 1.524 mmol) was and the RM was stirred for 10 min. The RM was purified by bulb-to-bulb distillation to give 3-methyl-1-(tetrahydro-2H-pyran-2-yl)-1H-pyrazole (b.p. 150-170° C./12 mbar). A solution of n-BuLi in n-hexane (3.38 mL of 1.6 M, 5.41 mmol) was added dropwise over 10 min to a solution of 3-methyl-1-(tetrahydro-2H-pyran-2-yl)-1H-pyrazole (1.0 g, 5.41 mmol) in THF (12 mL) at −70° C. under a nitrogen atmosphere and The RM was stirred for 10 min and then treated dropwise with 2-methoxy-4,4,5,5-tetramethyl-1,3,2-dioxaborolane (0.898 g, 5.69 mmol) and stirred at −70° C. for 1 h. The RM was allowed to warm to RT, treated with n-hexane and the product was filtered, dissolved in water (10 mL) and acidified to pH 6 with aqueous citric acid (10%). The water was evaporated off under reduced pressure and the aqueous residue extracted with EtOAc, dried over Na$_2$SO$_4$ and the solvent was evaporated off under reduced pressure to give the title product as a yellow resin. UPLC-MS (Condition 3) t$_R$=0.56 min, m/z=211.2 [M+H]$^+$.

Example 24

(R)—N-(4-(Chlorodifluoromethoxy)phenyl)-3-(4-fluoro-1H-pyrazol-5-yl)-4-(3-hydroxypyrrolidin-1-yl)benzamide

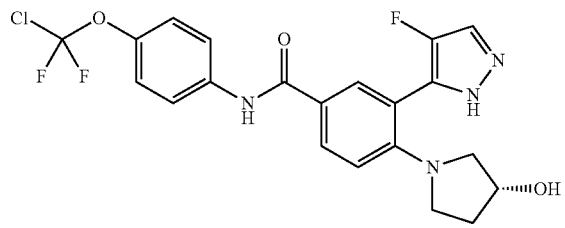 [SMILES: O=C(Nc1ccc(OC(F)(F)Cl)cc1)c1ccc(N2CC[C@@H](O)C2)c(-c2[nH]ncc2F)c1]

A mixture of N-(4-(chlorodifluoromethoxy)phenyl)-4-fluoro-3-(4-fluoro-1H-pyrazol-5-yl)benzamide (Stage 24.1, 62 mg, 0.147 mmol), R-3-hydroxypyrrolidine (0.031 mL, 0.206 mmol) and TEA (0.062 mL, 0.442 mmol) in DMSO (0.5 mL) was stirred at 100° C. for 16 h. The RM was diluted with EtOAc (30 mL), treated with sat. aq. Na$_2$CO$_3$ (20 mL)

and extracted with EtOAc. The combined extracts were washed with water (20 mL) and brine (20 mL), dried over Na$_2$SO$_4$ and the solvent was evaporated off under reduced pressure to give a crude product which was purified by preparative HPLC (Condition 10). Fractions containing pure product were combined, treated with sat. aq. Na$_2$CO$_3$ and the MeCN was removed under reduced pressure. The aq. residue was extracted with DCM and the combined extracts were dried over Na$_2$SO$_4$ and the solvent was evaporated off under reduced pressure. The residue was dissolved in DCM and treated with n-hexane to give the title product as a white solid. HPLC (Condition 5) t$_R$=6.61 min, UPLC-MS (Condition 3) t$_R$=1.01 min, m/z=467.3 [M+H]$^+$; $^1$H-NMR (400 MHz, DMSO-d$_6$) δ ppm 1.69-1.95 (m, 2H) 2.79 (d, J=10.56 Hz, 1H) 3.06-3.20 (m, 2H) 3.22-3.35 (m, 1H) 4.13-4.30 (m, 1H) 4.79-4.96 (m, 1H) 6.75-6.92 (m, 1H) 7.31 (d, J=8.60 Hz, 2H) 7.86 (m, J=9.38 Hz, 5H) 10.11 (s, 1H) 12.67-13.12 (m, 1H).

Stage 24.1: N-(4-(Chlorodifluoromethoxy)phenyl)-4-fluoro-3-(4-fluoro-1H-pyrazol-5-yl)benzamide

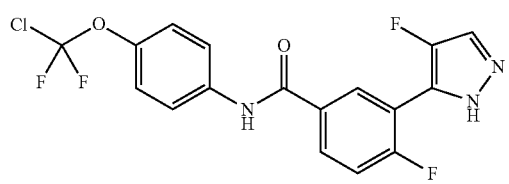 [SMILES: O=C(Nc1ccc(OC(F)(F)Cl)cc1)c1ccc(F)c(-c2[nH]ncc2F)c1]

A mixture of 3-bromo-N-(4-(chlorodifluoromethoxy)phenyl)-4-fluorobenzamide (Stage 20.2, 200 mg, 0.497 mmol), 4-fluoro-5-(tributylstannyl)-1H-pyrazole (211 mg, 0.472 mmol) and Pd(PPh$_3$)$_4$ (28.7 mg, 0.025 mmol) in DMSO (1.5 mL) in a sealed vial was stirred at 100° C. for 20 h under an argon atmosphere. The RM was diluted with EtOAc (30 mL), treated with sat. aq. Na$_2$CO$_3$ (20 mL) and extracted with EtOAc. The combined extracts were washed with water (20 mL) and brine (20 mL), dried over Na$_2$SO$_4$ and the solvent was evaporated off under reduced pressure to give a crude product which was purified by flash chromatography (Silica gel column, 12 g, n-hexane/EtOAc 95:5 to 6:4) to give the title product as a white solid. HPLC (Condition 5) t$_R$=7.20 min, UPLC-MS (Condition 3) t$_R$=1.12 min, m/z=400.1 [M+H]$^+$.

Example 25

(R)—N-(4-(Chlorodifluoromethoxy)phenyl)-5-(4-fluoro-1H-pyrazol-5-yl)-6-(3-hydroxypyrrolidin-1-yl)nicotinamide

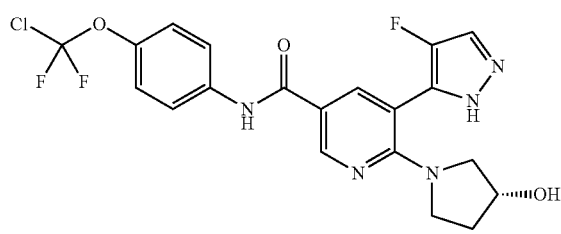 [SMILES: O=C(Nc1ccc(OC(F)(F)Cl)cc1)c1cnc(N2CC[C@@H](O)C2)c(-c2[nH]ncc2F)c1]

The title compound was prepared in an analogous fashion to that described in Example 5 using 6-chloro-N-(4-(chlorodifluoromethoxy)phenyl)-5-(4-fluoro-1H-pyrazol-5-yl) nicotinamide (Stage 25.1) and (R)-pyrrolidin-3-ol to afford a white powder. HPLC (Condition 4) t$_R$=4.89 min, HPLC Chiral (CHIRALCEL® OD-H, 250×4.6 mm, eluent:n-heptane/EtOH/MeOH (85:10:5), 1 mL/min, UV 210 nm) t$_R$=9.34 min, UPLC-MS (Condition 3) t$_R$=0.96 min, m/z=468.1 [M+H]$^+$; $^1$H-NMR (400 MHz, DMSO-d$_6$) δ ppm 1.67-1.92 (m, 2H) 3.00 (d, J=11.73 Hz, 1H) 3.19-3.33 (m, 2H) 3.43 (m, J=7.00 Hz, 1H) 4.22 (br. s, 1H) 4.87 (br. s, 1H) 7.31 (d, J=8.60 Hz, 2H) 7.85 (d, J=8.99 Hz, 2H) 7.90-8.10 (m, 2H) 8.77 (br. s, 1H) 10.18 (s, 1H) 12.83-13.19 (m, 1H).

Stage 25.1: 6-Chloro-N-(4-(chlorodifluoromethoxy)phenyl)-5-(4-fluoro-1H-pyrazol-5-yl)nicotinamide

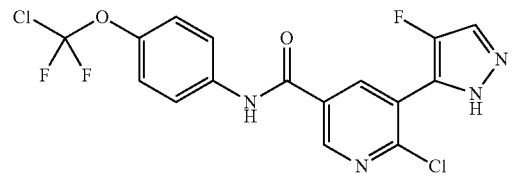 [SMILES: O=C(Nc1ccc(OC(F)(F)Cl)cc1)c1cnc(Cl)c(-c2[nH]ncc2F)c1]

The title compound was prepared in an analogous fashion to that described in Stage 13.1 using 6-chloro-N-(4-(chlorodifluoromethoxy)phenyl)-5-iodonicotinamide (Stage 25.2) and 4-fluoro-5-(tributylstannyl)-1H-pyrazole to afford an off-white powder. HPLC (Condition 4) t$_R$=5.69 min, UPLC-MS (Condition 3) t$_R$=1.09 min, m/z=415 [M−H]$^-$; $^1$H-NMR (400 MHz, DMSO-d$_6$) δ ppm.

Stage 25.2: 6-Chloro-N-(4-(chlorodifluoromethoxy)phenyl)-5-iodonicotinamide

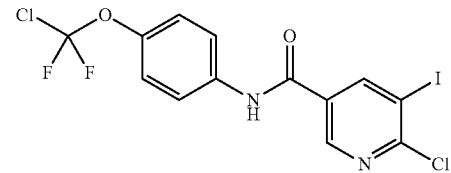 [SMILES: O=C(Nc1ccc(OC(F)(F)Cl)cc1)c1cnc(Cl)c(I)c1]

The title compound was prepared in an analogous fashion to that described in Stage 11.2 using 6-chloro-5-iodonicotinic acid and 4-(chlorodifluoromethoxy)aniline to afford an off-white powder. HPLC (Condition 4) $t_R$=6.47 min, UPLC-MS (Condition 3) $t_R$=1.26 min, m/z=456.8 [M−H]⁻.

Example 26

(R)—N-(4-(Chlorodifluoromethoxy)phenyl)-6-(3-hydroxypyrrolidin-1-yl)-5-(3-(trifluoromethyl)-1H-pyrazol-5-yl)nicotinamide

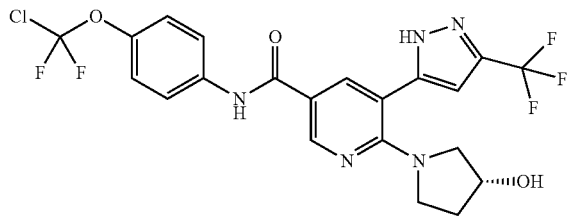 [SMILES: O=C(Nc1ccc(OC(F)(F)Cl)cc1)c1cnc(N2CC[C@@H](O)C2)c(-c2cc(C(F)(F)F)n[nH]2)c1]

K₃PO₄ (135 mg, 0.635 mmol), 1-(tetrahydro-2H-pyran-2-yl)-3-(trifluoromethyl)-1H-pyrazol-5-ylboronic acid (112 mg, 0.424 mmol) and Pd(PPh₃)₄ (12.24 mg, 10.59 mmol) were added to a solution of (R)-5-bromo-N-(4-(chlorodifluoromethoxy)phenyl)-6-(3-hydroxypyrrolidin-1-yl)nicotinamide (Stage 9.2, 100 mg, 0.212 mmol) in toluene (2 mL) and the RM was stirred at 110° C. for 2 h under an argon atmosphere. The RM was filtered through Hyflo®, washed with water and the solvent was evaporated off under reduced pressure to give the crude product which was purified by flash chromatography (Silica gel column, 12 g, DCM/EtOH from 99:1 to 94:6). The resulting intermediate was dissolved in DCM (2 mL), treated with TFA (0.462 mL, 5.99 mmol) and stirred for 1 h at RT. The RM was diluted with EtOAc (20 mL), treated with sat. aq. Na₂CO₃ (20 mL) and extracted with EtOAc. The combined extracts were washed with brine (20 mL), dried over Na₂SO₄ and the solvent was evaporated off under reduced pressure to give a crude product which was purified by flash chromatography (Silica gel column, 4 g, DCM/EtOH from 99:1 to 9:1). Fractions containing pure product were combined and the solvent was evaporated off under reduced pressure to give a residue which was triturated in DCM/n-hexane, filtered and dried to give the title product as a white solid. HPLC (Condition 5) $t_R$=6.545 min, UPLC-MS (Condition 3) $t_R$=1.10 min, m/z=518.1 [M+H]⁺; ¹H-NMR (400 MHz, DMSO-d₆) δ ppm 1.71-1.95 (m, 2H) 2.94 (d, J=11.34 Hz, 1H) 3.24 (m, 2H) 3.44 (m, 1H) 4.17-4.32 (m, 1H) 4.91 (br. s, 1H) 6.88 (s, 1H) 7.34 (d, J=8.21 Hz, 2H) 7.86 (d, J=9.38 Hz, 2H) 8.12 (s, 1H) 8.81 (s, 1H) 10.17 (s, 1H) 13.94 (s, 1H).

Example 27

(R)—N-(4-(Chlorodifluoromethoxy)phenyl)-6-(3-hydroxypyrrolidin-1-yl)-5-(1-methyl-1H-pyrazol-5-yl)nicotinamide

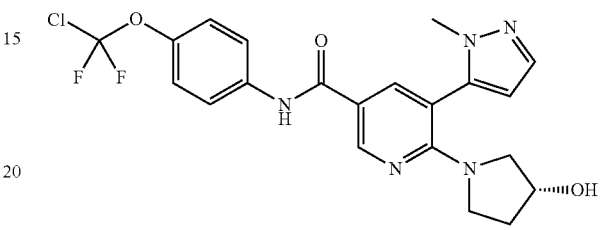

The title compound was prepared in an analogous fashion to that described in Stage 2.1 using (R)-5-bromo-N-(4-(chlorodifluoromethoxy)phenyl)-6-(3-hydroxypyrrolidin-1-yl)nicotinamide (Stage 9.2) and 1-methyl-5-(4,4,5,5-tetramethyl-1,3,2-dioxaborolan-2-yl)-1H-pyrazole to afford a white powder. HPLC (Condition 4) $t_R$=5.25 min, UPLC-MS (Condition 3) $t_R$0.98 min, m/z=464.1 [M+H]⁺; ¹H-NMR (400 MHz, DMSO-d₆) δ ppm 1.65-1.89 (m, 2H) 2.87-3.00 (m, 1H) 3.09-3.29 (m, 3H) 3.59 (s, 3H) 4.19 (br. s, 1H) 4.87 (d, J=3.13 Hz, 1H) 6.39 (s, 1H) 7.27-7.36 (m, 2H) 7.50 (dd, J=1.76, 0.98 Hz, 1H) 7.78-7.88 (m, 2H) 8.00 (d, J=2.35 Hz, 1H) 8.78 (dd, J=2.35, 1.17 Hz, 1H) 10.15 (s, 1H).

Example 28

(R)—N-(4-(Chlorodifluoromethoxy)phenyl)-6-(3-hydroxypyrrolidin-1-yl)-5-(1-methyl-1H-pyrazol-3-yl)nicotinamide

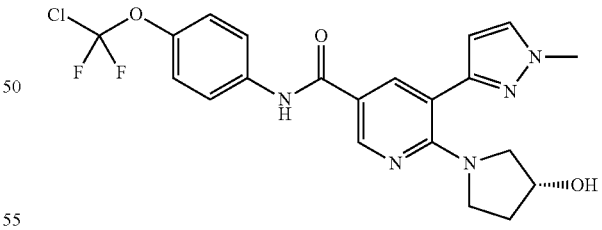

The title compound was prepared in an analogous fashion to that described in Stage 2.1 using (R)-5-bromo-N-(4-(chlorodifluoromethoxy)phenyl)-6-(3-hydroxypyrrolidin-1-yl)nicotinamide (Stage 9.2) and 1-methyl-3-(4,4,5,5-tetramethyl-1,3,2-dioxaborolan-2-yl)-1H-pyrazole to afford a white powder. HPLC (Condition 4) $t_R$=5.16 min, UPLC-MS (Condition 3) $t_R$0.98 min, m/z=464 [M+H]⁺; ¹H-NMR (400 MHz, DMSO-d₆) δ ppm 1.64-1.90 (m, 2H) 2.85-3.00 (m, 1H) 3.06-3.26 (m, 3H) 3.59 (s, 3H) 4.19 (br. s, 1H) 4.87 (d, J=2.74 Hz, 1H) 6.39 (s, 1H) 7.31 (d, J=8.60 Hz, 2H) 7.50 (dd, J=1.76, 0.98 Hz, 1H) 7.84 (d, J=8.60 Hz, 2H) 8.01 (d, J=2.74 Hz, 1H) 8.78 (dd, J=2.54, 0.98 Hz, 1H) 10.15 (s, 1H).

Example 29

(R)—N-(4-(Chlorodifluoromethoxy)phenyl)-5-(1-(2-hydroxyethyl)-1H-pyrazol-4-yl)-6-(3-hydroxypyrrolidin-1-yl)nicotinamide

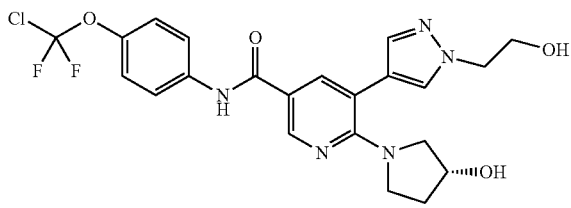 [SMILES: O=C(Nc1ccc(OC(F)(F)Cl)cc1)c1cnc(N2CC[C@@H](O)C2)c(-c2cnn(CCO)c2)c1]

2M Na$_2$CO$_3$ (0.375 mL, 0.75 mmol) was added to a solution of (R)-5-bromo-N-(4-(chlorodifluoromethoxy)phenyl)-6-(3-hydroxypyrrolidin-1-yl)nicotinamide (Stage 9.2, 116 mg, 0.25 mmol) and 1-(2-(tetrahydro-2H-pyran-2-yloxy)ethyl)-4-(4,4,5,5-tetramethyl-1,3,2-dioxaborolan-2-yl)-1H-pyrazole (161 mg, 0.5 mmol) in DME (1.0 mL). under an argon atmosphere. PdCl$_2$(dppf) (9.15 mg, 0.013 mmol) was then added and the RM mixture was stirred at 100° C. for 2 h. After cooling at RT, the RM was dissolved in EtOAc and washed with brine, dried over Na$_2$SO$_4$ and the solvent was evaporated off under reduced pressure. The crude product was dissolved in DCM (1.4 mL) cooled to 0° C., then treated with TFA (0.77 mL, 10 mmol) and stirred at RT for 3 h. The RM was poured into aq. Na$_2$CO$_3$ 10% (15 mL) and extracted with EtOAc. The combined extracts were dried over Na$_2$SO$_4$ and the solvent was evaporated off under reduced pressure to give the crude product which was purified by flash chromatography (RediSep® Silica gel column, DCM/MeOH, from 2% to 10% MeOH) to afford an off-white powder. HPLC (Condition 4) t$_R$=4.33 min, UPLC-MS (Condition 3) t$_R$=0.88 min, m/z=494 [M+H]$^+$; $^1$H-NMR (400 MHz, DMSO-d$_6$) δ ppm 1.67-1.88 (m, 2H) 2.96 (d, J=11.73 Hz, 0H) 3.24-3.37 (m, 2H) 3.41-3.53 (m, 1H) 3.75 (q, J=5.73 Hz, 2H) 4.04-4.25 (m, 4H) 4.81 (d, J=3.52 Hz, 1H) 4.86-4.94 (m, 1H) 7.31 (d, J=8.21 Hz, 2H) 7.53-7.59 (m, 1H) 7.79-7.89 (m, 3H) 7.93 (d, J=2.35 Hz, 1H) 8.65 (dd, J=2.35, 0.78 Hz, 1H) 10.15 (s, 1H).

Example 30

(R)—N-(4-(1,1-Difluoroethoxy)phenyl)-6-(3-hydroxypyrrolidin-1-yl)-5-(1H-pyrazol-5-yl)nicotinamide

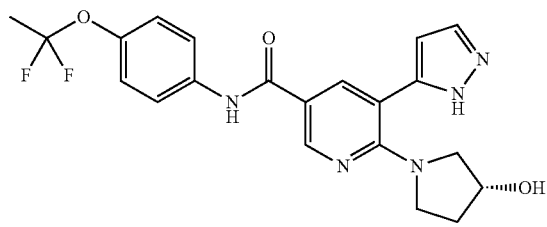 [SMILES: CC(F)(F)Oc1ccc(NC(=O)c2cnc(N3CC[C@@H](O)C3)c(-c3ccn[nH]3)c2)cc1]

K$_3$PO$_4$ (113 mg, 0.532 mmol), 1-(tetrahydro-2H-pyran-2-yl)-5-(4,4,5,5-tetramethyl-1,3,2-dioxaborolan-2-yl)-1H-pyrazole (99 mg, 0.355 mmol) and Pd(PPh$_3$)$_4$ (10.24 mg, 8.86 mmol) were added to a solution of (R)-5-bromo-N-(4-(1,1-difluoroethoxy)phenyl)-6-(3-hydroxypyrrolidin-1-yl)nicotinamide (Stage 30.1, 80 mg, 0.177 mmol) in toluene (1.5 mL) under argon atmosphere. and the RM was stirred at 110° C. for 1 h. The RM was diluted with EtOAc (20 mL) treated with sat. NaHCO$_3$ solution (20 mL). and extracted with EtOAc. The combined extracts were washed with brine (20 mL), dried with Na$_2$SO$_4$ and the solvent was evaporated off under reduced pressure to give a crude product which was purified by flash chromatography (Silica gel column, 12 g DCM/EtOH from 97:3 to 95:5) to afford N-(4-(1,1-difluoroethoxy)phenyl)-6-(R)-3-hydroxypyrrolidin-1-yl)-5-(1-(tetrahydro-2H-pyran-2-yl)-1H-pyrazol-5-yl)nicotinamide which (66 mg, 0.129 mmol) was dissolved in DCM (1.5 mL) and treated with TFA (0.546 mL, 7.09 mmol) and stirred for 2 h at RT. The RM was diluted with EtOAc (20 mL), treated with sat. NaHCO$_3$ solution (25 mL) and extracted with EtOAc (20 mL). The combined extracts were washed with brine (20 mL), dried over Na$_2$SO$_4$ and the solvent was evaporated off under reduced pressure to give the crude product which was purified by preparative HPLC (Condition 10). Fractions containing pure product were combined, treated with 0.5 g NaHCO$_3$ and the MeCN was evaporated off under reduced pressure. The aq. residue was extracted with DCM to give the title product as a white solid. HPLC (Condition 5) t$_R$=5.42 min, UPLC-MS (Condition 3) t$_R$=0.82 min, m/z=430.1 [M+H]$^+$; $^1$H-NMR (400 MHz, DMSO-d$_6$) δ ppm 1.68-1.87 (m, 2H) 1.93 (t, J=13.67 Hz, 3H) 2.94 (d, J=11.71 Hz, 1H) 3.15-3.33 (m, 2H) 3.38-3.48 (m, 1H) 4.19 (br. s, 1H) 6.37 (s, 1H) 7.15 (d, J=9.37 Hz, 2H) 7.65-7.83 (m, J=9.37 Hz, 3H) 8.03 (d, J=2.34 Hz, 1H) 8.73 (d, J=2.34 Hz, 1H).

Stage 30.1: (R)-5-Bromo-N-(4-(1,1-difluoroethoxy)phenyl)-6-(3-hydroxypyrrolidin-1-yl)nicotinamide

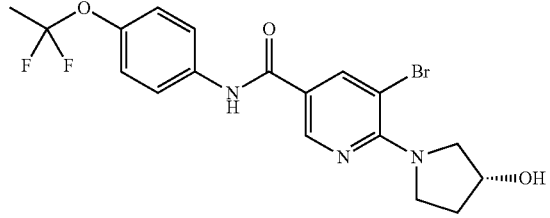 [SMILES: CC(F)(F)Oc1ccc(NC(=O)c2cnc(N3CC[C@@H](O)C3)c(Br)c2)cc1]

A mixture of 5-bromo-6-chloro-N-(4-(1,1-difluoroethoxy)phenyl)nicotinamide (Stage 30.2, 700 mg, 1.752 mmol), (R)-pyrrolidin-3-ol (0.170 mL, 2.102 mmol) and DIPEA (0.673 mL, 3.85 mmol) and iPrOH (2 mL) in a sealed vial was heated to 120° C. for 1 h. The RM was diluted with EtOAc (80 mL), treated with citric acid 10% (40 mL; ~pH4) and extracted with EtOAc. The combined extracts were washed with brine (2×40 mL), dried over Na$_2$SO$_4$ and the solvent was evaporated off under reduced pressure to give a residue which was washed with Et$_2$O and n-hexane and the crystals were dried to give the title product as a beige solid.

HPLC (Condition 5) $t_R$=6.4 min, UPLC-MS (Condition 3) $t_R$=1.02 min, m/z=442.1/444.0 [M+H]$^+$.

Stage 30.2: 5-Bromo-6-chloro-N-(4-(1,1-difluoroethoxy)phenyl)nicotinamide

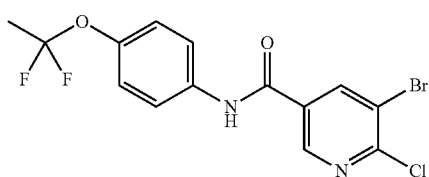 [SMILES: CC(F)(F)Oc1ccc(NC(=O)c2cnc(Cl)c(Br)c2)cc1]

Oxalyl chloride (653 µL, 7.46 mmol) was added to a mixture of 5-bromo-6-chloronicotinic acid (1.2 g, 4.97 mmol) and DMF (20 µL, 0.258 mmol) in DCM (40 mL) under nitrogen atmosphere and the RM was stirred for 2 h at RT. The solvent was evaporated, the residue was dissolved in DCM (10 mL) and evaporated again to dryness. The residue was dissolved in THF (30 mL), DIPEA (1.737 mL, 9.95 mmol) was added and the RM was cooled down to −15° C. 4-(1,1-difluoroethoxy)aniline (Stage 30.3, 0.932 g, 5.22 mmol) in THF (10 mL) was added dropwise in 15 min. period and the RM was stirred for 1 h at RT. The solvent was evaporated off under reduced pressure and the residue was diluted with EtOAc (100 mL), treated with citric acid 10% (60 mL) and extracted with EtOAc. The combined extracts were washed with sat. aq. Na$_2$CO$_3$ (50 mL) and brine (2×50 mL), dried over Na$_2$SO$_4$ and the solvent was evaporated off under reduced pressure to give the crude product which was suspended in n-hexane, filtered and dried to give the title product as a beige solid. HPLC (Condition 5) $t_R$=7.3 min, UPLC-MS (Condition 3) $t_R$=1.16 min, m/z=391/393 [M+H]$^+$.

Stage 30.3: 4-(1,1-Difluoroethoxy)aniline

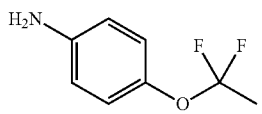

A solution of 1-(1,1-difluoroethoxy)-4-nitrobenzene (Stage 30.4, 2.95 g, 13.94 mmol) in EtOH (100 mL) was hydrogenated (Raney Ni 1.0 g; 26.5 h at RT). The RM was filtered through Hyflo® and the solvent was evaporated off under reduced pressure to give the crude title product as a brown oil. HPLC (Condition 5) $t_R$=4.5 min, UPLC-MS (Condition 3) $t_R$=0.74 min, m/z=174.1 [M+H]$^+$.

Stage 30.4: 1-(1,1-Difluoroethoxy)-4-nitrobenzene

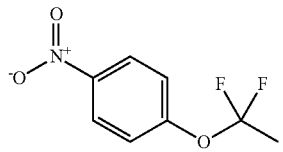

4-Nitroacetophenone (2.45 g, 14.54 mmol) and HF-pyridine (10.11 mL, 116 mmol) was added to a mixture of XeF2 (4.92 g, 29.1 mmol) and DCM (50 mL) in a plastic vial and the RM was stirred at RT for 20 h. The RM was added carefully to a stirred mixture of EtOAc (150 mL) and sat. NaHCO$_3$ (250 mL) and extracted with EtOAc. The combined extracts were washed with brine (2×100 mL), dried over Na$_2$SO$_4$ and the solvent was evaporated off under reduced pressure to give a crude product which was purified by flash chromatography (Silica gel column, 40 g, n-hexane/EtOAc (95:5)) to give the title product as a yellow oil. HPLC (Condition 5) $t_R$=6.9 min, UPLC-MS (Condition 3) $t_R$=1.05 min.

Example 31

(R)—N-(4-(2-Chloro-1,1,2,2-tetrafluoroethyl)phenyl)-6-(3-hydroxypyrrolidin-1-yl)-5-(1H-pyrazol-5-yl)nicotinamide

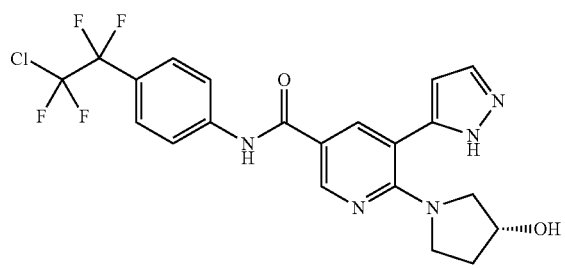 [SMILES: O=C(Nc1ccc(C(F)(F)C(F)(F)Cl)cc1)c1cnc(N2CC[C@@H](O)C2)c(-c2ccn[nH]2)c1]

The title compound was prepared in an analogous fashion to that described in Example 8 using (R)-5-bromo-N-(4-(2-chloro-1,1,2,2-tetrafluoroethyl)phenyl)-6-(3-hydroxypyrrolidin-1-yl)nicotinamide (Stage 31.1) and 1-(tetrahydro-2H-pyran-2-yl)-5-(4,4,5,5-tetramethyl-1,3,2-dioxaborolan-2-yl)-1H-pyrazole to afford a white powder. HPLC (Condition 4) $t_R$=4.89 min, UPLC-MS (Condition 3) $t_R$=0.98 min, m/z=484.1 [M+H]$^+$; $^1$H-NMR (400 MHz, DMSO-d$_6$) δ ppm 1.65-1.89 (m, 2H) 2.83-2.98 (m, 1H) 3.18-3.33 (m, 2H) 3.36-3.49 (m, 1H) 4.13-4.24 (m, 1H) 4.77-4.93 (m, 1H) 6.31-6.43 (m, 1H) 7.62 (d, J=8.59 Hz, 2H) 7.77-7.84 (m, 1H) 7.91-8.09 (m, 3H) 8.64-8.81 (m, 1H) 10.31 (s, 1H) 12.83-12.96 (m, 1H).

Stage 31.1: (R)-5-Bromo-N-(4-(2-chloro-1,1,2,2-tetrafluoroethyl)phenyl)-6-(3-hydroxypyrrolidin-1-yl)nicotinamide

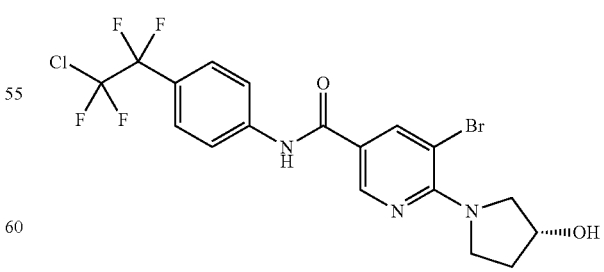

The title compound was prepared in an analogous fashion to that described in Stage 8.1 using 5-bromo-6-chloro-N-(4-(2-chloro-1,1,2,2-tetrafluoroethyl)phenyl)nicotinamide (Stage 31.2) and (R)-pyrrolidin-3-ol to afford a white powder.

HPLC (Condition 4) $t_R$=6.05 min, UPLC-MS (Condition 3) $t_R$=1.18 min, m/z=498 [M+H]+.

Stage 31.2: 5-Bromo-6-chloro-N-(4-(2-chloro-1,1,2,2-tetrafluoroethyl)phenyl)nicotinamide

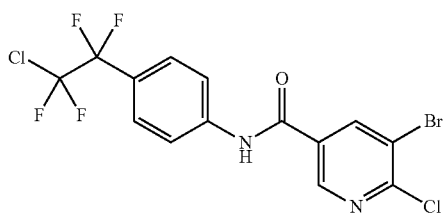 [SMILES: O=C(Nc1ccc(C(F)(F)C(F)(F)Cl)cc1)c1cnc(Cl)c(Br)c1]

The title compound was prepared in an analogous fashion to that described in Stage 9.3 using 5-bromo-6-chloronicotinic acid and 4-(2-chloro-1,1,2,2-tetrafluoroethyl)aniline (Stage 31.3) to afford a beige crystalline powder. HPLC (Condition 4) $t_R$=6.77 min, UPLC-MS (Condition 3) $t_R$=1.31 min, m/z=444.8 [M+H]+.

Stage 31.3:
4-(2-Chloro-1,1,2,2-tetrafluoroethyl)aniline

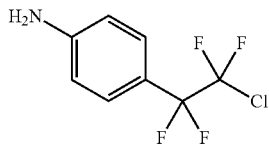 [SMILES: Nc1ccc(C(F)(F)C(F)(F)Cl)cc1]

Ni(PPh$_3$)$_4$ (222 mg, 0.2 mmol) was added to a mixture of aniline (745 mg, 8 mmol) and 1-chloro-1,1,2,2-tetrafluoro-2-iodoethane (1049 mg, 4 mmol) in DMF (10 mL) in a MW vial under an argon atmosphere. The vial was sealed and the RM was stirred for two days at 80° C. After cooling at RT, the RM was dissolved in Et$_2$O, washed with NaHCO$_3$ 10% and brine, dried over MgSO$_4$ and the solvent was evaporated off under reduce pressure to give a residue which was purified by flash chromatography (RediSep® Silica gel column, n-heptane/EtOAc, from 0 to 25% EtOAc) and further by reverse phase chromatography (MPLC, Lichroprep® 15-25 µm column, eluents: water+0.1% formic/MeCN+0.1% formic acid, gradient 10 to 50% MeCN+0.1% formic acid). The fractions containing pure product were combined and the MeCN was evaporated off under reduced pressure to give an aq. phase which was neutralized with NaHCO$_3$ and extracted with Et$_2$O. The combined extracts were dried over MgSO$_4$ and the solvent was evaporated off under reduced pressure to afford the title compound as a red oil. HPLC (Condition 4) $t_R$=5.48 min, UPLC-MS (Condition 3) $t_R$=1.04 min, m/z=269 [M+H]+.

Example 32

(R)-6-(3-Hydroxypyrrolidin-1-yl)-5-(1H-pyrazol-5-yl)-N-(6-((trifluoromethyl)thio)pyridin-3-yl)nicotinamide

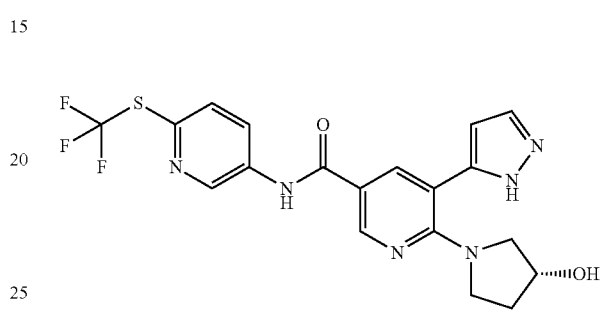

The title compound was prepared in an analogous fashion to that described in Example 8 using (R)-5-bromo-6-(3-hydroxypyrrolidin-1-yl)-N-(6-((trifluoromethyl)thio)pyridin-3-yl)nicotinamide (Stage 32.1) and 1-(tetrahydro-2H-pyran-2-yl)-5-(4,4,5,5-tetramethyl-1,3,2-dioxaborolan-2-yl)-1H-pyrazole to afford an off-white powder. HPLC (Condition 4) $t_R$=4.18 min, UPLC-MS (Condition 3) $t_R$=0.82 min, m/z=451.3 [M+H]+; $^1$H-NMR (400 MHz, DMSO-d$_6$) δ ppm 1.64-1.89 (m, 2H) 2.94 (d, J=11.73 Hz, 1H) 3.18-3.33 (m, 2H) 3.36-3.49 (m, 1H) 4.18 (br. s, 1H) 4.81 (d, J=3.13 Hz, 1H) 6.38 (s, 1H) 7.68-7.85 (m, 2H) 8.02 (d, J=1.95 Hz, 1H) 8.32 (dd, J=8.60, 2.35 Hz, 1H) 8.73 (d, J=2.35 Hz, 1H) 8.98 (d, J=2.35 Hz, 1H) 10.42 (s, 1H) 12.89-13.12 (m, 1H).

Stage 32.1: (R)-5-Bromo-6-(3-hydroxypyrrolidin-1-yl)-N-(6-((trifluoromethyl)thio)pyridin-3-yl)nicotinamide

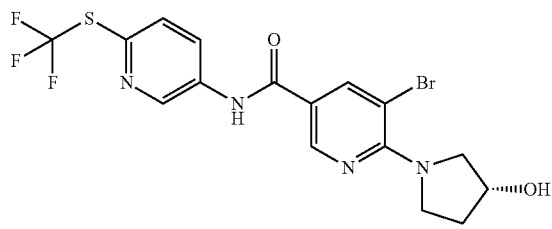

The title compound was prepared in an analogous fashion to that described in Stage 8.1 using 5-bromo-6-chloro-N-(6-((trifluoromethyl)thio)pyridin-3-yl)nicotinamide (Stage 32.2) and (R)-pyrrolidin-3-ol to afford an off-white powder.

HPLC (Condition 4) $t_R$=5.53 min, UPLC-MS (Condition 3) $t_R$=1.01 min, m/z=463.1 [M+H]$^+$.

Stage 32.2: 5-Bromo-6-chloro-N-(6-((trifluoromethyl)thio)pyridin-3-yl)nicotinamide

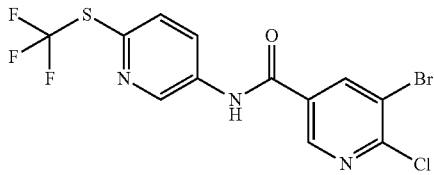 [SMILES: O=C(Nc1ccc(SC(F)(F)F)nc1)c1cnc(Cl)c(Br)c1]

The title compound was prepared in an analogous fashion to that described in Stage 9.3 using 5-bromo-6-chloronicotinic acid and 6-(trifluoromethylthio)pyridin-3-amine to afford an off-white powder. HPLC (Condition 4) $t_R$=6.43 min, UPLC-MS (Condition 3) $t_R$=1.15 min, m/z=411.9 [M−H]$^-$.

Example 33

(R)—N-(4-(Chlorodifluoromethoxy)phenyl)-6-(3-hydroxypyrrolidin-1-yl)-5-(4-methyl-1H-pyrazol-5-yl)nicotinamide

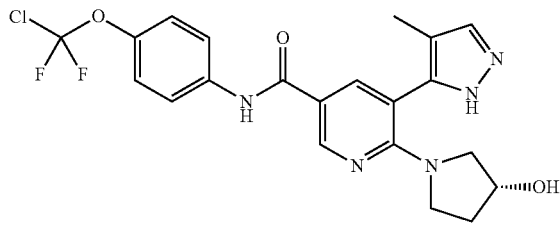 [SMILES: Cc1cn[nH]c1-c1cc(C(=O)Nc2ccc(OC(F)(F)Cl)cc2)cnc1N1CC[C@@H](O)C1]

DIPEA (77 μL, 0.44 mmol) was added to a solution of 6-chloro-N-(4-(chlorodifluoromethoxy)phenyl)-5-(4-methyl-1-(tetrahydro-2H-pyran-2-yl)-1H-pyrazol-5-yl)nicotinamide (Stage 33.1, 99 mg, 0.2 mmol) and (R)-pyrrolidin-3-ol, 20.9 mg, 0.24 mmol) in iPrOH (200 μL) in a vial, which was sealed and the RM mixture was stirred at 140° C. for 1.5 h. After cooling at RT, the RM was dissolved in EtOAc, washed with brine, dried over Na$_2$SO$_4$ and the solvent was evaporated off under reduced pressure. The residue was dissolved in DCM (1.1 mL), cooled to 0° C., treated with TFA (0.616 mL, 8 mmol) and stirred at RT for 3 h. The RM was poured in to 10% aq. Na$_2$CO$_3$ (10 mL) and extracted with EtOAc. The combined extracts were dried over Na$_2$SO$_4$ and the solvent was evaporated off under reduced pressure to give a residue which was purified by flash chromatography (RediSep® silica gel column, DCM/MeOH from 2% to 10% MeOH) to afford the title compound as a beige powder. HPLC (Condition 4) $t_R$=4.79 min, UPLC-MS (Condition 3) $t_R$=0.95 min, m/z=464 [M+H]$^+$; $^1$H-NMR (400 MHz, DMSO-d$_6$) δ ppm 1.63-1.92 (m, 5H) 2.81-2.96 (m, 1H) 3.05-3.41 (m, 3H) 4.17 (br. s, 1H) 4.81 (br. s, 1H) 7.30 (d, J=8.60 Hz, 2H) 7.58 (s, 1H) 7.79-8.02 (m, 3H) 8.73 (s, 1H) 10.15 (s, 1H) 12.58-12.85 (m, 1H).

Stage 33.1: 6-Chloro-N-(4-(chlorodifluoromethoxy)phenyl)-5-(4-methyl-1-(tetrahydro-2H-pyran-2-yl)-1H-pyrazol-5-yl)nicotinamide

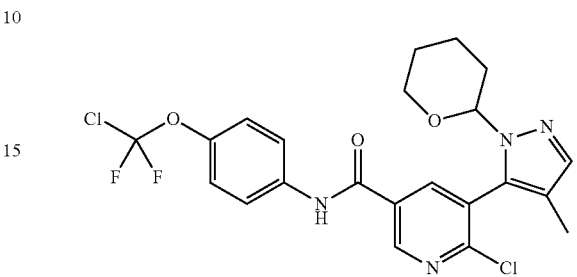

K$_3$PO$_4$ (191 mg, 0.9 mmol) and Pd(PPh$_3$)$_4$ (17.33 mg, 0.015 mmol) were added to a solution of 6-Chloro-N-(4-(chlorodifluoromethoxy)phenyl)-5-iodonicotinamide (Stage 25.2, 138 mg, 0.3 mmol) and 4-methyl-1-(tetrahydro-2H-pyran-2-yl)-5-(4,4,5,5-tetramethyl-1,3,2-dioxaborolan-2-yl)-1H-pyrazole (131 mg, 0.45 mmol) in toluene (1.5 mL) under an argon atmosphere in a vial, which was sealed and heated at 110° C. for 18 h. The RM was poured into 20 mL water and extracted with EtOAc. The combined extracts were dried over Na$_2$SO$_4$ and the solvent was evaporated off under reduced pressure to give a residue which was purified by flash chromatography (RediSep® Silica gel column, n-heptane/EtOAc, from 5 to 50% EtOAc) and crystallized from n-heptane to afford the title compound as an off-white powder. HPLC (Condition 4) $t_R$=6.8 min, UPLC-MS (Condition 3) $t_R$=1.26 min, m/z=495 [M−H]$^-$.

Example 34

(S)-6-(3-Hydroxypyrrolidin-1-yl)-5-(1H-pyrazol-5-yl)-N-(4-(trifluoromethoxy)phenyl)nicotinamide

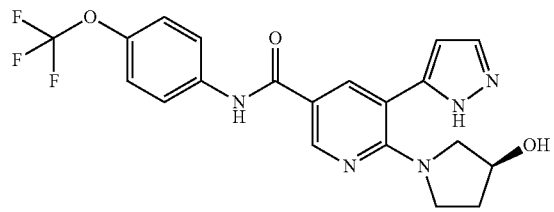

The title compound was prepared in analogous fashion to that described in Example 8 using (S)-5-bromo-6-(3-hydroxypyrrolidin-1-yl)-N-(4-(trifluoromethoxy)phenyl)nicotinamide (Stage 34.1) and 1-(tetrahydro-2H-pyran-2-yl)-5-(4,4,5,5-tetramethyl-1,3,2-dioxaborolan-2-yl)-1H-pyrazole to afford an off-white powder. HPLC (Condition 4) $t_R$=4.42 min, HPLC Chiral (CHIRALPAK® AD-H, 250×4.6 mm, eluent:EtOH/MeCN (98:2), 0.5 mL/min, UV 210 nm) $t_R$=28.27 min, UPLC-MS (Condition 3) $t_R$=0.91 min, m/z=434.2 [M+H]$^+$; $^1$H-NMR (400 MHz, DMSO-d$_6$) δ ppm 1.63-1.88 (m, 2H) 2.92 (d, J=11.73 Hz, 1H) 3.19-3.29 (m, 2H) 3.34-3.47 (m, 1H) 4.18 (br. s, 1H) 4.80 (d, J=3.13 Hz, 1H)

6.37 (s, 1H) 7.31 (d, J=8.99 Hz, 2H) 7.75-7.89 (m, 3H) 8.00 (d, J=2.35 Hz, 1H) 8.71 (d, J=2.35 Hz, 1H) 10.16 (s, 1H) 12.85-13.12 (m, 1H).

Stage 34.1: (S)-5-Bromo-6-(3-hydroxypyrrolidin-1-yl)-N-(4-(trifluoromethoxy)phenyl)nicotinamide

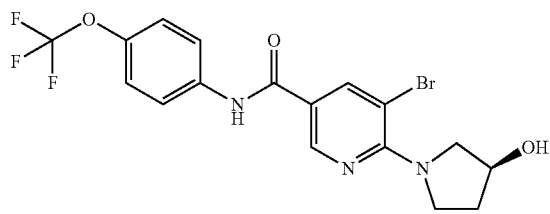 [SMILES: O=C(Nc1ccc(OC(F)(F)F)cc1)c1cnc(N2CC[C@H](O)C2)c(Br)c1]

The title compound was prepared in an analogous fashion to that described in Stage 8.1 using 5-bromo-6-chloro-N-(4-(trifluoromethoxy)phenyl)nicotinamide (Stage 2.3) and (S)-pyrrolidin-3-ol to afford an off-white crystalline powder. HPLC (Condition 4) $t_R$=5.83 min, UPLC-MS (Condition 3) $t_R$=1.06 min, m/z=446.1 [M+H]$^+$.

Example 35

(S)—N-(4-(Chlorodifluoromethoxy)phenyl)-5-(4-fluoro-1H-pyrazol-5-yl)-6-(3-hydroxypyrrolidin-1-yl)nicotinamide

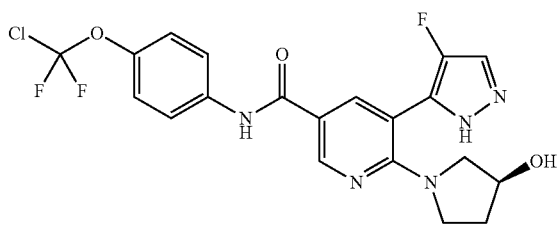 [SMILES: O=C(Nc1ccc(OC(F)(F)Cl)cc1)c1cnc(N2CC[C@H](O)C2)c(-c2[nH]ncc2F)c1]

The title compound was prepared in an analogous fashion to that described in Example 5 using 6-chloro-N-(4-(chlorodifluoromethoxy)phenyl)-5-(4-fluoro-1H-pyrazol-5-yl)nicotinamide (Stage 25.1) and (S)-3-pyrrolidinol to afford a white solid. HPLC (Condition 5) $t_R$=5.69 min, HPLC Chiral (CHIRALCEL® OD-H, 250×4.6 mm, eluent:n-heptane/EtOH/MeOH (85:10:5), 1 mL/min, UV 210 nm) $t_R$=12.62 min, UPLC-MS (Condition 6) $t_R$=0.97 min, m/z=468.2 [M+H]$^+$; $^1$H-NMR (400 MHz, DMSO-d$_6$) δ ppm 1.71-1.81 (m, 1H) 1.81-1.92 (m, 1H) 3.02 (d, J=11.34 Hz, 1H) 3.24-3.37 (m, 2H) 3.40-3.49 (m, 1H) 4.23 (br. s, 1H) 4.89 (br. s, 1H) 7.32 (d, J=9.4 Hz, 2H) 7.76-7.98 (m, J=9.00 Hz, 3H) 8.03 (d, J=2.35 Hz, 1H) 8.79 (d, J=2.35 Hz, 1H) 10.20 (br. s, 1H) 12.99 (br. s, 1H).

Example 36

Methyl 1-(5-((4-(chlorodifluoromethoxy)phenyl)carbamoyl)-3-(1H-pyrazol-5-yl)pyridin-2-yl)pyrrolidine-3-carboxylate

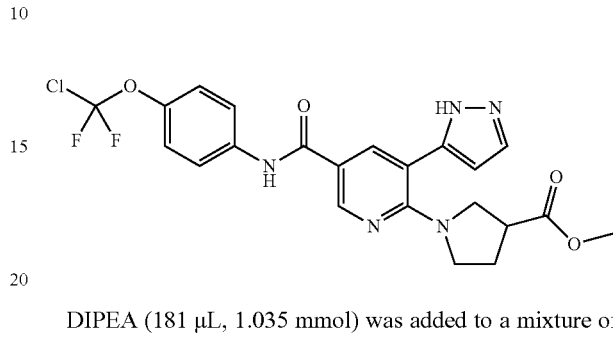

DIPEA (181 µL, 1.035 mmol) was added to a mixture of 6-chloro-N-(4-(chlorodifluoromethoxy)phenyl)-5-(1-(tetrahydro-2H-pyran-2-yl)-1H-pyrazol-5-yl)nicotinamide (Stage 36.1, 100 mg, 0.207 mmol), methyl-3-pyrrolidine carboxylate hydrochloride (44.5 mg, 0.269 mmol) and iPrOH (414 µL). in MW vial, which was flushed with argon, sealed and stirred at 130° C. for 24 h. The RM was diluted with EtOAc, treated with brine and extracted with EtOAc. The combined extracts were dried over Na$_2$SO$_4$ and the solvent was evaporated off under reduced pressure to give the crude product which was purified by flash chromatography (Silica gel column, n-heptane/EtOAc from 40% to 100% EtOAc) followed by preparative TLC (Silica gel, eluent EtOAc). Additional lyophilization from 1,4-dioxane afforded the title compound as a white light solid. UPLC-MS (Condition 6) $t_R$=1.09 min, m/z=492.1 [M+H]$^+$; $^1$H-NMR (400 MHz, DMSO-d$_6$) δ ppm 1.90-2.02 (m, 1H) 2.02-2.14 (m, 1H) 3.06-3.20 (m, 1H) 3.23-3.48 (m, 4H) 3.61 (s, 3H) 6.35-6.48 (m, 1H) 7.34 (d, J=8.78 Hz, 2H) 7.79-7.90 (m, 1H) 7.89 (d, J=8.80 Hz, 2H) 8.03-8.13 (m, 1H) 8.70-8.83 (m, 1H) 10.26 (s, 1H).

Stage 36.1: 6-Chloro-N-(4-(chlorodifluoromethoxy)phenyl)-5-(1-(tetrahydro-2H-pyran-2-yl)-1H-pyrazol-5-yl)nicotinamide

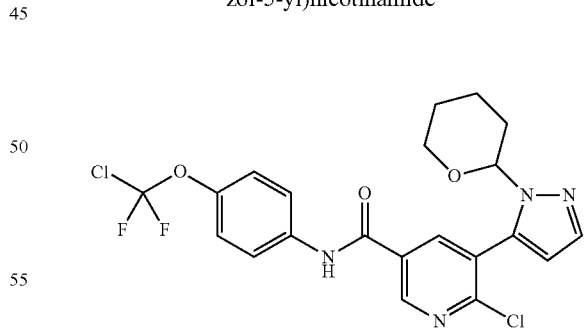

1-(Tetrahydro-2H-pyran-2-yl)-1H-pyrazole-5-boronic acid pinacol ester (9.45 g, 34.0 mmol), Na$_2$CO$_3$ (39.2 mL, 78 mmol) and PdCl$_2$(dppf) (0.956 g, 1.307 mmol) were added to 6-chloro-N-(4-(chlorodifluoromethoxy)phenyl)-5-iodonicotinamide (Stage 25.2, 12 g, 26.1 mmol) in DME (160 mL). The mixture was evacuated/purged 3 times with argon, and stirred at 80° C. for 22 h. The RM was diluted with EtOAc (350 mL), washed with water (4×150 mL) and extracted with EtOAc. The combined extracts were dried over Na$_2$SO$_4$ and the solvent was evaporated off under reduced pressure to give the crude product which was purified by flash chromatography (Silica gel column, 850 g, EtOAc/n-hexane (1:2)) and crystallized from iPr₂O/EtOAc to give the title product as a white solid. HPLC (Condition 5) $t_R$=7.52 min, UPLC-MS (Condition 3) $t_R$=1.22 min, m/z=483/485 [M+H]⁺.

Example 37

1-(5-(4-(Chlorodifluoromethoxy)phenyl)carbamoyl)-3-(1H-pyrazol-5-yl)pyridin-2-yl)pyrrolidine-3-carboxylic acid

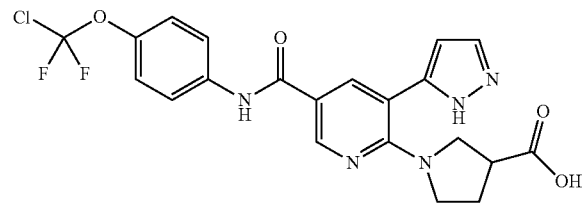 [SMILES: O=C(Nc1ccc(OC(F)(F)Cl)cc1)c1cnc(N2CCC(C(=O)O)C2)c(-c2ccn[nH]2)c1]

Aq. 1 M LiOH (0.199 mL, 0.199 mmol) was added to a solution of methyl 1-(5-((4-(chlorodifluoromethoxy)phenyl) carbamoyl)-3-(1H-pyrazol-5-yl)pyridin-2-yl)pyrrolidine-3-carboxylate (Example 36, 24.5 mg, 0.05 mmol) in MeOH (0.5 mL)/THF (1 mL) and the RM was stirred at RT for 1 h 20. The RM was treated with 1 M HCl (4 eq.) and organic solvents were evaporated off under reduced pressure. The aq. phase was extracted twice with EtOAc and the combined extracts were washed with brine, dried over Na₂SO₄ and the solvent was concentrated under reduced pressure to a volume of 0.5 mL. n-Heptane was added and the product was filtered, washed with n-heptane and dried to afford the title compound as beige solid. UPLC-MS (Condition 6) $t_R$=0.96 min, m/z=478.3 [M+H]⁺; ¹H-NMR (400 MHz, DMSO-d₆) δ ppm 1.86-2.12 (m, 2H) 2.90-3.09 (m, 1H) 3.17-3.54 (m, 4H) 6.41 (d, J=2.08 Hz, 1H) 7.34 (d, J=9.05 Hz, 2H) 7.66-7.83 (m, 1H) 7.88 (d, J=9.17 Hz, 2H) 8.06 (d, J=2.44 Hz, 1H) 8.70-8.84 (m, 1H) 10.23 (s, 1H) 12.90 (br. s, 1H).

Example 38

(S)—(R)-1-(5-(4-(Chlorodifluoromethoxy)phenyl) carbamoyl)-3-(1H-pyrazol-5-yl)pyridin-2-yl)pyrrolidin-3-yl2-amino-3-methylbutanoate

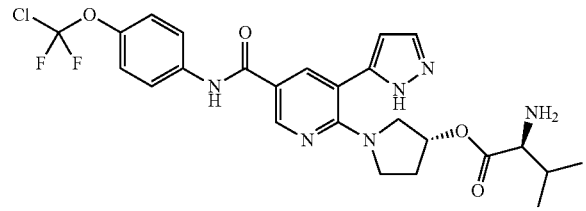 [SMILES: CC(C)[C@H](N)C(=O)O[C@@H]1CCN(c2ncc(C(=O)Nc3ccc(OC(F)(F)Cl)cc3)cc2-c2ccn[nH]2)C1]

Boc-L-Valine (726 mg, 3.34 mmol) and DMAP (102 mg, 0.836 mmol) were added to a mixture of (R)—N-(4-(chlorodifluoromethoxy)phenyl)-6-(3-hydroxypyrrolidin-1-yl)-5-(1H-pyrazol-5-yl)nicotinamide (Example 9, 800 mg, 1.672 mmol) in DCM (20 mL) and the suspension was stirred at RT for 30 min. N,N'-Diisopropyl carbodiimide (0.521 mL, 3.34 mmol) was then added and the resulting solution was stirred at RT for 19 h. The RM was diluted with EtOAc (150 mL), washed with aq. sat. NaHCO₃ solution (50 mL) and brine (2×50 mL) and extracted with EtOAc. The combined extracts were dried over Na₂SO₄ and the solvent was evaporated off under reduced pressure to give a residue which was suspended in EtOAc (5 mL), stirred at RT, filtered and washed with 10 mL EtOAc. The filtrate was evaporated to dryness under reduced pressure and the resulting intermediate was dissolved in DCM (15 mL), treated with TFA (4.09 mL, 53.0 mmol) and was stirred at RT for 92 h. The solvent was evaporated off under reduced pressure and the residue was dissolved in EtOAc (150 mL), washed with aq. sat. NaHCO₃ solution (50 mL) and with water (2×50 mL), dried over Na₂SO₄ and the solvent was evaporated off under reduced pressure to give a residue which was dissolved in MeOH (20 mL), and treated with Si-Thiol (Biotage 1.3 mmol/g, 1 g). Silica gel (5 g) was added to the mixture, the solvent was evaporated off under reduce pressure, and the residue was purified by flash chromatography (RediSep® Silica gel column, 120 g, DCM/MeOH 95:5) followed by preparative SFC (Column DEAP; isocratic 25% in 15 min). The fractions containing pure product were combined and the solvent was evaporated off under reduced pressure to give a residue which was dissolved in hot MeOH (4 mL) and filtered through a PTFE 0.45 μm filter. The filtrate was sonicated for 5 min and the resulting white suspension was stirred for 2 h at RT, filtered, washed with MeOH (1 mL) and dried to give the title product as a white solid. HPLC (Condition 5) $t_R$=5.41 min, UPLC-MS (Condition 3) $t_R$=0.86 min, m/z=549.2 [M+H]⁺; ¹H-NMR (400 MHz, DMSO-d₆) δ ppm 0.77 (d, J=6.65 Hz, 3H) 0.81 (d, J=6.65 Hz, 3H) 1.51-1.64 (m, 2H) 1.69-1.81 (m, 1H) 1.84-1.94 (m, 1H) 1.98-2.12 (m, 1H) 3.02 (d, J=5.08 Hz, 1H) 3.15 (d, J=12.90 Hz, 1H) 3.30-3.43 (m, 2H) 3.46-3.57 (m, 1H) 5.13-5.25 (m, 1H) 6.39 (br. s, 1H) 7.31 (d, J=8.21 Hz, 2H) 7.76-7.91 (m, 3H) 8.05 (s, 1H) 8.73 (br. s, 1H) 10.21 (s, 1H) 12.94 (br. s, 1H).

Example 39

(R)-1-(5-(4-(Chlorodifluoromethoxy)phenyl)carbamoyl)-3-(1H-pyrazol-5-yl)pyridin-2-yl)pyrrolidin-3-yl dihydrogen phosphate

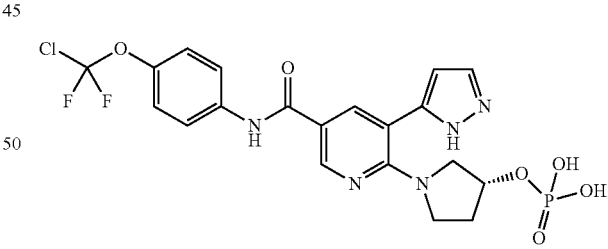

TFA (1.227 mL, 15.93 mmol) was added to a solution of N-(4-(chlorodifluoromethoxy)phenyl)-6-(R)-3-((3-oxido-1,5-dihydrobenzo[e][1,3,2]dioxaphosphepin-3-yl)oxy)pyrrolidin-1-yl)-5-(1-(tetrahydro-2H-pyran-2-yl)-1H-pyrazol-5-yl)nicotinamide (Stage 39.1, 620 mg, 0.797 mmol) in DCM (10 mL) and the RM was stirred for 20 h at RT. Additional TFA (500 μL) was added and the RM was stirred for further 4 h at RT. The RM was diluted with EtOAc (100 mL), treated with sat. aq. Na₂CO₃ (70 mL) and extracted with EtOAc (50 mL). The combined extracts were washed with brine (50 mL), dried over Na₂SO₄ and the solvent was evaporated off under reduced pressure to give a residue which was purified by flash chromatography (Silica gel column, 12 g DCM/EtOH from 9:1 to 4:6). The intermediate was dissolved in MeOH/THF (10 mL of 1:1) and hydrogenated (60 mg Pd/C 5%, 0.1 bar, 22-25° C., 6.5 h). The RM was filtered through Hyflo® and solvent was evaporated off under reduced pressure. The residue was dissolved in MeOH/THF and was treated with a PL-Thiol MP SPE cartridge (StratoSpheres™). The resin was filtered off and the solvent was evaporated off under reduced pressure to give the title product. HPLC (Condition 5) $t_R$=5.50 min, UPLC-MS (Condition 6) $t_R$=0.76 min, m/z=530.2 [M+H]$^+$; $^1$H-NMR (400 MHz, DMSO-d$_6$) δ ppm 1.88-2.08 (m, 2H) 3.12-3.48 (m, 4H) 4.73 (br. s, 1H) 6.37-6.44 (m, 1H) 7.33 (d, J=8.99 Hz, 2H) 7.76 (s, 1H) 7.87 (d, J=8.99 Hz, 2H) 8.04-8.08 (m, 1H) 8.73-8.78 (m, 1H) 10.21 (s, 1H).

Stage 39.1: N-(4-(Chlorodifluoromethoxy)phenyl)-6-(R)-3-((3-oxido-1,5-dihydrobenzo[e][1,3,2]dioxaphosphepin-3-yl)oxy)pyrrolidin-1-yl)-5-(1-(tetrahydro-2H-pyran-2-yl)-1H-pyrazol-5-yl)nicotinamide

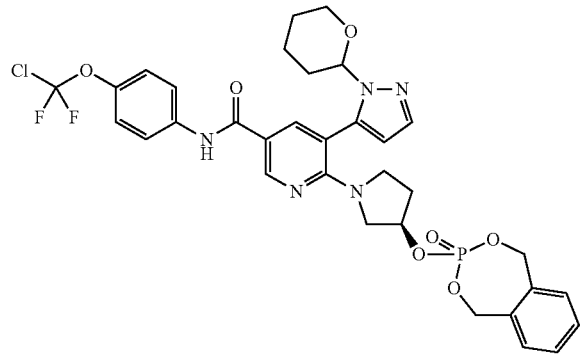 [SMILES: O=C(Nc1ccc(OC(F)(F)Cl)cc1)c1cnc(N2CC[C@@H](OP3(=O)OCc4ccccc4CO3)C2)c(-c2ccnn2C2CCCCO2)c1]

N,N-diethyl-1,5-dihydrobenzo[e][1,3,2]dioxaphosphepin-3-amine (355 mg, 1.483 mmol) was added to a mixture of N-(4-(chlorodifluoromethoxy)phenyl)-6-(R)-3-hydroxypyrrolidin-1-yl)-5-(1-(tetrahydro-2H-pyran-2-yl)-1H-pyrazol-5-yl)nicotinamide (Stage 9.1, 200 mg, 0 371 mmol) and tetrazole in MeCN (8.240 mL, 3.71 mmol) in a vial and the RM was stirred at RT for 3 h. The RM was cooled to 5° C., treated with TEA (0.775 mL, 5.56 mmol) and aq. H$_2$O$_2$ (0.379 mL, 3.71 mmol) and was stirred at 0° C. for 30 min followed by 3 h at RT. The RM was quenched with a solution of 10% Na$_2$S$_2$O$_3$ (20 mL) and extracted with EtOAc. The combined extracts were washed with water (20 mL) and brine (15 mL), dried over Na$_2$SO$_4$ and the solvent was evaporated off under reduced pressure to give the crude product which was purified by flash chromatography (Silica gel column, 12 g DCM/MeOH from 98:2 to 9:1) to give the title product as a white foam. HPLC (Condition 5) $t_R$=7.3 min, UPLC-MS (Condition 3) $t_R$=1.18 min, m/z=716.3 [M+H]$^+$.

Example 40

(R)-1-(3-(1H-Pyrazol-5-yl)-5-(4-(trifluoromethoxy)phenyl)carbamoyl)pyridin-2-yl)pyrrolidin-3-yl dihydrogen phosphate

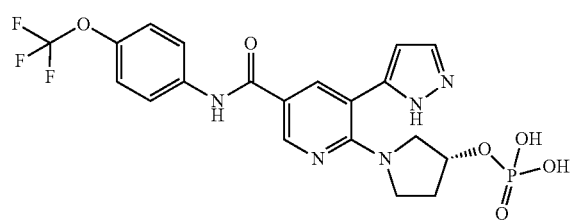 [SMILES: O=C(Nc1ccc(OC(F)(F)F)cc1)c1cnc(N2CC[C@@H](OP(=O)(O)O)C2)c(-c2ccn[nH]2)c1]

The title compound was prepared in an analogous fashion to that described in Example 39 using (R)-6-(3-hydroxypyrrolidin-1-yl)-5-(1H-pyrazol-3-yl)-N-(4-(trifluoromethoxy)phenyl)nicotinamide (Stage 2.1) and N,N-diethyl-1,5-dihydrobenzo[e][1,3,2]dioxaphosphepin-3-amine to afford a beige solid. HPLC (Condition 5) $t_R$=5.3 min, UPLC-MS (Condition 6) $t_R$=0.75 min–m/z=514.4 [M+H]$^+$; $^1$H-NMR (400 MHz, DMSO-d$_6$) δ ppm 1.88-2.07 (m, 2H) 3.21-3.49 (m, 4H) 4.66-4.76 (m, 1H) 6.41 (d, J=1.96 Hz, 1H) 7.02-7.15 (m, 1H) 7.34 (d, J=8.68 Hz, 2H) 7.77 (s, 1H) 7.87 (d, J=9.05 Hz, 2H) 8.06 (d, J=2.32 Hz, 1H) 8.75 (d, J=2.32 Hz, 1H) 10.21 (s, 1H).

Example 41

Solid Dispersion Formulation

A solid dispersion formulation can be prepared for compounds of the invention where enhancing their solubility is beneficial for bioavailability and/or permeability.

The solid dispersion formulation was prepared using an amorphous dispersion of (R)—N-(4-(chlorodifluoromethoxy)phenyl)-6-(3-hydroxypyrrolidin-1-yl)-5-(1H-pyrazol-5-yl)nicotinamide (Example 9, see FIG. 1) with excipients selected from PVP VA64 and Pharmacoat 603. First, a solution for spray drying was prepared by mixing (R)—N-(4-(chlorodifluoromethoxy)phenyl)-6-(3-hydroxypyrrolidin-1-yl)-5-(1H-pyrazol-5-yl)nicotinamide (Example 9, 2.5 grams) with PVP VA 64 (3.75 grams) and Pharmacoat 603 (3.75 grams). A mixture of 50/50 methylene chloride/ethanol was added until all components were dissolved as shown by a clear solution free of particulates and haze (~200 mL). Alternatively, the mixture of 50/50 methylene chloride/ethanol can be substituted with an acetone/ethanol/water (5:4:1) mixture. Spray drying was carried out on a Büchi B290 Mini-spray drier with an inlet temperature of 70° C., aspiration at 85%, nitrogen flow at 50 mm of Hg, pump at 15% and the nozzle cleaner was zero to yield 5.5 grams (55%). The resultant spray-dried solid dispersion contained 23.6% Drug Load of (R)—N-(4-(chlorodifluoromethoxy)phenyl)-6-(3-hydroxypyrrolidin-1-yl)-5-(1H-pyrazol-5-yl)nicotinamide (Example 9), 37.5% PVP VA64 and 37.5% Pharmacoat 603. The dispersion was amorphous with a glass transition temperature ($T_g$) value of 117° C. and contained approximately 1.4% water as determined by thermogravimetric analysis (TGA). Dissolution of this solid dispersion in pH 1 followed by a pH switch to 6.8 after 30 minutes showed full dissolution under acidic pH. The dispersion remained fully solubilized after a pH challenge to neutral pH.

The dispersion was suspended in phosphate buffered saline (PBS) at a concentration of 3 mg/mL (as drug) for 12 hours at room temperature. No crystallization was noted, the particle size D (0.9; the diameter of the particle where 90% of the particles are below this number stated) was 14.134 with very homogeneous and narrow particle size distribution. The drug did not crystallize out of suspension and no chemical degradation was noted (as evaluated by UPLC). The suspension had a chemical purity of 99.4%, which matched the T0 purity of the suspension and the drug itself.

The enhanced properties of the solid dispersion formulation of (R)—N-(4-(chlorodifluoromethoxy)phenyl)-6-(3-hydroxypyrrolidin-1-yl)-5-(1H-pyrazol-5-yl)nicotinamide (Example 9) in dog can be demonstrated by the table of pharmacokinetic parameters, below.

|  | Type of formulation | |
| --- | --- | --- |
|  | Solid Dispersion | Suspension |
| Dose [mg/kg] | 60 | 60 |
| AUC [mM * h] (SD) | 671.9 | 102.9 |
| $c_{Max}$ [nM] (SD) | 47127 | 7314 |
| BAV* [%] (SD) | 179.1 | 27.4 |
| Tmax [h] (SD) | 2.00 | 3.3 |
| Volume of Administration [ml/kg] | 5 | 5 |
| Rank exposure/$c_{Max}$ | 14.2 | 14.1 |

The solid dispersion formulation of (R)—N-(4-(chlorodifluoromethoxy)phenyl)-6-(3-hydroxypyrrolidin-1-yl)-5-(1H-pyrazol-5-yl)nicotinamide (Example 9) at a dose of 60 mpk gave 6.5 times more exposure than the crystalline suspension (671.9 µM versus 102.9 µm).

Assays

The utility of the compounds of the invention described herein can be evidenced by testing in the following assays. Compounds of the invention were assessed for their ability to inhibit ABL1 activity in biochemical assays and BCR-ABL1 in cellular assays described below. Compounds of the invention were further tested and shown to be efficacious in vivo using a KCL-22 xenograft model.

Biochemical Assays

Expression and purification of protein kinase—Expression and purification of human ABL was performed using standard expression purification procedures. The ABL64-515 protein was generated and used for in vitro kinase assays. The protein was generated by a co-expression vector carrying the DNA fragments for ABL1 (1a isoform, with an N-terminal His6-tag followed by a PreScission protease cleavage site) and the human protein tyrosine phosphatase-1B (residues 1-283, untagged), using the dual expression vector pCDF Duet-1 (Novagen). The His-ABL was expressed in *E. coli* BL21 (DE3) and the ABL proteins were isolated by Ni-affinity on a Ni-NTA column (Qiagen). The His-tag was removed by PreScission protease (GE Healthcare) and the non-phosphoprylated ABL further purified on a Mono Q HR 10/10 (GE Healthcare, mono-phosphorylated ABL is about 10-20% of total ABL protein) and HiLoad 16/60 Superdex 200 size exclusion column (GE Healthcare). Non-phosphorylated ABL64-515 proteins were analyzed by mass spectroscopic analysis and flash-frozen in aliquots and stored at −80°

C. SRC (amino acids 83-535 or Src83-535) was expressed and purified as described (S. W. Cowan-Jacob, G. Fendrich, P. W. Manley, W. Jahnke, D. Fabbro, J. Liebetanz, T. Meyer, c-Src crystal structure provides insights into c-Src activation. Structure 13 (2005) 861-871).

Radio ABL1 (64-515) Assay

For determination of ABL kinase activity, the radiometric filter-binding assay was used. The assay was performed by mixing 10 µL of the compound pre-diluted with 10 µL of ATP (20 µM ATP with 0.1 µCi [γ-33P]-ATP) with the phosphoacceptor peptide poly[Ala6Glu2LysHBr5Tyr1]=polyAEKY) in 20 mM Tris/HCl pH 7.5, 1 mM DTT, 10 mM $MgCl_2$, 0.01 mM $Na_3VO_4$, 50 mM NaCl. 10 µL of enzyme (ranging between 5 nM to 20 nM) was added to initiate the reaction. Pre-incubation of enzyme with compounds (when stated) was performed by exposing the enzyme to compounds prior to addition of the substrate mixture (ATP and/or peptide substrate). After 15 min at room temperature, the reaction was stopped by the addition of 50 µL 125 mM EDTA, and the peptide-bound 33P separated on filter-plates (PVDF or MAIP; Millipore, Volketswil, Switzerland) prepared according to the manufacturer's instructions. Filter-plates were washed 3× with 0.5% $H_3PO_4$, followed by addition of 30 µL scintillation cocktail (Microscint, Perkin Elmer) per well and then analysed in a TopCount NXT scintillation counter (Perkin Elmer). Results were expressed as $IC_{50}$ values. The $K_m$ values for ATP were determined by assaying the ABL kinase with increasing concentrations of ATP and keeping the exogenous acceptor protein substrate (poly-AEKY) at a constant concentration (at about 2-fold its $K_m$) and vice versa. $K_m$ and $V_{max}$ were calculated according to Eadie-Hofstee as described (D. Fabbro, G. Fendrich, V. Guez, T. Meyer, P. Furet, J. Mestan, J. D. Griffin, P. W. Manley, S. W. Cowan-Jacob, Targeted therapy with imatinib: An exception or a rule? Handbook of Experimental Pharmacology 167, Inhibitors of Protein Kinases and Protein Phosphates (2005) 361-389). The data were plotted as V versus V/S, where V is the velocity of the reaction at a given substrate (S) concentration, and fitted to a straight line using linear regression analysis, where the slope of the line corresponds to $-K_m$ and the Y-intercept represents the $V_{max}$.

Caliper ABL1 (64-515) Assay

All assays were performed in 384-well microtiter plates. Each assay plate contained 8-point serial dilutions for 40 test compounds, as well as four 8-point serial dilutions of staurosporine as a reference compound, plus 16 high and 16 low controls. Liquid handling and incubation steps were done on a Thermo CatX workstation equipped with Innovadyne Nanodrop Express. Between pipetting steps, tips were cleaned in wash cycles using wash buffer.

The assay plates were prepared by addition of 50 mL per well of compound solution in 90% DMSO. The kinase reactions were started by stepwise addition of 4.5 µL per well of peptide/ATP-solution (50 mM HEPES, pH 7.5, 1 mM DTT, 0.02% BSA, 0.6% DMSO, 10 mM beta-glycerophosphate, and 10 µM sodium orthovanadate, 20 mM $MgCl_2$, 2 mM $MnCl_2$, 4 µM ATP, 4 µM peptide (FITC-Ahx-EAIYAAP-FAKKK-NH2)) and 4.5 µL per well of enzyme solution (50 mM HEPES, pH 7.5, 1 mM DTT, 0.02% BSA, 0.6% DMSO, 10 mM beta-glycerophosphate, and 10 µM sodium orthovanadate, 20 mM $MgCl_2$, 2 mM $MnCl_2$, 3.5 nM ABL (ABL (64-515), produced in-house from *E. coli*)). Kinase reactions were incubated at 30° C. for 60 minutes and subsequently terminated by addition of 16 µL per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated peptide (product) and unphosphorylated peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Preparation of compound dilutions: Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96-well plates. This format enabled the assay of maximally 40 individual test compounds at 8 concentrations (single points) including 4 reference compounds. The dilution protocol included the production of "pre-dilution plates", "master plates" and "assay plates".

Pre-dilution plates: Polypropylene 96-well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 30 µL of individual compound dilutions including standard compound and controls of the 4 "pre-dilution plates" were transferred into a 384 "master plate" including the following concentrations 1'810, 362, 72.5, 54.6, 14.5, 2.9, 0.58 and 0.12 µM, respectively in 90% of DMSO.

Assay plates: Identical "assay plates" were then prepared by pipetting 50 nL each of compound dilutions of the "master plates" into 384-well "assay plates" by means of a Humming-Bird 384-channel dispenser. These plates were used directly for the assay which was performed in a total volume of 9.05 µL. This led to a final compound concentration of 10, 2.0, 0.4, 0.08, 0.016, 0.0032, 0.00064 and 0.000128 µM and a final DMSO concentration of 0.5% in the assay.

Cellular Assays

To assess the ability of compounds of the invention to inhibit BCR-ABL1 activity in cellular assays, compounds were evaluated for their ability to selectively inhibit the proliferation of cells dependent on BCR-ABL1 expression relative to cells that do not depend on BCR-ABL1 expression.

The murine bone marrow-derived cell line Ba/F3 was used to generate the appropriate cell line models. Ba/F3 cells were obtained from the German Collection of Microorganisms and Cell Cultures (DSMZ, Braunschweig and DSMZ No. ACC 300). Parental Ba/F3 cells depend on IL3 for growth and survival and were used as the reference cell line that does not depend on BCR-ABL1 activity for growth and survival. These cells are referred to as Ba/F3-WT.

To generate Ba/F3 cells that depend on BCR-ABL1 expression for growth and survival, Ba/F3 cells were engineered to express BCR-ABL1 using retroviral transduction with a MSCV based retroviral vector containing a p210 BCR-ABL1expression cassette. When grown in the absence of IL-3, the proliferation of the cells is dependent on the expression of BCR-ABL1. (Daley, G. Q. and Baltimore, D. Transformation of an interleukin 3-dependent hematopoietic cell line by the chronic myeloid leukemia-specific p210 BCR-ABL1 protein. PNAS 1988; 85:9312-9316). These cells are referred to as Ba/F3-BCR-ABL-WT. A similar approach was used to generate Ba/F3 cells that depend on a BCR-ABL1 variant in which threonine 315 is replaced with isoleucine. These cells are referred to as Ba/F3-BCR-ABL-T315I.

Ba/F3-WT cells were maintained in RPMI1640 media with L-glutamine, HEPES (Lonza), 10% FBS (Gibco) and 5 ng/ml IL-3 (Calbiochem). Ba/F3-BCR-ABL1-WT cells and Ba/F3-BCR-ABL1-T315I cells were manitained in RPMI1640 media with L-glutamine, HEPES (Lonza) and 10% FBS (Gibco).

Proliferation Assay

For each cell line, the cell density was adjusted to 50 000 cells/mL and 50 µL (2500 cells) added per well of a 384-well assay plate.

Test compounds were resuspended in DMSO at a concentration of 10 mM. A serial three-fold dilution of each compound with DMSO was performed in 384-well plates using the Janus Liquid Dispenser (PerkinElmer). Compound was delivered to the assay plates containing 2500 cells in a 50 µL volume via Acoustic delivery from an ATS-100 (EDC). For Ba/F3-BCR-ABL1-WT cell assays, 2 mL of each compound dilution was transferred to the assay plate for final assay concentrations of 0.4 µM, 0.13 µM, 0.044 µM, 0.015 µM, 0.005 µM, 0.001 µM, 0.00033 µM, 0.00011 µM, 0.000037 µM, 0.000012 µM. For Ba/F3-WT and Ba/F3-BCR-ABL1-T315I cell assays, 50 mL of each compound dilution was transferred to the assay plate for final assay concentrations of 10 µM, 3.33 µM, 1.11 µM, 0.37 µM, 0.12 µM, 0.041 µM, 0.014 µM, 0.0046 µM, 0.0015 µM, 0.00051 µM.

Cells were incubated at 37° C. in a humidified environment with 5% carbon dioxide for 48 hours. Britelite plus solution (Perkin Elmer) was prepared according to the manufacturer's instructions and 25 µL added to each well of the assay plate. Plates were incubated for 3-5 minutes and the luminescence detected on an EnVision Multimode plate reader (Perkin Elmer). The degree of luminescence correlates with the number of cells in each well. The effect of each inhibitor concentration can therefore be calculated and $IC_{50}$ values generated.

The compounds of the invention show $IC_{50}$ values in the range of 0.1 nM to 12 nM for inhibition of Abl kinase activity in a radiometric filter binding (Radio). For a microfluidic mobility shift assays (Caliper) assay, $IC_{50}$ values can be found in the range of 0.1 nM to 10 nM. For Ba/F3-BCR-ABL-WT and T315I cellular proliferation assay, $GI_{50}$ values can be found in the range of 0.8 nM to 110 nM and 13 nM to 4.2 µM, respectively.

| | Table of Biochemical Data | |
|---|---|---|
| Example | Radio ABL1 (64-515) $IC_{50}$ [µM] | Caliper ABL1 (64-515) $IC_{50}$ [µM] |
| 1 | <0.003 | 0.0022 |
| 2 | 0.004 | 0.001 |
| 3 | 0.004 | 0.0007 |
| 4 | 0.0034 | 0.0013 |
| 5 | 0.007 | 0.0012 |
| 6 | 0.003 | 0.0032 |
| 7 | <0.003 | 0.0004 |
| 8 | 0.0019 | 0.0004 |
| 9 | 0.0024 | 0.0003 |
| 10 | <0.00013 | 0.0003 |
| 11 | <0.003 | <0.00013 |
| 12 | 0.006 | 0.0005 |
| 13 | 0.01 | 0.0006 |
| 14 | 0.01 | 0.0009 |

Table of Biochemical Data

| Example | Radio ABL1 (64-515) IC$_{50}$ [µM] | Caliper ABL1 (64-515) IC$_{50}$ [µM] |
|---|---|---|
| 15 | 0.011 | 0.0003 |
| 16 | 0.012 | <0.00013 |
| 17 | 0.003 | 0.0024 |
| 18 | 0.002 | 0.0002 |
| 19 | 0.005 | 0.0018 |
| 20 | 0.0013 | 0.0004 |
| 21 | 0.001 | 0.0013 |
| 22 | 0.006 | <0.00064 |
| 23 | 0.007 | 0.0005 |
| 24 | 0.005 | 0.0004 |
| 25 | 0.001 | 0.0007 |
| 26 | 0.012 | 0.0104 |
| 27 | 0.002 | 0.0011 |
| 28 | 0.0028 | 0.0019 |
| 29 | 0.009 | 0.0009 |
| 30 | 0.0004 | 0.0043 |
| 31 | 0.001 | 0.0025 |
| 32 | 0.003 | 0.013 |
| 33 | 0.0060 | 0.0006 |
| 34 | 0.0020 | 0.0041 |
| 35 |  | 0.0004 |
| 36 |  | 0.0021 |
| 37 |  | 0.0005 |
| 38 | 0.0040 | 0.0025 |
| 39 | 0.0030 | 0.0013 |
| 40 |  | 0.0021 |

Table of Cellular Proliferation Data
Ba/F3-BCR-ABL1-WT and T315I

| Example | Ba/F3-BCR-ABL1-WT IC$_{50}$ [µM] | Ba/F3-BCR-ABL1-T315I IC$_{50}$ [µM] |
|---|---|---|
| 2 | 0.0048 | 0.135 |
| 3 | 0.0075 | 0.133 |
| 4 | 0.0117 | 0.327 |
| 5 | 0.0081 | 0.134 |
| 7 | 0.0060 | 0.132 |
| 8 | 0.0022 | 0.065 |
| 9 | 0.0015 | 0.035 |
| 10 | 0.0019 | 0.044 |
| 11 | 0.001 | 0.038 |
| 12 | 0.0019 | 0.038 |
| 13 | 0.0096 | 0.150 |
| 14 | 0.0189 | 0.218 |
| 15 | 0.0019 | 0.031 |
| 16 | 0.0041 | 0.092 |
| 17 | 0.0155 | 0.199 |
| 18 | 0.0015 | 0.032 |
| 19 | 0.0135 | 0.236 |
| 21 | 0.004 | 0.149 |
| 23 | 0.0017 | 0.042 |
| 24 | 0.0011 | 0.022 |
| 25 | 0.0011 | 0.023 |
| 26 | 0.0090 | 0.227 |
| 28 | 0.0075 | 0.150 |
| 30 | 0.0318 | 0.715 |
| 31 | 0.0041 | 0.133 |
| 33 | 0.0015 | 0.032 |
| 34 | 0.0150 | 0.212 |
| 35 | 0.0008 | 0.013 |
| 36 | 0.0019 | 0.071 |

In Vivo Efficacy in KCL-22 Xenograft Model—Single Agent Treatment

Compounds of the invention were dosed orally in a mouse KCL-22 xenograft model for 7 days. 6-8 week old female nude mice purchased from Harlan (Indianapolis Ind.) were implanted subcutaneously with 5×10$^6$ KCL-22 cells in 50% matrigel (BD Biosciences, #354234) in the right dorsal axillary region. Drug treatment was initiated when tumor volume reached an average of 238 mm$^3$ (10 days post tumor implantation). Compounds of the invention in phosphate buffered saline were prepared weekly and dosed by oral gavage at 3-30 mg/kg twice daily (n=6 mice per dose level). Tumor volume was determined by twice weekly digital calipering and calculated as Length×Width$^2$/2.

Figure 2:
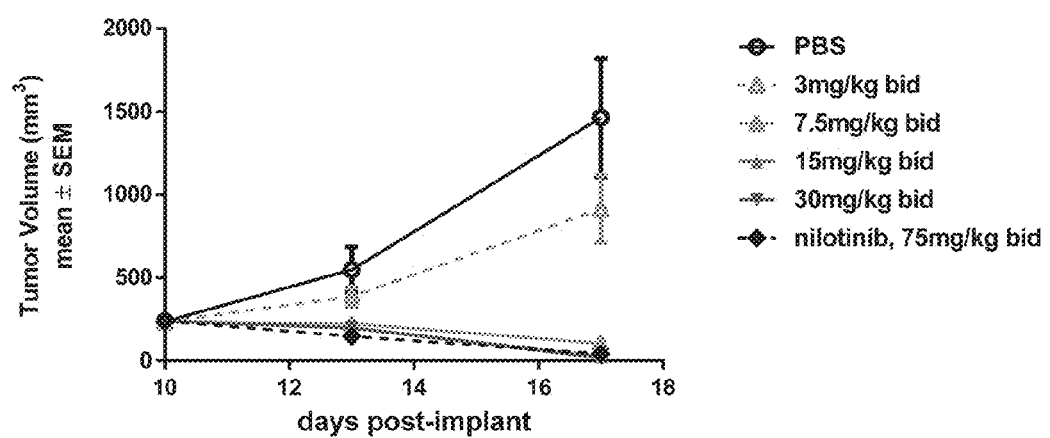
FIG. 2: Animals with subcutaneous KCL-22 xenografts received daily treatment with Example 9. Dose-dependent antitumor activity was demonstrated.

Compounds of the invention showed statistically significant regressions. For example, a 3 mg/kg twice daily dose of (R)—N-(4-(Chlorodifluoromethoxy)phenyl)-6-(3-hydroxy-pyrrolidin-1-yl)-5-(1H-pyrazol-5-yl)nicotinamide (Example 9) led to a tumor growth inhibition of 45% compared to vehicle-treated mice, while regressions were observed of 56%, 88% and 92% at doses of 7.5, 15 and 30 mg/kg twice daily dosing, respectively. As a positive control, nilotinib was dosed at 75 mg/kg twice daily resulting in a tumor regression of 82% (FIG. 2).

In Vivo Efficacy in KCL-22 Xenograft Model—Dual Agent Treatment 6-8 week old female nude mice purchased from Harlan (Indianapolis Ind.) were implanted subcutaneously with 2×10$^6$ KCL-22 cells in 50% matrigel (BD Biosciences, #354234) in the right dorsal axillary region. Drug treatment was initiated when tumor volume reached an average of 189 mm$^3$ (9 days post tumor implantation). Compounds of the invention in a phosphate-buffered saline solution were prepared weekly and dosed by oral gavage at 30 mg/kg twice daily, and Nilotinib solution was dosed at 75 mg/kg twice daily. Animals received either single agent alone or combination of both simultaneously. Tumor volume was determined by twice weekly digital calipering and calculated as Length×Width$^2$/2.

Figure 3:
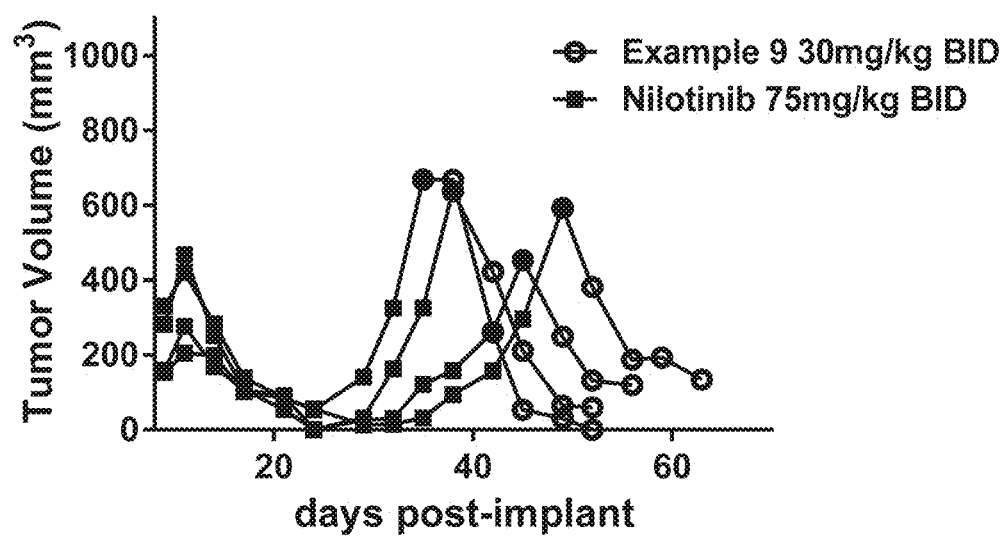
FIG. 3: KCL-22 cells were grown as sub-cutaneous xenografts and four animals were dosed with 75 mg/kg Nilotinib BID (twice daily). When tumors developed resistance to treatment with Nilotinib the dosing was changed to 30 mg/kg Example 9 BID. The treatment of nilotinib resistant tumors with Example 9 led to regression of the tumors. Each line represents a separate animal.

Animals treated with nilotinib alone achieved >84% tumor regression after 4 week daily treatment, but most tumors relapsed to >500 mm$^3$ thereafter. Animals with nilotinib-resistant tumors then received daily treatment of Example 9, and continued to be monitored for tumor response (FIG. 3).

Figure 4:
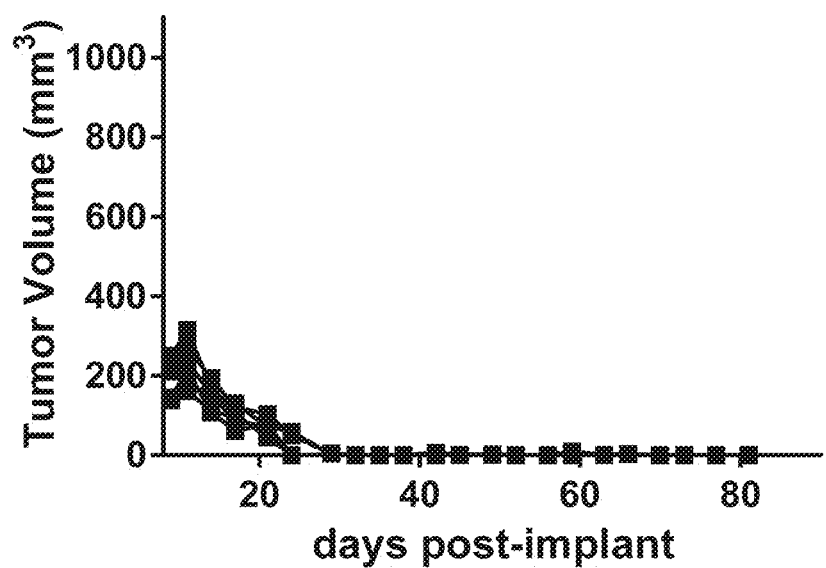
FIG. 4: Animals with subcutaneous KCL-22 xenografts were dosed with a combination of 30 mg/kg Example 9 BID and 75 mg/kg Nilotinib BID. Each line represents a separate animal. Complete tumor regression was seen in all animals and was maintained to the end of the study.

Animals treated with nilotinib and Example 9 simultaneously demonstrated complete tumor regression in all animals to the end of the study (FIG. 4).

It is understood that the Examples and embodiments described herein are for illustrative purposes only and that various modifications or changes in light thereof will be suggested to persons skilled in the art and are to be included within the spirit and purview of this application and scope of the appended claims.

We claim:

1. The compound of formula (I):

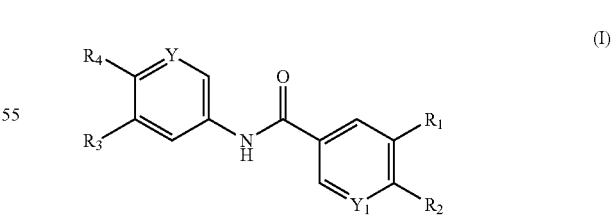

in which:
$R_1$ is pyrazolyl; wherein said pyrazolyl is unsubstituted or substituted with 1 to 2 $R_6$ groups;
$R_2$ is pyrrolidinyl; wherein said pyrrolidinyl is substituted with one $R_7$ group;
$R_3$ is selected from hydrogen and halo;
$R_4$ is selected from —SF$_5$ and —Y$_2$—CF$_2$—Y$_3$;

R₆ at each occurrence is independently selected from hydrogen, hydroxy, methyl, methoxy, cyano, trifluoromethyl, hydroxy-methyl, halo, amino, fluoro-ethyl, ethyl and cyclopropyl;

R₇ is selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyloxy, carboxy, methoxy-carbonyl, phosphonooxy, cyano and amino-carbonyl;

Y is selected from CH and N;
Y₁ is selected from CH and N;
Y₂ is selected from CF₂, O and S(O)₀₋₂; and
Y₃ is selected from hydrogen, chloro, fluoro, methyl, difluoromethyl and trifluoromethyl; or the pharmaceutically acceptable salts thereof.

2. The compound of claim 1 of formula (Ib):

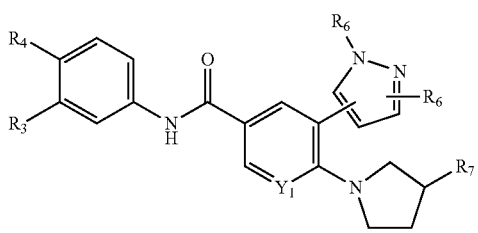

(Ib)

in which:
R₃ is selected from hydrogen and halo;
R₄ is selected from —SF₅ and —Y₂—CF₂—Y₃;
R₆ when linked to a nitrogen of the pyrazolyl ring is selected from hydrogen, methyl, hydroxy-ethyl, fluoroethyl, ethyl and cyclopropyl; and R₆ when linked to a carbon atom of the pyrazolyl ring is selected from hydrogen, hydroxy, methyl, methoxy, cyano, trifluoromethyl, hydroxy-methyl, halo, amino, fluoro-ethyl, ethyl and cyclopropyl;
R₇ is selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyloxy, carboxy, methoxy-carbonyl, phosphonooxy, cyano and amino-carbonyl;
Y₁ is selected from CH and N;
Y₂ is selected from CF₂, O and S(O)₀₋₂;
Y₃ is selected from hydrogen, fluoro, chloro, methyl, difluoromethyl and trifluoromethyl; or the pharmaceutically acceptable salts thereof.

3. The compound of claim 2 of formula (Ic):

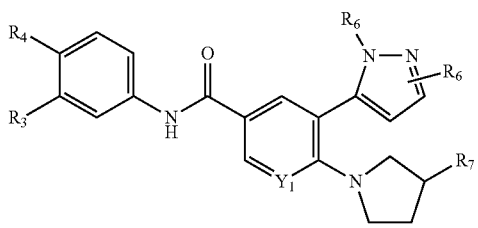

(Ic)

in which:
R₃ is selected from hydrogen and halo;
R₄ is selected from —SF₅ and —Y₂—CF₂—Y₃;
R₆ when linked to a nitrogen of the pyrazolyl ring is selected from hydrogen, methyl, hydroxy-ethyl, fluoroethyl, ethyl and cyclopropyl; and R₆ when linked to a carbon atom of the pyrazolyl ring is selected from hydrogen, hydroxy, methyl, methoxy, cyano, trifluoromethyl, hydroxy-methyl, halo, amino, fluoro-ethyl, ethyl and cyclopropyl;
R₇ is selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyloxy, carboxy, methoxy-carbonyl, phosphonooxy, cyano and amino-carbonyl;
Y₁ is selected from CH and N;
Y₂ is selected from CF₂, O and S(O)₀₋₂;
Y₃ is selected from hydrogen, fluoro, chloro, methyl, difluoromethyl and trifluoromethyl; or the pharmaceutically acceptable salts thereof.

4. The compound of claim 3, or a pharmaceutically acceptable salt thereof, selected from:

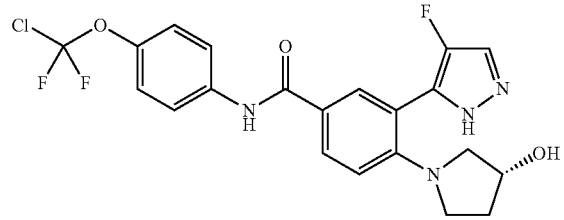

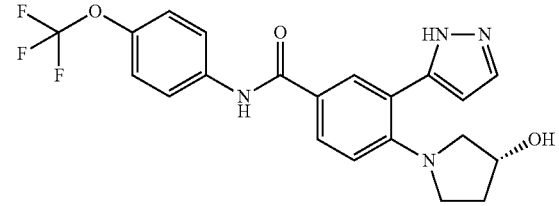

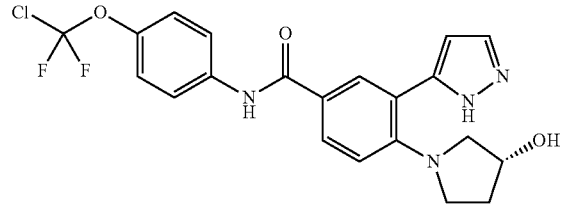

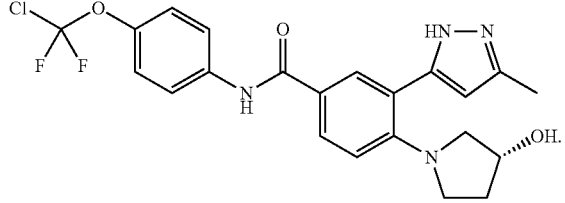

5. The compound of claim 3, or a pharmaceutically acceptable salt thereof, selected from:
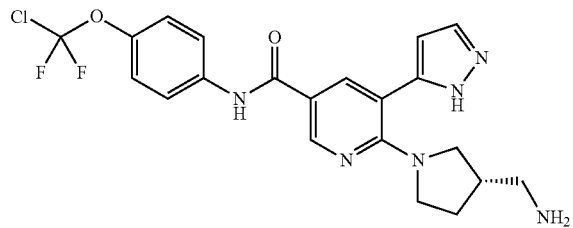
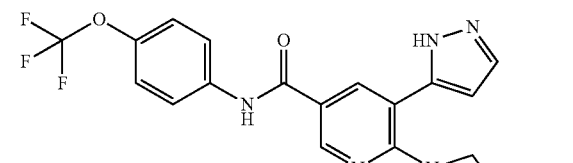
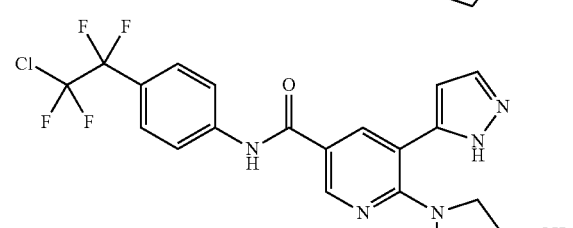
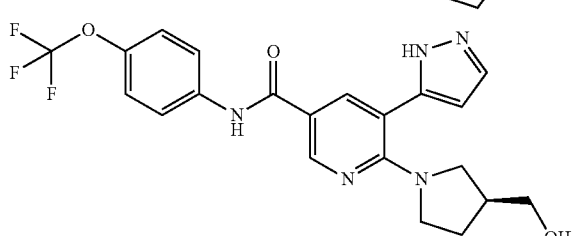
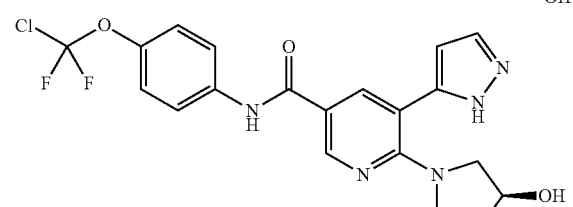
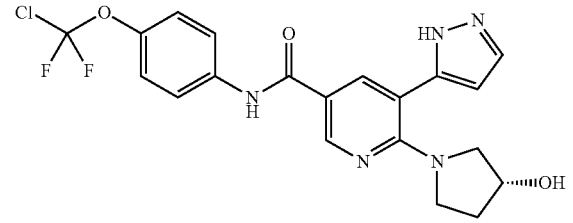
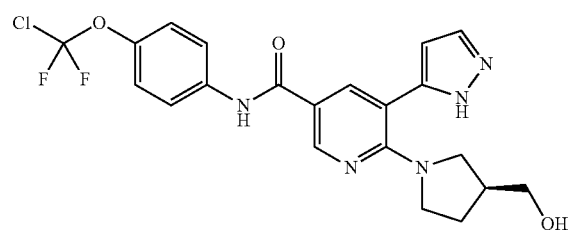
-continued
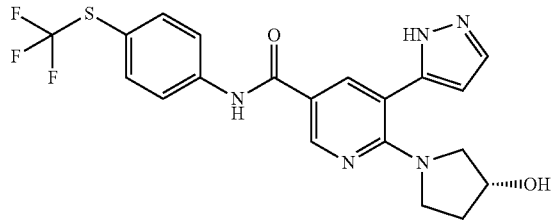
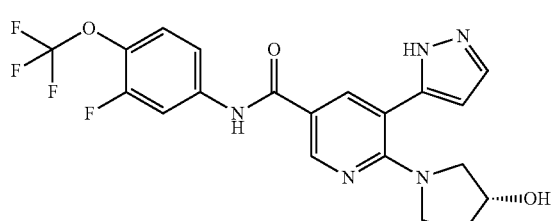
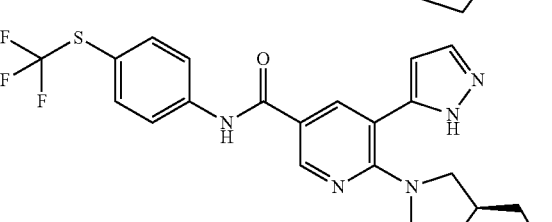
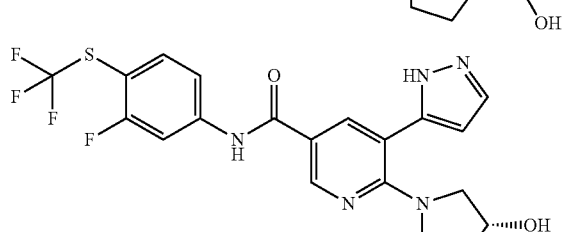
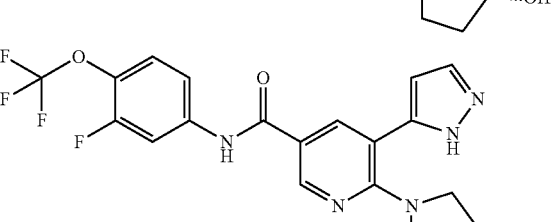
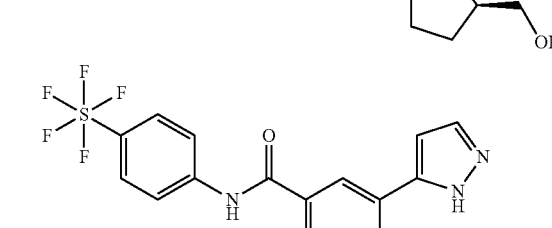
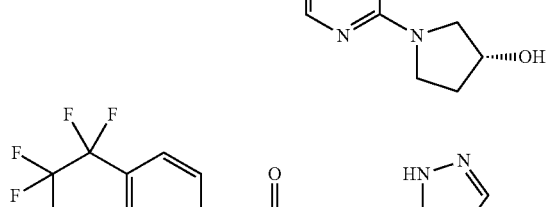

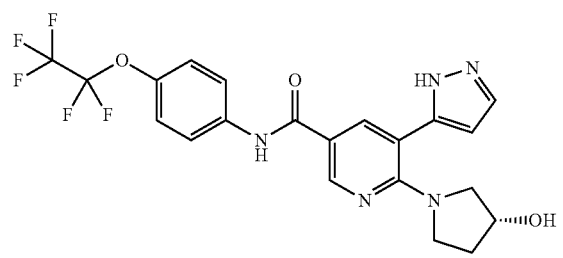
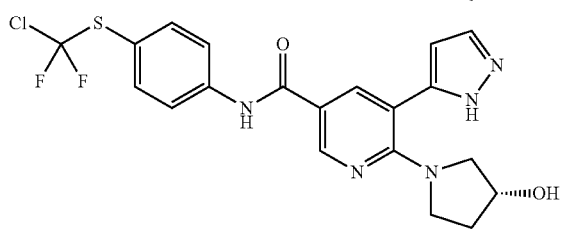
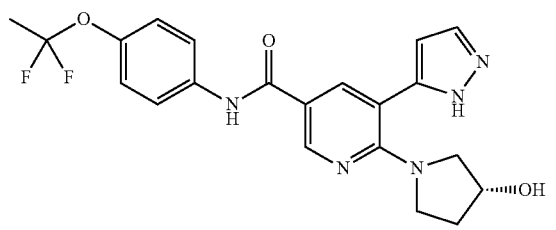
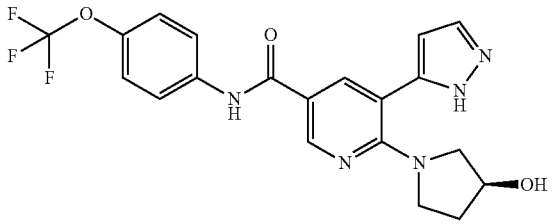
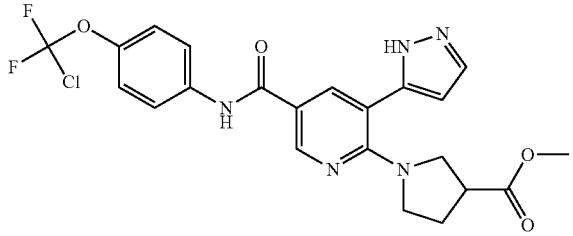
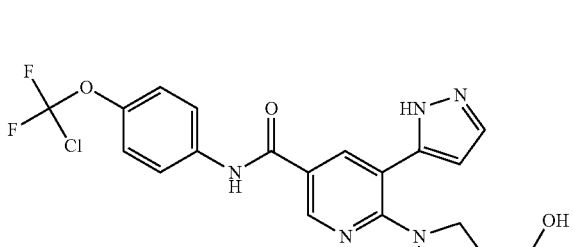
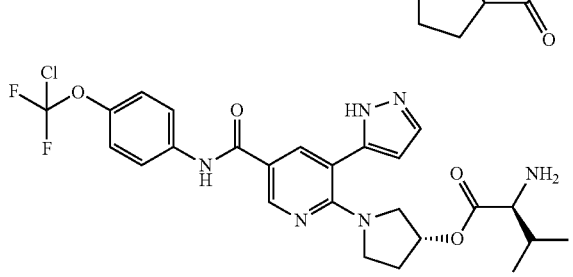
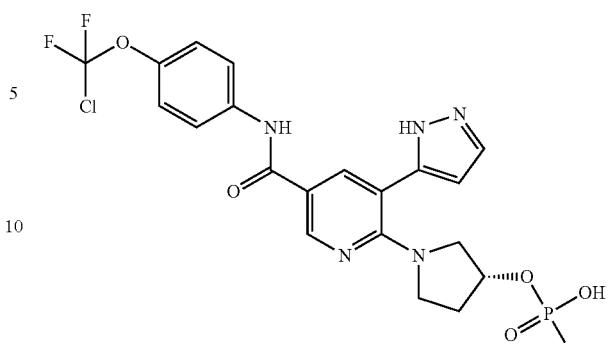
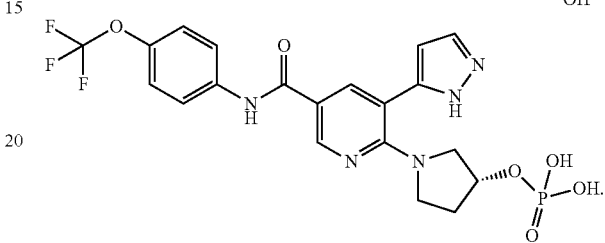
6. The compound of claim 2, or a pharmaceutically acceptable salt thereof, selected from:
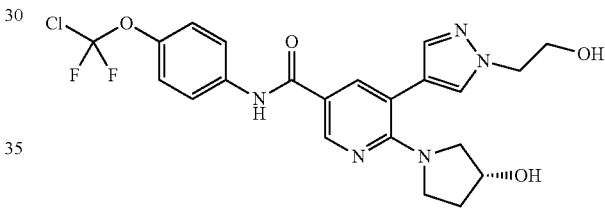
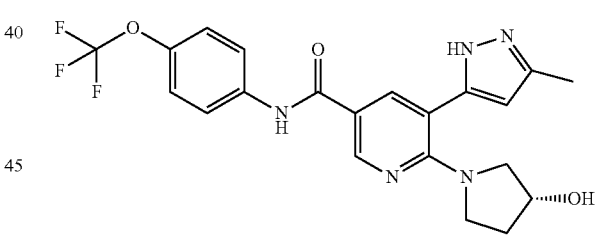
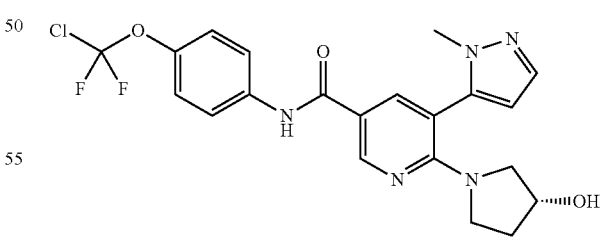
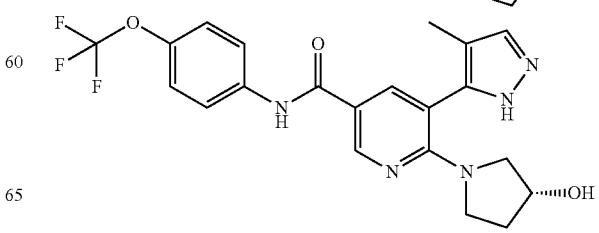

-continued

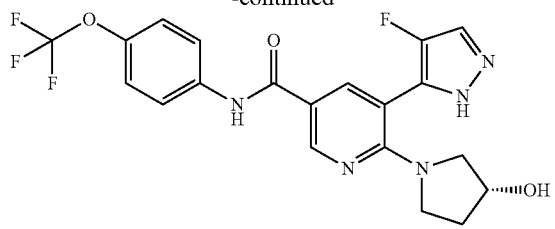

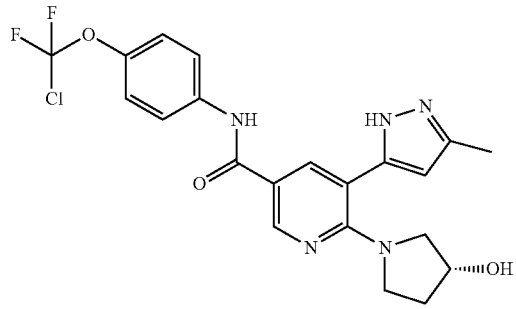

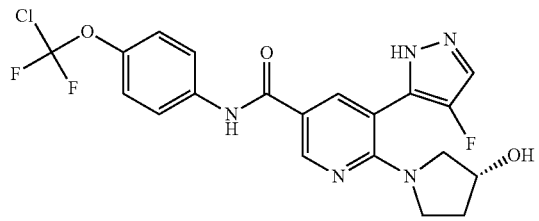

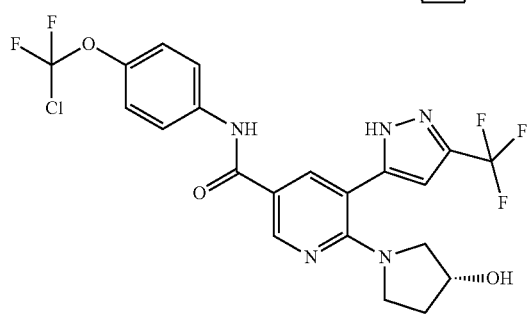

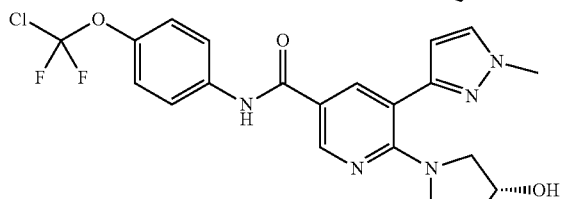

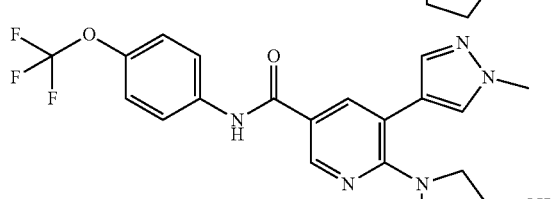

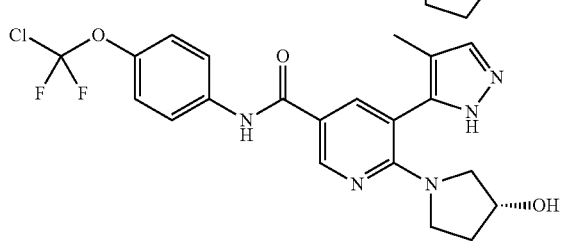

-continued

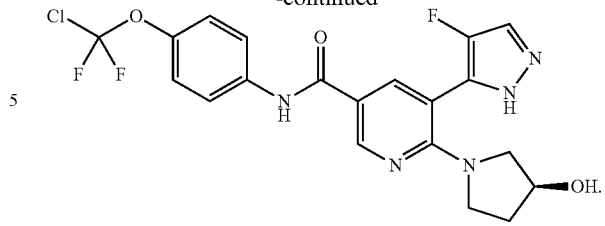

7. The compound of claim 1, or a pharmaceutically acceptable salt thereof, that is:

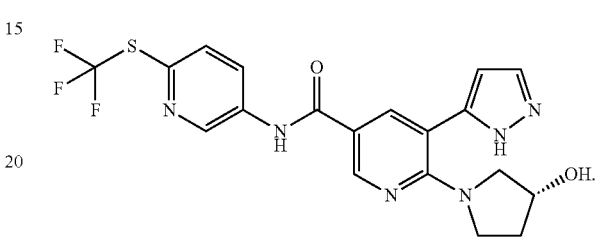

8. The compound of claim 1 that is (R)—N-(4-(chlorodifluoromethoxy)phenyl)-6-(3-hydroxypyrrolidin-1-yl)-5-(1H-pyrazol-5-yl)nicotinamide or a pharmaceutically acceptable salt thereof.

9. A method for treating a patient having a leukemia selected from chronic myeloid leukemia (CML) and acute lymphoblastic leukemia (ALL) comprising administering to said patient a therapeutically effective amount of (R)—N-(4-(chlorodifluoromethoxy)phenyl)-6-(3-hydroxypyrrolidin-1-yl)-5-(1H-pyrazol-5-yl)nicotinamide or a pharmaceutically acceptable salt thereof and optionally a sequential or simultaneous administration of a therapeutically effective amount of a compound selected from imatinib, nilotinib, dasatinib, bosutinib, ponatinib and bafetinib.

10. The method of claim 9 comprising administering to said patient a therapeutically effective amount of (R)—N-(4-(chlorodifluoromethoxy)phenyl)-6-(3-hydroxypyrrolidin-1-yl)-5-(1H-pyrazol-5-yl)nicotinamide or a pharmaceutically acceptable salt thereof.

11. The method of claim 9 comprising a sequential administration of a therapeutically effective amount of a compound of (R)—N-(4-(chlorodifluoromethoxy)phenyl)-6-(3-hydroxypyrrolidin-1-yl)-5-(1H-pyrazol-5-yl)nicotinamide or a pharmaceutically acceptable salt thereof and a sequential administration of a therapeutically effective amount of a compound selected from imatinib, nilotinib, dasatinib, bosutinib, ponatinib and bafetinib.

12. The method of claim 9 comprising administering to said patient a therapeutically effective amount of (R)—N-(4-(chlorodifluoromethoxy)phenyl)-6-(3-hydroxypyrrolidin-1-yl)-5-(1H-pyrazol-5-yl)nicotinamide or a pharmaceutically acceptable salt thereof and a simultaneous administration of a therapeutically effective amount of a compound selected from imatinib, nilotinib, dasatinib, bosutinib, ponatinib and bafetinib.

13. The method of claim 12 wherein (R)—N-(4-(chlorodifluoromethoxy)phenyl)-6-(3-hydroxypyrrolidin-1-yl)-5-(1H-pyrazol-5-yl)nicotinamide is dosed in the range of 90-130 mg/kg.

14. The method of claim 13 wherein nilotinib is dosed at 10-50 mg/kg.

15. The method of claim 14 wherein imatinib is dosed at 50-200 mg/kg.

16. A compound that is (S)-6-(3-Hydroxypyrrolidin-1-yl)-5-(1H-pyrazol-5-yl)-N-(4-(trifluoromethoxy)phenyl)nicotinamide, or a pharmaceutically acceptable salt thereof.

\* \* \* \* \*

UNITED STATES PATENT AND TRADEMARK OFFICE

(12)        CERTIFICATE EXTENDING PATENT TERM
UNDER 35 U.S.C. 156

| | | | |
|---|---|---|---|
| (68) | PATENT NO. | : | 8,829,195 |
| (45) | ISSUED | : | September 9, 2014 |
| (75) | INVENTOR | : | Stephanie Kay Dodd; Pascal Furet; Robert Martin Grotzfeld; Wolfgang Jahnke; Darryl Brynley Jones; Paul Willam Manley; Andreas Marzinzik; Xavier Francois Andre Pelle; Bahaa Salem; and Joseph Schoepfer |
| (73) | PATENT OWNER | : | Novartis AG |
| (95) | PRODUCT | : | SCEMBLIX® (asciminib hydrochloride) |

This is to certify that an application under 35 U.S.C. 156 has been filed in the United States Patent and Trademark Office, requesting extension of the term of U.S. Patent No. 8,829,195 based upon the regulatory review of the product SCEMBLIX® (asciminib hydrochloride) by the Food and Drug Administration. According to United States Patent and Trademark Office records, the original expiration date of the patent as of the date of issuance of this certificate is May 13, 2033. Because it appears that the requirements of the law have been met, this certificate extends the term of the patent for the period of

(94)                                        899 days subject to the payment of maintenance fees as provided by law, with all rights pertaining thereto as provided by 35 U.S.C. 156.

I have caused the seal of the United States Patent and Trademark Office to be affixed this 13th day of November 2025.

John A. Squires
Under Secretary of Commerce for Intellectual Property and Director of the United States Patent and Trademark Office